(12) United States Patent
Schmeling et al.

(10) Patent No.: US 11,716,211 B2
(45) Date of Patent: Aug. 1, 2023

(54) 3D-PRINTED PACKAGING WITH BLOCKCHAIN INTEGRATION

(71) Applicants: James L. Schmeling, Brookeville, MD (US); David A. Divine, Spokane, WA (US); David S. Thompson, Spokane, WA (US); Shay C. Colson, Bellingham, WA (US)

(72) Inventors: James L. Schmeling, Brookeville, MD (US); David A. Divine, Spokane, WA (US); David S. Thompson, Spokane, WA (US); Shay C. Colson, Bellingham, WA (US)

( * ) Notice: Subject to any disclaimer, the term of this patent is extended or adjusted under 35 U.S.C. 154(b) by 1002 days.

(21) Appl. No.: 16/214,053

(22) Filed: Dec. 8, 2018

(65) Prior Publication Data
US 2019/0180291 A1   Jun. 13, 2019

Related U.S. Application Data

(63) Continuation-in-part of application No. 15/721,726, filed on Sep. 29, 2017, now abandoned, which is a
(Continued)

(51) Int. Cl.
*H04L 9/00* (2022.01)
*G06Q 30/018* (2023.01)
(Continued)

(52) U.S. Cl.
CPC .............. *H04L 9/50* (2022.05); *B33Y 50/02* (2014.12); *B33Y 80/00* (2014.12);
(Continued)

(58) Field of Classification Search
CPC .... G06Q 30/0185; B33Y 50/02; B33Y 80/00; G16H 20/10; H04L 9/0637; H04L 9/3268; H04L 2209/38
See application file for complete search history.

(56) References Cited

U.S. PATENT DOCUMENTS 8,239,169 B2   8/2012   Gregory et al.
9,248,611 B2   2/2016   Divine et al.
(Continued)

FOREIGN PATENT DOCUMENTS

WO   WO-2018037148 A1 *  3/2018  ............. G16H 20/10

OTHER PUBLICATIONS

How 3D printing empowers packaging operations, By Lisa McTigue Pierce, Optimization (accessed at http://www.packagingdigest.com/optimization/how-3d-printing-empowers-packaging-operations141014), Oct. 15, 2014, 3 pages.
(Continued)

*Primary Examiner* — Jeremy S Duffield

(57) ABSTRACT

A distributed manufacturing platform and related techniques connect designers, manufacturers (e.g., 3D printer owners and other traditional manufacturers), shippers, and other entities and simplifies the process of manufacturing and supplying new and existing products. A distributed ledger or blockchain may be used to record transactions, execute smart contracts, and perform other operations to increase transparency and integrity of supply chain. Blockchain enabled packaging can be used to track movement and conditions of packages from manufacture, through transit, to delivery.

20 Claims, 18 Drawing Sheets

Related U.S. Application Data continuation-in-part of application No. 15/721,731, filed on Sep. 29, 2017, now abandoned.

(60) Provisional application No. 62/631,509, filed on Feb. 16, 2018, provisional application No. 62/485,967, filed on Apr. 16, 2017, provisional application No. 62/403,125, filed on Oct. 1, 2016.

(51) Int. Cl.
*G16H 20/10* (2018.01)
*B33Y 80/00* (2015.01)
*B33Y 50/02* (2015.01)
*H04L 9/32* (2006.01)
*H04L 9/06* (2006.01)

(52) U.S. Cl.
CPC ......... *G06Q 30/0185* (2013.01); *G16H 20/10* (2018.01); *H04L 9/3268* (2013.01); *H04L 9/0637* (2013.01)

(56) References Cited

U.S. PATENT DOCUMENTS

| | | | | |
|---|---|---|---|---|
| 10,002,277 | B1* | 6/2018 | Endress | H04L 9/3278 |
| 10,002,362 | B1* | 6/2018 | Endress | H04L 9/3278 |
| 10,653,622 | B1* | 5/2020 | Cetinkaya | A61K 9/2095 |
| 2002/0079601 | A1 | 6/2002 | Russell et al. | |
| 2004/0117273 | A1 | 6/2004 | Henderson | |
| 2005/0256776 | A1 | 11/2005 | Bayoumi et al. | |
| 2013/0193621 | A1* | 8/2013 | Daya | B33Y 30/00 425/130 |
| 2015/0052025 | A1 | 2/2015 | Apsley et al. | |
| 2015/0096266 | A1* | 4/2015 | Divine | B29C 70/688 53/558 |
| 2015/0145158 | A1 | 5/2015 | Levine et al. | |
| 2015/0249043 | A1 | 9/2015 | Elian et al. | |
| 2015/0324764 | A1* | 11/2015 | Van Rooyen | G06Q 20/02 705/69 |
| 2016/0098730 | A1* | 4/2016 | Feeney | G06Q 20/3825 705/71 |
| 2016/0122043 | A1 | 5/2016 | Divine et al. | |
| 2016/0152358 | A1 | 6/2016 | Divine et al. | |
| 2016/0280403 | A1 | 9/2016 | Colson et al. | |
| 2017/0046501 | A1* | 2/2017 | Coleman | A61J 7/0418 |
| 2017/0046806 | A1 | 2/2017 | Haldenby | |
| 2017/0185745 | A1* | 6/2017 | Wartski | G16H 20/13 |
| 2017/0253354 | A1 | 9/2017 | Colson et al. | |
| 2017/0253401 | A1 | 9/2017 | Bouthillier | |
| 2017/0257358 | A1 | 9/2017 | Ebrahimi et al. | |
| 2017/0360714 | A1* | 12/2017 | Church | B33Y 50/02 |
| 2018/0089645 | A1 | 3/2018 | McDonald et al. | |
| 2018/0285880 | A1* | 10/2018 | Jerstroem | G06Q 20/202 |

OTHER PUBLICATIONS

Packaging 3D Print—The Global Upheaval That's About to Occur, by John Hauer, 3DPrint.com (accessed at http://3dprint.com/80700/packaging-3d-print/), Jul. 12, 2015, 8 pages.
Adobe co-develops 3D printing software to improve structural designs, By Justin Rubio (accessed at http://www.theverge.com/users/Justin%20Rubio), Sep. 20, 2012, 3 pages.
Stava et al., Stress Relief: Improving Structural Strength of 3D Printable Objects, available at least as early as Oct. 1, 2013, 11 pages.
3D Printing, Opportunities in Packaging, Get3DSmart, by John Hauer, available at least as early as Aug. 6, 2016, 69 pages.
Port of Rotterdam Launches Blockchain Lab, BTCMANGAGER, by Joseph Young, Sep. 29, 2017, 6 pages.
Flexport's epic plan to build a freight empire with its $110M raise, TechCrunch, by Josh Constine, Oct. 6, 2017, 10 pages.
SenseAware, a FedEx innovation, accessible at http://www.senseaware.com/how-it-works/, available at least as early as Oct. 2, 2017, 5 pages.
FedEx Introduces SenseAware, the Next Generation Supply Chain Information Platform, accessible at http://about.van.fedex.com/newsroom/fedex-introduces-senseaware-the-next-generation-supply-chain-information-platform/, Nov. 17, 2009, 6 pages.
SenseAware is FedEx's IoT response to supply chain optimization, RCRWireless News, by Phillip Tracy, available at https://www.rcrwireless.com/20160929/big-data-analytics/fedex-iot-tag31, Sep. 29, 2016, 5 pages.
Digital Print Solutions for Smart Packaging, Xerox, available at https://www.xerox.com/en-us/digital-printing/packaging-solutions/smart?CMP=PPC-PSG&HBX_PK=Smart_Packaging&HBX_OU=50&ADGRP=Packaging_-_Digital_Smart_Packaging_, available at least as eady as Oct. 3, 2017, 5 pages.
Getting Smart with Digitally Printed Packaging, Xerox, available at https://www.xerox.com/en-us/digital-printing/packaging-solutions, available at least as early as Oct. 3, 2017, 6 pages.
Finding Blockchain-Based Security Solutions for the 3D Printing Economy, Bitcoin Magazine, by Giulio Prisco, available at http://www.nasdaq.com/article/finding-blockchain-based-security-solutions-for-the-3d-printing-economy-cm828884, August 8, 2017, 3 pages.
Trusted Internet of Things and Smart Supply Chain Solutions, Chronicled, available at https://www.chronicled.com/, available at least as eady as Aug. 9, 2017, 3 pages.
Blockchain and the future of retail, ETRetail.com, by Singaravelu Ekambaram and Lata Varghese, Aug. 22, 2017, 6 pages.
3D printed Smart Tags ensure 100% authenticity of collectible shoes, www.3ders.org, by Kira, Mar. 10, 2016, 12 pages.
Cubichain Stores Data of 3D Printed Aircraft Paris in Blockchain, 3D Printing, Aerospace 3D Printing, Business, By Joseph Young, Dec. 7, 2016, 9 pages.
Voodoo Manufacturing, Small-Batch Manufacturing With High-VolUme 3D Printing, Voodoo Manufacturing, Available at least as early as Sep. 10, 2017, 20 pages.
Pharma Giants Use Ethereum Network to Prevent Counterfeit Medicine, BTCMANAGER, by Joseph Young, Sep. 25, 2017, 4 pages.
C3IOT, Al & IoT Software Platform for Digital Transformation, available at https://c3iot.com/, available at least as early as Aug. 18, 2017, 5 pages.
Smart sensors improve packaging machinery performance, Packaging Digest—Automation, by Mark Langridge, Apr. 15, 2015, 6 pages.
Smart Contracts: 12 Use Cases for Business & Beyond, Prepared by: Smart Contracts Alliance—In collaboration with Deloitte, available at http://bloq.com/assets/smart-contracts-white-paper.pdf, Dec. 2016, 56 pages.
Technology Innovation Profile: 3D Printing and Going Local, FedEx Healthcare Solutions, http://www.fedex.com/us/healthcare/knowledge-center/technology/technology-innovation-profile-3d-printing-and-going-local.html, available at east as early as Oct. 6, 2017, 3 pages.
3D Printing will make manufacturing local, Epson Insights, Jun. 12, 2017, 5 pages.
The race to connect smart contracts to the real world, American Banker, By Brian Patrick Eha, Aug. 7, 2017, 8 pages.
You can now 3D print digital traceability information, Securing Pharma, by Katrina Megget, Apr. 10, 2018, accessed at https://www.securingindustry.com/electronics-and-industrial/you-can-now-3d-print-digital-traceability-information/s105/a7354/?cmd-PrintView&nosurround-true, 2 pages.
Office Action dated Aug. 13, 2018 in U.S. Appl. No. 15/721,726, filed Sep. 29, 2017, to which the subject application claims priority, 40 pages.
Office Action dated Jan. 22, 2018 in U.S. Appl. No. 15/721,726, filed Sep. 29, 2017, to which the subject application claims priority, 18 pages.
Office Action dated Sep. 19, 2018 in U.S. Appl. No. 15/721,731, filed Sep. 29, 2017, to which the subject application claims priority, 8 pages.

(56) References Cited

OTHER PUBLICATIONS

Office Action dated Apr. 13, 2018 in U.S. Appl. No. 15/721,731, filed Sep. 29, 2017, to which the subject application claims priority, 5 pages.
A Machine Learning Approach for Product Matching and Categorization, Petar Ristoski et al., IOS Press, 2016, 17 pages.
SAP and UPS work to attract partners to join Distributed Manufacturing early adopter program, Printer and 3D Printing News, http://www.3ders.org/articles/20160922-sap-and-ups-work-to-attract-partners-to-join-distributed-manufacturing-early-adopter-program.html, Sep. 22, 2016, 8 pages.
3D Hubs, Wikipedia, https://en.wikipedia.org/wiki/3D_Hubs, accessed on Feb. 3, 2018, 2 pages.
3D Hub, Your go-to service for ordering custom parts online, https://www.3dhubs.com/how-to-3d-print, accessed on Feb. 3, 2018, 2 pages.
Thingiverse features "Get This Printed" button to allow users to order 3D prints directly via 3D Hubs, Printer and 3D Printing News, http://www.3ders.org/articles/20150421-thingiverse-features-get-this-printed-button-order-3d-prints-directly-via-3d-hubs.html, 8 pages.
Notification of Transmittal of the International Search Report and Written Opinion of the International Searching or Authority, dated Jan. 18, 2018, from PCT/US17/54643, 17 pages.

\* cited by examiner

3D-PRINTED PACKAGING WITH BLOCKCHAIN INTEGRATION

RELATED APPLICATIONS

This application is a continuation-in-part of U.S. patent application Ser. No. 15/721,726, filed Sep. 29, 2017 and U.S. patent application Ser. No. 15/721,731, filed Sep. 29, 2017, both of which claim the benefit of U.S. Provisional Application No. 62/403,125, filed Oct. 1, 2016, entitled Distributed Manufacturing, and U.S. Provisional Application No. 62/485,967, filed Apr. 16, 2017, entitled Blockchain Enabled Packaging. This application also claims the benefit of U.S. Provisional Application No. 62/631,509, filed Feb. 16, 2018, entitled Distributed Manufacturing and Packaging of Parts. All of the foregoing applications are incorporated herein by reference. Moreover, any or all of the techniques, methods, systems, packages, devices, examples, and/or embodiments described in the foregoing applications may be combined in whole or in part with any other of the techniques, methods, systems, packages, devices, examples, and/or embodiments described therein.

BACKGROUND

Bringing a new product to market, from idea generation to delivering the finished product to customers, has historically been a long and arduous process. From the time a company or individual first conceives of a new product to the time a customer holds the finished product may take months or years, depending on the nature of the product. Furthermore, the cost and complexity of manufacturing prevents many products from ever being made at all. For instance, some traditional manufacturing techniques such as casting and injection molding have significant upfront costs associated with creating molds or tooling which make them unsuitable for small runs of products. Also, traditional manufacturing techniques such as casting, molding, and machining may be unable to produce certain part geometries (e.g., single piece hollow geometries, intricate internal geometries, internal passages, etc.).

More recently, advances in additive manufacturing or 3D printing have made it possible to produce prototypes and even small volumes of commercial products without the upfront costs associated with creating molds and tooling. However, existing additive manufacturing technologies are relatively slow (as compared to injection molding, for instance) and are, consequently, not suited to producing large quantities of products quickly. Additionally, while new 3D printers are being developed that can print high quality parts using a wide variety of different materials (e.g., plastics, metals, ceramics, etc.), these printers are expensive and the vast majority of designers and businesses do not have access to these high-end 3D printers due to the cost and the fact that they are not yet widely deployed. Further, businesses that have need of such high-end printers often cannot justify the cost due to low printer utilization rates. That is, while they could use such a printer, they could not keep it fully busy.

Additional challenges to commercialization of new products, and even manufacture of known parts, include lack of trust amongst parties to the process (e.g., designers, overseas manufacturers, customers, etc.), interoperability (e.g., amongst design software, part models, printer capabilities and software, etc.), intellectual property concerns (e.g., preventing unauthorized reproduction or copying of products or designs, difficulty/cost of licensing IP, etc.), post processing and finishing requirements, product assembly, quality assurance, packaging considerations (e.g., even 3D printed parts still need to be packaged for delivery to a seller or end customer), shipping and delivery considerations (e.g., for small or inexpensive parts, traditional shipping may cost as much or more than the part itself), supply chain integrity, environmental concerns, and the list goes on.

Globalization of the economy has vastly increased the options available for manufacturing, but has compounded many of these challenges. Thus, there remains a need to improve the process of bringing new products to market, and to simplify the process of manufacturing and supplying new and existing products.

BRIEF DESCRIPTION OF DRAWINGS

The detailed description is set forth with reference to the accompanying figures. In the figures, the left-most digit(s) of a reference number identifies the figure in which the reference number first appears. The use of the same reference numbers in different figures indicates similar or identical items.

DETAILED DESCRIPTION

Figure 1:
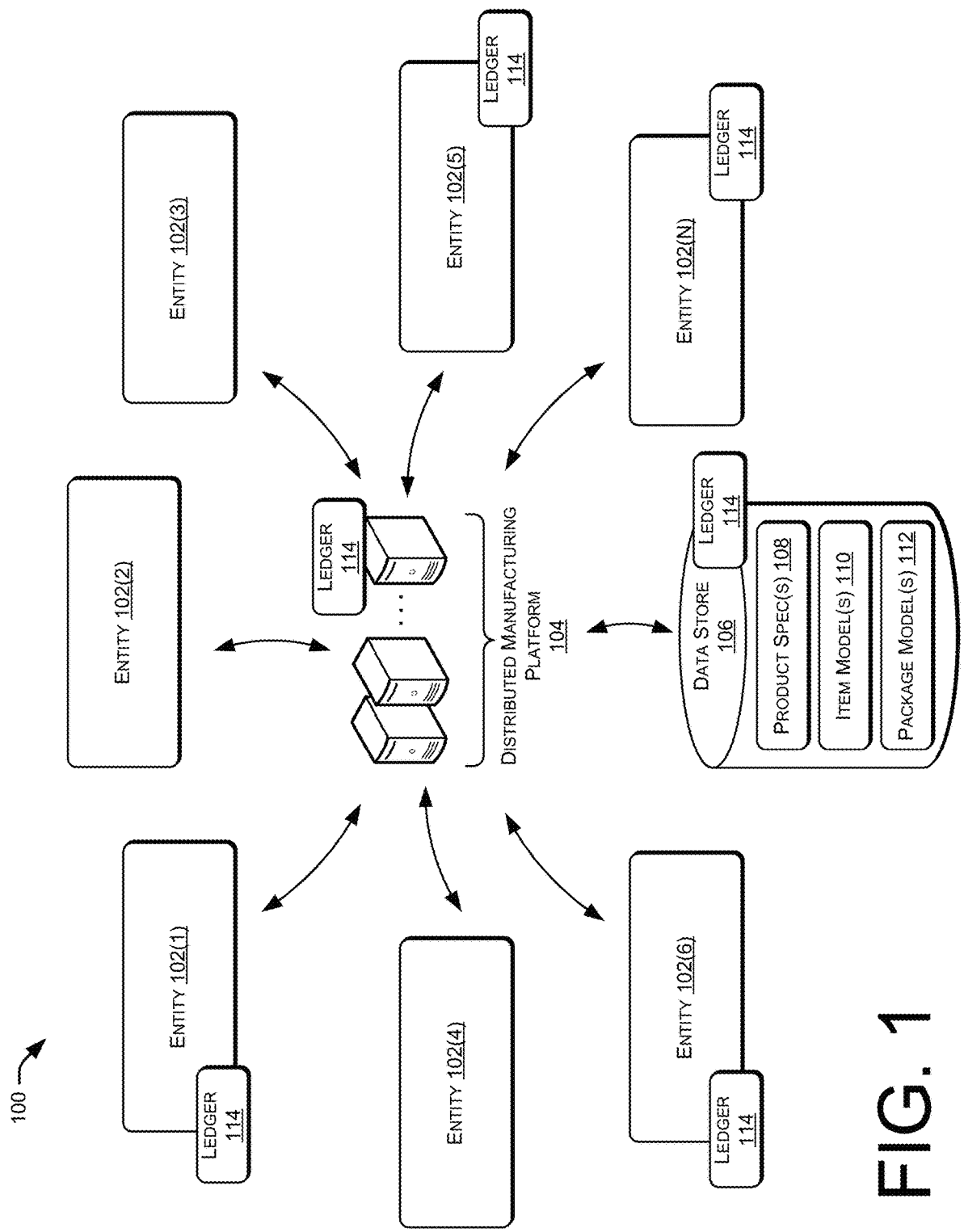
FIG. 1 is a schematic diagram of an example system having a centralized distributed manufacturing platform.

This application describes a distributed manufacturing platform and related techniques that connect designers, manufacturers (e.g., 3D printer owners and other traditional manufacturers), shippers, and other entities and simplifies the process of manufacturing and supplying new and existing products. The application also describes techniques using a distributed ledger or blockchain to record transactions, execute smart contracts, and perform other operations to increase transparency and integrity of supply chain. By way of example and not limitation, the techniques described herein can shorten the time to bring products to market, eliminate inefficiency and manufacturing downtime, reduce production costs, shorten shipping times and distances, reduce packaging size and cost, reduce transaction costs, track and record movement of products in the supply chain, provide digital rights management for part designs, and provide an audit trail to identify and discourage counterfeit goods.

Unless otherwise specified, the terms "item" and "product" are used synonymously herein to refer to any physical object made by one or more parties. The item or object may be comprised of a single part or multiple parts, and may be made by additive manufacturing and/or traditional manufacturing techniques. The term "unit" refers to a single instance of an item or product, and the term "units" refers to multiple instances of the item or product. The terms "blockchain" and "ledger" are used interchangeably herein and mean a digital ledger to which transactions, smart contracts, and other information can be written.

While many of the examples are described as using 3-D printing and/or being implemented by or in connection with a 3-D printer, the techniques described herein are also applicable to other forms of manufacturing. Unless specifically noted to the contrary, the terms "3-D printing" and "3-D printer" are used herein to mean additive manufacturing and additive manufacturing machines, respectively. Unless otherwise specified, the term "manufacturing" includes both additive manufacturing and traditional manufacturing. By way of example and not limitation, additive manufacturing techniques include material extrusion (e.g., fused deposition modeling or FDM), vat polymerization (e.g., stereo lithography or SLA, digital light processing or DLP, continuous digital light processing or CDLP), material jetting (e.g., material jetting or MJ, nanoparticle jetting or NPJ, drop on demand or DOD), binder jetting or BJ, powder bed fusion (e.g., multi jet fusion or MJF, selective laser sintering or SLS, direct metal laser sintering or DMLS, selective laser melting or SLM, electron beam melting or EBM), direct energy deposition (e.g., laser engineering net shape or LENS, electron beam additive manufacturing EBAM), sheet lamination (e.g., laminated object manufacturing or LOM), and the like. By way of example and not limitation, traditional manufacturing techniques include molding (e.g., injection molding, blow molding, blow fill seal, etc.), casting (e.g., sand casting, investment casting, etc.), machining (e.g., milling, turning, drilling, etc.), forming (e.g., shearing, stamping, punching, etc.), joining (e.g., welding, brazing, soldering, etc.), finishing operations (e.g., deburring, sanding, polishing, knurling, sand blasting, etc.), post processing (e.g., annealing, quenching, cryogenically freezing, painting, powder coating, plating, etc.), and the like.

Overview of Distributed Manufacturing

Distributed manufacturing refers to a manufacturing approach in which, instead of having a company design and manufacture a product and then have the product shipped to a customer, products are designed, manufactured, finished, assembled, and/or shipped by one or more entities based on a variety of factors including, for example, product requirements, manufacturing capabilities and availability, location of parties, and the like. For example, one or more customers, designers, manufacturers (e.g., entities owning 3D printers and/or traditional manufacturing equipment such as molding equipment, casting equipment, forming equipment, or machining equipment such as CNC machines, automated lathes, etc.) may be linked and coordinated via a software platform such that orders, plans, designs, and other order details can be input and items can be created (autonomously, semi-autonomously, or manually), packaged (including retail and/or shipment packaging) ready for shipment by common carrier or individual contractors. The distributed manufacturing platform may also include shippers (e.g., private or governmental postal services, shipping companies, common carriers, delivery services, etc.), fulfillment services, merchants (e.g., bricks and mortar merchants, e-commerce merchants, etc.). In some examples, the distributed manufacturing platform may also include makers of 3D printers or other automated manufacturing equipment, CAD software developers, post processing companies, finishing companies, assembly companies, quality assurance companies, e-commerce merchants or marketplaces of e-commerce merchants, fulfillment companies, payment processing companies, brokerage companies to trade or exchange between and/or among various different forms of money (e.g., fiat currency, crypto currency, tokens, credits, gift cards, etc.), rating/reputation services, security companies, and/or any other entities providing or using services related to product supply chain.

Orders can be placed directly via the platform, or the platform can operate as a white-label/back-end component to an otherwise independent business (e.g., marketplace or merchant). In some examples, designers may design products and offer them for sale to customers via the platform. Additionally, or alternatively, customers may provide product specifications or request bids for custom products, and designers may bid on or provide proposals to provide the requested custom products. Customers may specify budgets, desired delivery dates, delivery locations, and other criteria. The platform allows entities to advertise their capabilities (e.g., designers can specify the software packages they work in, manufacturers can specify the types of 3D printers and other manufacturing equipment they have at their disposal, shippers can specify their available modes of shipping and delivery, etc.) and availability (e.g., man or machine hours available per week, number of machines, existing jobs, delivery capacity and/or speed, etc.). The platform may then match designers, customers, manufacturers, and any other entities applicable for a given job, based on the customer criteria and the capabilities of the various entities. In some examples, the matching of entities may be performed autonomously by the platform. In some examples, the matching may be performed by one or more of the entities (e.g., the customer, a merchant, a manufacturer, a shipper, a combination of these, or the like) with or without suggestions by the platform. In some examples, the matching may be performed interactively by allowing multiple entities to negotiate and/or bid on a job or transaction.

By way of example, consider a company or individual that needs 10,000 units of a widget manufactured as quickly as possible. Such a company or individual can utilize the platform to distribute the manufacturing across the required number of machines to fulfill the order in the desired time (e.g., if time allows, one machine may be used to print 10,000 units over a large amount of time; however, if time is short, 10,000 machines may be used simultaneously, with each printing one unit). A cost algorithm may allocate charges, expenses, profits, etc., in any desired manner, such as in accordance with the desired outcomes and required component inputs.

In another example, companies can utilize this platform (i.e., all or part of a distributed manufacturing platform) through a separate website on which end customers have the ability to order items, but the ordering, payment, manufacturing, shipping, fulfillment, and other necessary business operations may be completed by the platform with complete transparency to the end customer. At the time the customer orders the item, the item may be nothing more than a design (e.g., product specification sheet, computer model, engineering drawings, etc.), and the item can be manufactured, finished, assembled, shipped, fulfilled on-demand (in a matter of minutes for some simple products, to a few days or weeks for larger or more complex products). Traditional consumer products or electronics businesses could exist in a completely automated fashion on the distributed manufacturing platform without owning any of their own infrastructure. Entire companies could be started and grow on this platform by doing nothing more than uploading a design file and then submitting received orders or waiting for orders to come in through the platform. Everything else would be facilitated and fulfilled autonomously through this platform.

The platform may facilitate automated and appropriate payments to and/or from the various buyers, sellers, manufacturers, designers, shippers and/or other actors. In some example, the purchase price of an item may be calculated to cover any license and/or use fee(s) for the designer plus an appropriate margin, the materials and wear costs for the owner of a 3-D printer used in the manufacture, plus an appropriate margin, the actual shipping costs based on the individual item and final shipment location, as well as a margin paid to the platform for facilitating the transaction and any other required payments. These payments may be made in fiat currency, cryptocurrency (e.g., Bitcoin, Ethereum, or other altcoins), tokens, credits, commodities, points, or any other store or transfer of value. In some examples, the platform may facilitate transfer or exchange between one or more of these forms of payment. In some examples, the payments may be made directly between participants of the platform, while in other examples, the buyer may provide payment to the platform (e.g., at the time an order is placed), and the payment may be held in escrow at the platform until the product is delivered or other milestones are met. For instance, in some examples, a transaction fee may be charged by the platform at the time an order is placed and/or upon completion of the transaction (e.g., delivery of the units), a portion of payment may be transferred or released to the designer at the time the order is placed, a portion of the payment may be transferred to a 3D printer owner that is to print the units prior to or after the units are printed, a portion of the payment may be released to a third party company perform finishing operations or assemble the unit from multiple parts, a portion of the payment may be released to a shipping company when the units are put into the care of the shipper or once the parts are delivered to the customer, and a remaining portion of the payment may be transferred or released to the seller upon completion of the transaction.

In some examples, the platform facilitates reputation/review services (e.g., a rating system or forum for quality assessment and/or expressions of user satisfaction and/or dissatisfaction with a party, printer, or other piece of equipment), determining shipping costs and coordination, and storing and distributing design files to the chosen manufacturing device. In some examples, the chosen manufacturing device may be a 3-D printer or other asset that is an available and/or capable device, sufficiently highly rated, and closest and/or sufficiently close to the final destination of a buyer or shipment receiver (to minimize transit distance and cost).

Matching an order request to a production machine (e.g., 3D printer) may occur based on any number of factors or criteria, individually or in combination, including price, type of product or printer, availability, quality requirements, capabilities, reputation, shipping cost, security, etc. Location nearest the final destination may be weighed in making the printer selection decision so as to minimize costs, delay, environmental impact, etc. Additional matching criteria could be based on pricing, number of items ordered, activity level of required printers (i.e. how busy is the needed machine), print materials or final quality. In a further example, a reverse-auction style selection system would allow printer owners, designers and/or shippers to bid on jobs. Other example criteria include a maximum distance from the final location, a minimum rating (e.g., job quality reputation) for the printer owner, a minimum quality level for the individual printer, etc. These and/or numerous other criteria may be used individually or in combination to match parties on the distributed manufacturing platform. Various non-limiting examples are provided throughout this application.

In addition to manufacturing the specific item, the platform can also facilitate the ability to distribute packaging and/or manufacturing utilizing additive manufacturing, which can be integrated into the distributed digital supply chain created by this platform, regardless of the type or location of the item to be packaged. The item to be packaged could be printed directly around the item itself, created simultaneously on a separate printer, created via a different method, or otherwise integrated into the packaging created by the platform. Therefore, a product could be created at a 3D printer, and the packaging for the product could be printed around the product as the product was being created. Alternatively, the packaging could be printed around the product after the product was printed. The package and the item could be printed or otherwise manufactured at the same or different physical locations or facilities.

In some examples, the platform may help enforce and/or verify product quality and/or authenticity. For instance, quality control can be accomplished at least in part by having each participating printer create and send an automated, predefined test calibrated printed part to demonstrate quality at regular intervals (i.e. monthly/quarterly/after a certain number of print jobs/etc.). In an example, each 3D printer would send to a quality authority of the platform example output that demonstrates fitness for particular level(s) of manufacturing jobs. Additionally or alternatively, once a part is printed but before it is packaged or shipped, the printer or an operator may be asked to scan, photograph, or otherwise document the part and send the documentation to the buyer for approval. Additionally or alternatively, one or more quality control or certification authorities may be parties to the platform. In that case, parties to a transaction may specify that products meet certain standards or comply with certain regulations and may require inspection or certification by one of the quality control or certification authorities.

Traditional "printer bureaus" such as Shapeways™ will be able to leverage this platform to fulfill print jobs, but individual printer owners can lease manufacturing time on their device, as well, providing a return on the printer owner's investment in the 3D printer. Similarly, contract manufacturers may offer their capabilities via this platform, as well as individuals that have home workshops with one or more manufacturing machines.

In addition to facilitating distributed manufacturing, end customers can put a design order requesting design of a new product not yet in existence. Additionally or alternatively, the platform can facilitate re-sale of existing designs in a marketplace style in which designers can upload their designs and make them available for purchase, as well as storing individual design specifications that can be resold and reused dynamically, with appropriate payment per the previous model. In some examples, designers may be both the designer and customer by ordering their own designs for subsequent distribution and sale.

File types and conversions of files between file formats may be done by multiple actors—including the customer, printer owner, designer, printer manufacturer, computer aided design (CAD) software, or a third party integrator whose service is defining the necessary settings or conversions for a given piece of software or desired print output.

In some examples, as discussed in more detail in later sections, any or all transactions performed via or in relation to the platform may be recorded to a ledger or blockchain, which may be distributed and stored on multiple computers (e.g., computers of members or users of the platform, computers of the platform itself, etc.). Examples of transactions that can be recorded to the ledger include an order of one or more units of an item, transfer of funds from one party or account to another, completion of any operation or step in producing or delivering the unit(s) (e.g., the act of printing the unit(s), packaging of the unit(s), physical transport of the unit(s) from one place to another, pickup of the unit(s) by a shipper, movement of the unit(s) between vehicles and/or past checkpoints during transit, delivery of the unit(s) to a customer, signature or other acknowledgement of receipt by the customer, etc.), verification of authenticity and/or quality of materials and/or unit(s), identification and/or licensing of intellectual property rights, identification parties involved, identification of equipment used to produce the unit(s), or any other information generated as part of the transaction. When used, such a ledger provides an immutable record of transactions on the platform, and allows for auditing and tracking of units throughout the supply chain.

The examples described herein involve a variety of different actors. These "actors" are also sometimes referred to as "parties" or "entities" and unless otherwise specified, refer to any person, company, governmental body, group, or organization that interacts or engages with the platform in some way. Some of the more common actors and their potential interactions with the platform are described below by way of example and not limitation.

Designers: Designers are responsible for creating and uploading digital design files, such as computer aided design (CAD) files, part models, package models, engineering drawings, product specifications, blueprints, images, renderings, etc. These digital design files may or may not include printer settings (though final printer settings may need additional input from printer manufacturers, printer operators, customers, or the like), material specifications, surface finishes, manufacturing specifications (e.g., manufacturing processes, machines to be used to manufacture, required tolerances, etc.), or the like. These designs can then either be ordered by the designers themselves, or sold to customers directly or through a merchant interface of the platform or a third-party site. In other examples, customers may place orders or request quotes for custom products that are not yet in existence, and the designers may create and upload the designs responsive to customer order or request for quote.

Platform (software marketplace/broker): The platform facilitates payment, quality feedback on outputs, "matching" of parties (including reverse bidding or other pricing methodologies), hosting design files (and storing, sharing, reusing, etc. such files), quality assurance on individual printer outputs (e.g., print a job based on a particular file each month/quarter/year/etc. and send to some aspect of the platform for quality assurance review), picking the nearest capable printer to minimize shipping distance and cost, etc.

Printer Owner: Printer owners can be individuals that own one or more printers for other purposes (such as their own manufacturing needs) or printers owned specifically to participate in this platform (such as the existing "service bureau" model).

Traditional Manufacturer: Traditional manufacturers include contract manufacturers, individuals, or other entities that offer any manufacturing capabilities other than additive manufacturing, such as molding, casting, machining, forming, etc. In some examples, parties may be both printer owners and traditional manufacturers.

Shippers: Shippers are any entity that transports items and include common carriers, printer owners, courier services, individual delivery agents, or the like. In some examples, common carriers may be organized to provide information that allows calculation of final shipping costs based on the required variables. In addition, printer owners may offer delivery for an additional fee, as a value added service, etc. Local or regional deliveries could also be completed by independent contractors (in the manner of, or elements of similarity with, Uber, Amazon Flex, etc.), or other crowd-sourced methods, particularly if the final product is printed extremely close to the final location. In other examples, the shipper may be eliminated and the customer may pick up the product from the printer owner, designer, assembler, or other party to the transaction.

Customers: Customers purchase items or other services from other parties via the platform. Customers may provide product requirement specifications, or choose an order from an existing design/designer, and provide payment (payments through the platform for the individual actors involved).

Printer Manufacturer (or printer software producer): Printer manufacturers are those that manufacture 3D Printers or additive manufacturing equipment. Printer manufacturers may provide products, supplies (e.g., filament or other print media), technical support and other services to other parties using the platform. For example, printer manufacturers may provide final printer settings or access to settings (i.e., software license) that may be set by either the designer or the customer or the printer owner. Additionally or alternatively, printer manufacturers may provide integration software such as application programming interfaces (APIs) that enable translation of file formats, remote control of printers or print jobs, or software development kits (SDKs) that allow printer owners or third party developers to develop software programs to interface with the printers. In some examples, printer manufacturers may also be printer owners that offer printing capacity via the platform. In some examples, printer manufacturers may offer membership or integration with the platform along with a purchase of one of their printers in order to help defray the costs of the printer and provide a purchaser with a faster return on investment (ROI) in the printer.

The foregoing are merely examples of a few common actors that may engage with the platform. These and numerous other actors are described throughout this application in the context of various example scenarios and use cases. The distributed manufacturing techniques described herein provide flexibility in the manufacturing process. Numerous variations and use cases are possible using the distributed manufacturing techniques described herein and are within the scope of the application. The following are just a few capabilities that can be implemented using such variations of distributed manufacturing techniques.

In some examples, the platform may receive an inquiry from a customer regarding a product that the customer wants to create, such as for shipment to the customer or an end customer (i.e., a customer of the customer). The platform may help the customer to find a designer, so that the product and/or packaging for the product can be 3-D printed. The platform may provide the customer with pricing information, area of specialty, turn-around time, customer feed-back and/or quality review information about various designers. The platform may also provide designer selection recommendation(s). The platform may receive input from the customer, regarding a selection of a designer. The platform may put the customer and designer into contact, so that the design process can begin. The platform may receive payment from the customer, and provide payment to the designer, using all/part of the payment received. The platform may manage the output of the design process, such as data/instruction file transfer, storage and/or translation. The platform may provide the customer and/or designer with information regarding available 3-D printers, their quality assurance ratings, customer feedback, geographic location, pricing information, turn-around time and/or other information. The platform may also provide 3-D printer selection recommendation(s). The platform may receive payment from the customer, and provide payment to the 3-D printer owner, using all/part of the payment received. The platform may assist the customer with issues of how many product items are needed, and the number of printers to utilize and the geographic location of each. The platform may monitor and/or coordinate the transfer of data from the 3-D designer to the 3D printer. The platform may provide progress reports to the customer and/or designer, as the product and/or the packaging of the product is 3-D printed. The platform may provide the customer with information regarding shippers available at the site of the printer and/or relative distances of the shippers from the site of the printer. The information may include rates/bids, expected delivery time, quality assurance feedback, etc. The platform may receive payment from the customer, and provide payment to the shipper, using all/part of the payment received. The platform may receive instructions from the customer for shipping, and may notify the selected shipper to pick up the product, within its 3-D printed packaging. The product may be shipped, by the shipper, to the customer or to an end customer. The platform may provide the customer and/or the end customer with billing, shipping and/or other product information.

Overview of Blockchain Enabled Packaging

As discussed above, any or all transactions performed via or in relation to a distributed manufacturing platform, such as described herein, may be recorded to a ledger or blockchain, which may be distributed and stored on multiple computers (e.g., computers of members or users of the platform, computers of the platform itself, etc.). These transactions include, but are not limited to, transactions between parties (e.g., purchase transactions, payment transactions, etc.). These transactions may also include transactions between and/or among machines or equipment (e.g., printers, CNC machines, robotic arms, scanners, etc.), packages, items, and other systems. These transactions between and among machines and inanimate objects may be accomplished through one or more wired or wireless connections that connect the machines and inanimate objects to the platform and the internet-of-things (IoT), and allow the transactions to be written to the ledger.

Items and/or packaging with the capability to interact with blockchain technologies represents the link between the digital, distributed ledger of the blockchain and the physical world which we all move through. Creating packaging, whether through traditional methods, or through additive manufacturing techniques, that can read from and/or write to a blockchain (public, private, permissioned, secure, or otherwise) as well as execute predetermined contractual interactions (whether through Ethereum, Hyperledger, or some other smart-contract self-execution system) provides a fundamental re-conception of what's possible in our world today and in the future. In some examples, the smart contract terms may be written to the blockchain and publicly readable. In some examples, the smart contract may be cryptographically hashed and the hash of the smart contract may be written to the blockchain and the parties to the smart contract may maintain a private key usable to decrypt the smart contract from the hash.

By creating packaging through additive manufacturing, a unique opportunity exists to capture real-time information about the package and its contents utilizing blockchain technology. Because the packaging is created by a 3D printer (or some other additive manufacturing process), this moment-in-time creation process presents an opportunity to create the initial interaction on a blockchain—including writing information about the date, time, and location of creation, the packaging system or machine used to package the contents, methods or materials contained within the package, the contents of the package, the destination of the package, authorized users or uses, shipping requirements, promises related to delivery time or condition, customs declarations, payment information, intellectual property rights, or other relevant information. While these techniques are described in the context of items and/or packaging made by additive manufacturing, the techniques can also be adapted to items made by traditional manufacturing techniques and/or packaged in conventional packaging. For instance, date, time, location, batch, manufacturing equipment identifiers, settings, and other information may still be written to the blockchain by one or more computers or other devices involved in the traditional manufacturing process. Because of blockchain's variable deployment methodologies, this information can be unencrypted and publicly accessible, encrypted but publicly verifiable, privately permissioned (e.g., requiring an authentication credential, security clearance, etc.). The particular blockchain used to record the creation can also allow for a varied level of control on a per-package, per-shipment, per-location, per-customer, or other customized basis. For example, in some instances every operation may be recorded to the blockchain, while in other examples, certain important transactions may be recorded to the blockchain while other transactions are recorded "off-chain" in a traditional ledger or data store. In some examples, transactions may be batched off-chain and written to the blockchain in a batch periodically (e.g., daily, weekly, monthly, etc.) or upon occurrence of an event (e.g., performance of a contract or delivery of a product). This level of control, verification, and detailed information can be applied to a broad range of industries, including retail packaging, consumer products, consumer electronics, domestic and international shipping and freight, pharmaceuticals, medical devices, food and beverage, and military and defense applications, to name just a few.

Consider an example in which an item is packaged utilizing blockchain-enabled 3D printed packaging. The item itself may be manufactured using traditional manufacturing techniques that simply utilize blockchain-enabled 3D printed packaging, or the item itself may be customized to the consumer and created through an additive manufacturing process. The 3D printed packaging may be used to ensure that only the intended recipient of the item is allowed to take custody of the item. The nature of blockchain's structure and the underlying public-key/private-key encryption model means that an entry on the on the blockchain can be made for any individual using their public key, but authenticated only by the individual in possession of the corresponding private key. For instance, an intended recipient (e.g., customer, owner, recipient, patient, etc.) can use their own private key or other blockchain-based authentication mechanism to pick up the package. Conversely, the private keys of the seller, printer owner, manufacturer, shipper, or other party can be incorporated to prove that the party is who they say they are and that they are authorized to take custody or otherwise interact with the package at each stage of the supply chain and/or at each phase of the transaction. These authentications are written to the blockchain and create a record and audit trail of the package from inception to delivery. The entries in the blockchain may be publicly available or may be encrypted so that they are accessible only to the authorized parties. The authorization can come in several forms. In one instance, a visual code such as a barcode or Quick Response (QR) code can be displayed on the packaging which can be verified by a scan performed by a mobile device (phone, tablet, point of sale terminal, etc.) containing the private key of the relevant party (e.g., customer, owner, recipient, patient, seller, manufacturer, designer, etc.) In another example, the public/private key pairs can be exchanged using Near Field Communication (NFC) or a Radio Frequency Identification (RFID) chip. This can be incorporated directly into the packaging, as well as a device (phone, tablet, point of sale terminal, token, etc.) possessed or used by the relevant parties. Other sensors, chips, or data repositories can be integrated within the packaging to provide blockchain transaction and integration capability, including WiFi, Bluetooth, cellular radio, ZigBee, or other communications sensors and/or modules. An additional suite of sensors, chips, and/or modules can provide relevant data repositories about the package by writing their data to the same or different blockchain. Example sensors, chips, and/or modules include, but are not limited to, accelerometers, gyros, temperature sensors, humidity sensors, compasses, GPS modules, cameras, processors, CPUs, GPUs, integrated circuits, memory, batteries or other power sources, contract module defining contract terms, blockchain read/write module, hardware security modules, etc. These transactions can be written to a verifiable blockchain—public, private, or some hybrid therein—where parties (e.g., customers, sellers, manufacturers, printer manufacturers, regulators, insurance companies, and other parties) can communally verify transactions and ensure that all parties in each transaction are interacting appropriately. Relevant data can be either embedded directly into the relevant blockchain, or linked to transactions and individual parties and verified through related sidechains or other blockchain-derived structures that provide a pre-computed hash value of the data, otherwise known as providing "proof of existence." These interactions can be mediated by pre-determined contractual negotiations which can also be represented on the relevant blockchain.

In some examples, smart-contract technology can automatically enable payment at the time of purchase, upon performance of contract terms, or upon occurrence of certain milestones or events. In some examples, the smart-contracts can include compliance-based payment mechanisms pre-written into the contract (i.e. the customer pays the full price of the item if they do not comply with the prescribed contract terms, or receives incentive payments based on short- or long-term performance of contract terms). This smart-contract capability can further be expanded by creating a compliance-based cost model for items, whereby the blockchain-enabled packaging creates verifiable logs detailing which individual performed contract obligations at which time. By writing this data to an accessible blockchain, providers will be able to track use of items and compliance with contract terms (e.g., warranty terms, license terms, etc.) that can be easily, automatically, digitally, and irrefutably verified.

In another example, 3D printed packaging with blockchain capability offers access control to contained items. In this example, the items are packaged in separate compartments of the package (or in separate packages), and access is granted to each item or group of items in accordance with a schedule, proof of performance of one or more tasks, proof of identity, or other predefined contract provisions (which can be pre-written into the packaging utilizing smart-contract technology). Items can be released automatically when the specified contract terms are met. This release can be accomplished utilizing an actuator, lock, tabbed hinge, or other self-enforcing security mechanism of the package.

Blockchain-based monitoring can also extend to the disposal of unused items or portions of items, worn items, broken items, hazardous items, etc. Such items can be logged back into a seller, distributor, disposal site, other public locale where they can be destroyed, thereby tracking the entire lifecycle of the item from production to destruction.

In another example, the contents of a package can be verified at the point of production and moment of packaging. Verification of package contents include a range of options—including both number and type of items, but also verification within the items contained. For example, contents of packages can be verified in terms of authenticity, quantity, and dosage, to prevent fraud, misrepresentation, or substitution for counterfeits during shipment, transport, or storage. If the packages also include tamper preventing and/or tamper evident features such as tear strips, water marks, materials that react to exposure to air, sensors (e.g., temperature sensors, humidity sensors, light sensors, inertial sensors, or other sensors), etc., then recipients can be confident that the contents of the package are authentic and in the same condition as when they were packaged. Verification of package contents can be accomplished in multiple ways. In one example, contents can be identified/verified (e.g., by optically or chemically scanning the contents, by a quality assurance or certification authority, etc.), and the identification of the contents can be recorded using, for example, a one-way mathematical hashing function, which results in a unique and verifiable output that is written to the blockchain. In another example, verification can be done with integrated sensors that indicate changes or tampering to the package. These indications can be visual indications that recipients can inspect upon delivery, or they can be digitally recorded to the blockchain and verified in that manner, or both. The package can also utilize smart-contract technology (i.e. Ethereum, Hyperledger, or other smart-contract capability) to trigger actions based on these verification functions. In one example, the smart-contract may trigger notifications to the sender and/or the recipient if tampering becomes evident at any point in transit. These notifications may be initiated by the package (e.g., based on a wireless transmitter within the package) or by a device that scans or communicates with the package (e.g., an RFID reader that reads an RFID tag in the package). In another example, the smart-contract capabilities can rescind payment in the event of tampering or failure to verify package contents (i.e., payment in full is only delivered when the final package passes contents verification). This is achieved utilizing the aforementioned blockchain entries or sensors to verify that the contents are as intended, since the original contents are written to the blockchain at the moment of packaging and point of production using the manufacturer's private key to establish authenticity.

Package contents verification can include modular components, as well, such as utilizing the blockchain capability of the packaging to verify the source code contained on embedded electronics, chips, sensors, or processors within the package. In this example, both the mathematical one-way hashing functionality and the sensor-based verification are viable methods and can be used separately or in combination. This is especially useful in certain military, defense, intelligence, and corporate applications. Additional tamper-resistant capabilities can be delivered through this blockchain integration, ensuring that both the package and its contents are delivered exactly as they were intended. All of these verification capabilities can be achieved in multiple ways—including, but not limited to, one-way mathematical hashing functions, tamper-evident sensors, accelerometers, GPS, bluetooth, RFID tags, or other sensors, optical machine-readable codes or watermarks, physical tamper-evident and/or tamper resistant features. In some examples, these sensors and security features can be built into the package during the manufacturing and/or packaging processes. In other examples, they may be added to the package by a security, authentication, or cortication service as a label, tag, package, wrapping, or other indicator applied to, coupled to, and/or embedded in the package or the item.

Blockchain-enabled 3D printed packaging can also be utilized to enhance supply chain visibility, efficiency, and cross-border transport. In this example, blockchain-enabled 3D printed packaging can be used to track custody and movement of the package from origin to destination. For instance, each time the package changes hands the custodian of the package may be determined and recorded and/or each stop a package makes from point of origin to final destination may be determined and recorded. The custody and location of the package may be determined by, for example, scanning the package with a mobile device, scanner, RFID reader, or other device, or by sensors and transceivers within the package reporting the location and/or condition of the package wirelessly over a network. Handlers can be verified at each step, and any required cross-border information (customs declaration forms, etc.) can be embedded in an inalterable form at the point of origin and verified using the blockchain capability at one or more checkpoints (e.g., customs or border crossing locations, transfer stations, ports, airports, etc.). Additionally, any shipping fees, tariffs, or other associated costs can be enabled and fees paid automatically upon performance of the one or more triggering actions (e.g., performance of a contact term, movement of the package from one location to another, change of custody of the package, etc.) through smart contract capability built into the blockchain-enabled packaging. In this example, when the shipper authenticates the package at the point of pickup (e.g., by scanning a bar code, QR code, or other machine-readable code, receiving a radio frequency signal from an RFID tag or radio module in the package, optically scanning or capturing an image of the package itself, etc.), their payment for the shipping can be received in accordance with the agreed upon and predefined carrier agreement, which is represented in the package's blockchain-based dataset. Similarly, when the package crosses an international border and must pay a tariff, import tax, VAT, or similar, this payment may be automatically enacted at the point of crossing (e.g., responsive to authenticating the package using any of the techniques described herein or other techniques to uniquely identify the package or its contents), again in accordance with the predefined contractual capability on the blockchain. This increases efficiency, reduces likelihood of fraud or corruption, and allows both shippers and producers to negotiate based on better data sets and real-world tracking and interactions.

The foregoing and other examples are described further below with reference to the figures, which illustrate example architectures, devices, systems, and methods that may be used to implement the distributed manufacturing and/or blockchain enabled packaging techniques described herein.

Example Distributed Manufacturing Platform

FIG. 1 is a schematic diagram illustrating an example system 100 usable to implement distributed manufacturing techniques such as those described herein. As shown in FIG. 1, the system 100 includes multiple entities 102(1), 102(2), 102(3), 102(4), 102(5), 102(6), . . . 102(N) (collectively referred to herein as entities 102) which are in communication with a distributed manufacturing platform 104 (sometimes referred to simply as "the platform 104") and a data store 106 via one or more wired and/or wireless networks. By way of example and not limitation, the networks may comprise cable networks (e.g., cable television and/or internet networks), telephone networks (e.g., wired and/or cellular), satellite networks (e.g., satellite television networks), local area networks (e.g., Ethernet, wifi, Bluetooth, Zigbee, etc.), fiber optic networks, or any other network or networks capable of transmitting data between and among the entities 102, the platform 104, and/or the data store 106. The network(s) may be a collection of individual networks interconnected with each other and functioning as a single large network (e.g., the Internet or an intranet).

The entities 102 in this example are representative of parties that use and/or provide products or services via the distributed manufacturing platform 104. By way of example and not limitation each of the entities 102 may represent one or more designers, customers, printer owners, printer manufacturers, computer aided design (CAD) software companies, traditional manufacturers, shippers, post processing service providers, finishing service providers, assemblers, quality assurance services, certification services, e-commerce merchants, bricks and mortar merchants, fulfillment companies, payment companies, brokerage companies, rating/reputation services, or the like. Each entity 102 may fit a single role (e.g., customer) or multiple roles (e.g., an entity may be a printer owner, traditional manufacturer, and provide post processing, finishing, and assembly services). Each entity 102 in this example includes at least one computing device including one or more processors, memory, and one or more communication connections by which the computing device(s) of the respective entity communicate over the network.

The distributed manufacturing platform 104 in this example comprises a service hosted on one or more servers or other computing devices. The computing device(s) may be disposed at one or more enterprise locations, data centers, or other computing resources accessible via the network. In some examples, the platform 104 may be a web service accessed via an internet browser, distributed manufacturing client, or other application running on computing devices of the entities 102 accessing the platform. In other examples, as described with reference to FIG. 2, the platform 104 may be implemented using a distributed or peer-to-peer architecture. The platform 104 may be public (e.g., accessible to anyone with a network connection) or private (e.g., accessible only to members, employees of a certain company or organization, individuals or entities holding a security clearance, or individuals or entities meeting some other criteria).

In some examples, the platform 104 may simply provide an ecosystem or marketplace by which other entities 102 can interact. However, in some examples, the platform 104 may also serve any one or more of the roles discussed above for the entities (e.g., a merchant, marketplace for multiple merchants, printer owner, shipper, fulfillment service, payment service, etc.). Whether or not the platform 104 plays any of the other roles mention above, the platform 104 may be configured to match various entities based on, for example, the needs or requests of one entity, the capabilities of one or more other entities, and various other considerations (e.g., location, cost, availability, workload, etc.). The platform 104 may include one or more algorithms or machine learning models to implement the matching.

The data store 106 represents network accessible storage usable to store various data and information. By way of example and not limitation, the data store 106 may comprise a data store specific to the distributed manufacturing platform 104, a repository of product designs/models (e.g., Shapeways™, Turbosquid™, CG Trader™, Sculpteo™, 3D Warehouse™, SolidWorks™ CAD Library, etc.), a general purpose network storage service (e.g., Dropbox™, Box.net™, Google Drive™, One Drive™, etc.), or a combination thereof. While only one data store 106 is shown in FIG. 1, in practice any number of one or more data stores may be included in the system 100 and/or accessible via the platform 104. Additionally, while the data store 106 is shown as a separate service accessible via the network, in other examples, the data store 106 may additionally or alternatively be part of or associated with the platform 104 and/or one or more of the entities 102. The data store 106 may store one or more product specifications 108, part or item models 110, package models 112, and/or other data or information.

In some examples, product specifications 108 may include a description of features, characteristics, and requirements of a product that a customer desires to have designed and/or manufactured. In some examples, product specifications 108 may additionally or alternatively include engineering drawings, renderings, sketches, blue prints, material specifications, or other information related to the design and/or manufacture of the product.

Part or item models 110 may include computer generated drawings or models of individual parts, assemblies, and/or whole items or products. The item models 110 may include 2D and/or 3D models including, without limitation, computer aided design (CAD) files, computer aided engineering (CAE) files, computer aided manufacturing (CAM) files, machine code files such as computer numerical control (CNC) files, finite element analysis (FEA) files, or the like. A few types of 3D modeling that may be used include, without limitation, parametric modeling, direct or explicit modeling, freeform surface modeling, or the like. The files may be in any file format usable by the entities 102 or the platform 104.

Package models 112 include computer generated models of packaging for one or more 3D printed or traditionally manufactured items. The package models 112 may be designed by a designer or may be automatically generated based on an item model 110 or one or more scans or images of an item. Additional details of generation of a package model can be found in U.S. Pat. No. 9,248,611 (Divine et al.), which is incorporated herein by reference. The package models 112 can be generated using any of the software and may include any of the file formats described above with reference to the Item models 110.

In the illustrated example, one or more distributed ledgers 114 or blockchains may be used to record various transactions, execute smart contracts, and/or perform other operations conducted in relation to the distributed manufacturing platform 104. While a single common ledger 114 is shown in this example for simplicity, in some examples multiple different ledgers may be used in connection with the platform 104. For example, different ledgers may be used for different industries (e.g., a pharmaceutical ledger, an aerospace ledger, an automotive ledger, a medical device ledger, a consumer products ledger, a military ledger, etc.), different ledgers may be used for different industry groups, different ledgers may be used for different businesses or organizations (e.g., an ACME company ledger, a defense department ledger, etc.), different ledgers may be used for different roles (e.g., a customer ledger, a merchant ledger, a manufacturer ledger), and/or different ledgers may be used for different authorizations (e.g., memberships, permissions, security clearances, etc.). The ledger 114 may be public, private, permissioned, and/or secured as described in other locations of the application. In some examples, the distributed manufacturing platform 104 may be publicly accessible and may employ a common public ledger, while a subset of entities using the platform 104 may maintain one or more private ledgers to which transactions involving the subset of entities are written. In some examples, all transactions related to the distributed manufacturing platform 104 are recorded to the ledger 114, while in other examples, some transactions or some data associated with some transactions may be recorded off-chain.

In some examples, the creation of an item (e.g., the additive manufacturing process) may be captured digitally through photo or video evidence to demonstrate work performed, provenance, ensure that specific processes were followed, etc. These digital documentation assets can then be stored "off-chain" in common services such as YouTube, but recorded on the ledger or blockchain. A hash value for the digital asset can be created and written to the ledger, along with other related data (date, time, transaction identifier, related or relevant parties to that item, location of off-chain storage, etc.). The hash value allows anyone to confirm the authenticity of the digital documentation by simply re-hashing the asset wherever it may be stored. If the hash values match, then it can be ensured that not a single bit of the digital documentation has been altered. Data can include provenance of materials, condition of raw materials, manufacture methods and materials chosen or algorithmically determined, current equipment maintenance records, conformance to specifications and adjustments of equipment, operator information including certification for equipment, materials or designs.

In the illustrated example, the ledger 114 is stored and maintained by a subset of the actors. Specifically, in this example, the ledger is stored and maintained by entity 102(1), entity 102(5), entity 102(6), entity 102(N), platform 104, and data store 106. However, in other examples, the ledger 114 may be maintained by any number of one or more computing devices in communication with the system 100. In some examples, the ledger may be stored and maintained by computing devices regardless of whether or not they are members or users of the distributed manufacturing platform 104. For instance, in some examples, the ledger 114 may comprise an existing or general purpose distributed ledger (e.g., the ledger underlying bitcoin, Ethereum, hyperledger, etc.). In other examples the ledger 114 may be specific to the distributed manufacturing platform 104 and/or may be stored and maintained only by members or users of the distributed manufacturing platform 104.

In some examples, the ledger 114 may be omitted entirely and transactions conducted in relation to the distributed manufacturing platform 104 may be recorded using other techniques (e.g., traditional commerce and payment systems).

Figure 2:
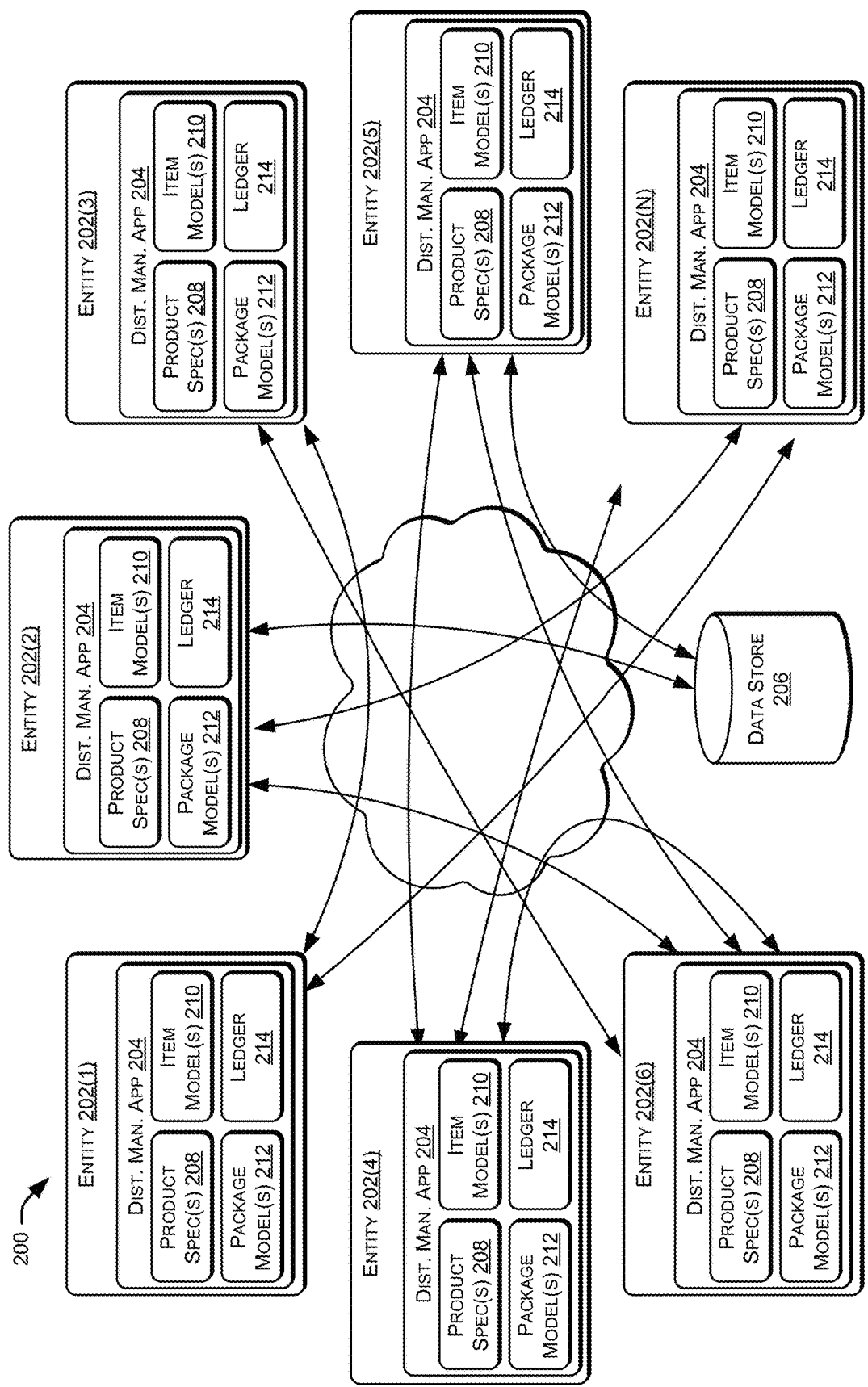
FIG. 2 is a schematic diagram of an example system for implementing decentralized distributed manufacturing techniques.

FIG. 2 is a schematic diagram illustrating another example system 200 usable to implement distributed manufacturing techniques such as those described herein. The system 200 of FIG. 2 illustrates a decentralized system in which multiple entities 202(1), 202(2), 202(3), 202(4), 202(5), 202(6), . . . 202(N) (collectively referred to herein as entities 202) are in communication with one another via a network. The network may include any of the types of networks described with reference to FIG. 1. In this example, some or all of the entities 202 have a distributed manufacturing application 204 installed on one or more computing devices at the respective entity. The distributed manufacturing application 204 may be stored in memory of the one or more computing devices at the respective entity and executable by one or more processors of the one or more computing devices at the respective entity. The distributed manufacturing application 204 includes one or more communication protocols for peer-to-peer file sharing ("P2P") that enable the distributed manufacturing techniques described herein. For example, the distributed manufacturing application 204 includes logic and interfaces usable by the entities 202 to distribute data and electronic files over the network. In some examples, the system 200 also includes a data store 206 similar to data store 106 which is accessible by the entities 202 via the network. Alternatively, separate data store 206 may be omitted and replaced with a decentralized data store in which some or all of the entities 202 and/or other computing devices accessible by the entities 202 allocate memory for storage of product specifications 208, item models 210, package models 212, and/or other data associated with distributed manufacturing. Such a decentralized data store may be implemented as part of the distributed manufacturing application 204 or other decentralized data storage protocol such as BitTorrent.

The distributed manufacturing application 204 may be configured to write to a distributed ledger 214 similar to the ledger described above with reference to FIG. 1. In some examples, the ledger 214 may be built into the distributed manufacturing application 204 (as illustrated), while in other examples the ledger 214 may be separate from the distributed manufacturing application 204 (e.g., as in the case where an existing ledger such as the bitcoin or Ethereum ledger is used).

In the decentralized example of FIG. 2, any number of entities 202 may be networked together to form the distributed manufacturing system 200. Moreover, the system 200 may include multiple separate ad hoc groups of entities which may be defined based on membership, role, industry, industry group, or any other criteria.

By increasing and distributing the number of entities in system 200, many additional functional advantages are provided. In a decentralized example such as system 200, the system benefits from additional redundancy due to the fact that each node is capable of contributing to the interactions of the overall system. If one or more nodes are inaccessible, the system is still operational. Moreover, the distribution of the ledger allows for transactions to be performed, written, read, and verified independently of the whole of the network. This capability ensures that any orders, payments, smart-contracts, or other interactions can continue with only the minimum necessary number of participating entities, ensuring not only redundancy capabilities, but also decreasing overhead costs as participants are not responsible for operating all entities on the network. In fact, in some examples, participants can be incentivized to operate entities (or nodes) on the network, verify transactions, store relevant entries on the ledger, store or transmit relevant data files, or otherwise engage in the transaction process—all of which increases the overall resiliency and capability of the system. Additionally, decentralized nodes may allow selection of "oracles" or data inputs from known operational and reliable data providers and stream, allow routing around compromised or hacked oracles, and provide choice of law and choice of data within choice of law jurisdictions agreed upon or determined by self-executing contracts reliant on nodes and data from nodes.

Figure 3:
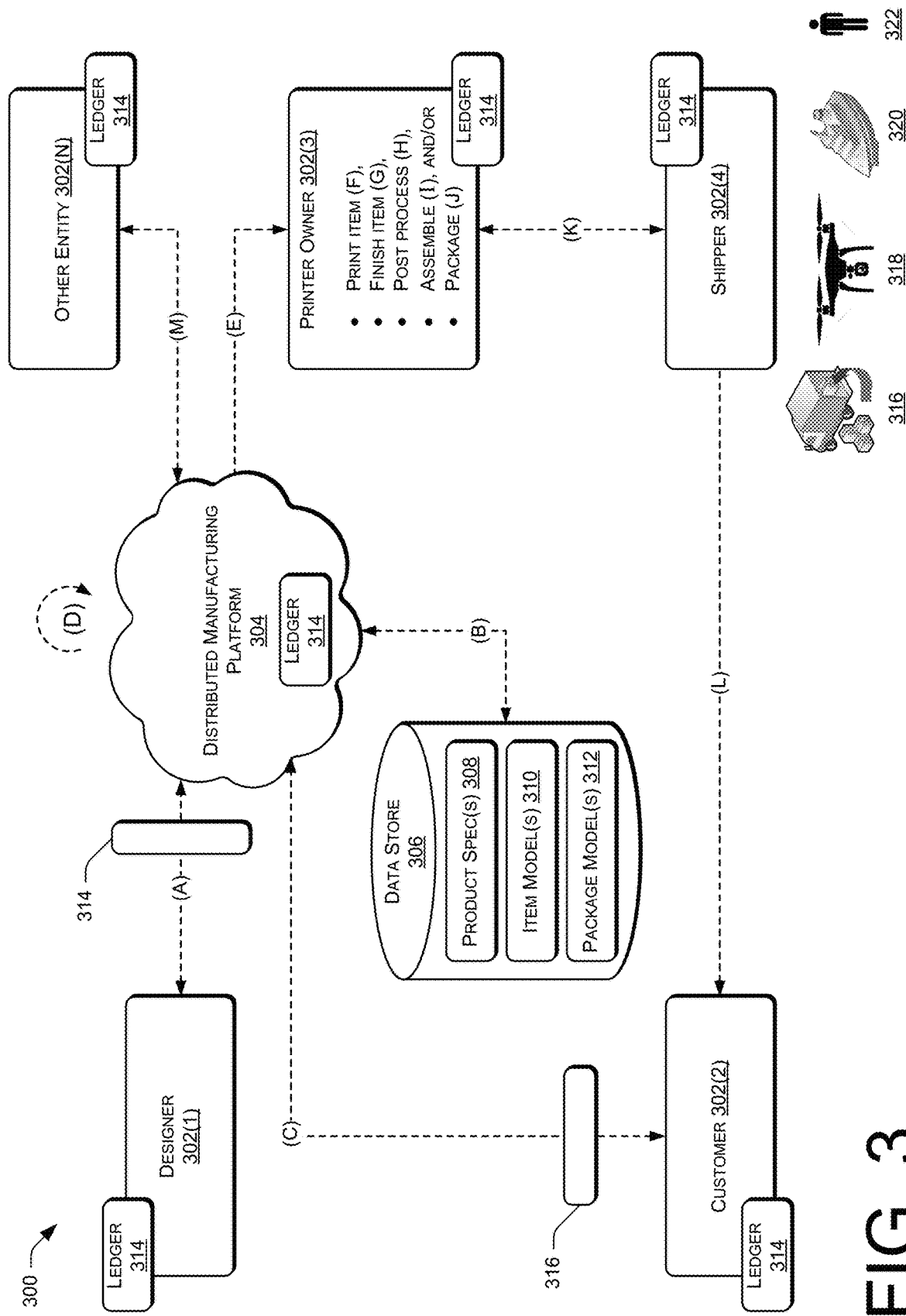
FIG. 3 is a schematic diagram illustrating an example operation of distributed manufacturing techniques.

FIG. 3 is a schematic diagram showing an example environment 300 illustrating an example operation of distributed manufacturing techniques. The example of FIG. 3 can be implemented using a centralized system such as that shown in FIG. 1 or a decentralized system such as that shown in FIG. 2, and may or may not make use of a distributed ledger. As shown, the environment 300 includes multiple entities 302, including a designer 302(1), a customer 302(2), a printer owner 302(3) or other manufacturer, a shipper 302(4), and one or more other entities 302(N), which are communicatively coupled to a distributed manufacturing platform 304 and a data store 306 via a network. The network may be any one or combination of the networks described herein. The one or more other entities 302(N) in this example can represent any one or more of makers of 3D printers or other automated manufacturing equipment, CAD software developers, post processing companies, finishing companies, assembly companies, quality assurance companies, e-commerce merchants or marketplaces of e-commerce merchants, fulfillment companies, payment processing companies, brokerage companies, rating/reputation services, security companies, and/or any other entities providing or using services related to product supply chain. The data store 306 in this example may store one or more product specifications 308, item models 310, and/or packaging models 312. The product specifications 308, item models 310, and/or packaging models 312 of this example may be the same or similar to those described with respect to the preceding examples. At least one, and in this example all, of the entities 302, the platform 304, and/or the data store 306 store and maintain one or more ledgers 314 as described throughout the application.

In one example operation, the platform 304 is configured to assist a designer 302(1) in bringing a new product to market. In such an example, the designer 302(1) designs product and at operation (A) uploads an item model 310 of the new product to the distributed manufacturing platform 304. In some examples, access to the distributed manufacturing platform 304 at operation (A) may be provided via an interface 314. The interface 314 may include one or more controls (e.g., buttons, menus, text entry fields, program calls, voice prompts, etc.) by which the designer 302(1) may be prompted (or given the option) to provide additional information about the item model 310. Unless otherwise specified, the term "interface" herein refers to a graphical user interface (GUI), a natural user interface (NUI), an application programming interface (API), or any other interface enabling human-to-machine or machine-to-machine communication. By way of example and not limitation, the additional information that may be provided by the designer 302(1) can include, among other things, an identifier of the item or item model, parts of which the item is composed, an assembly of which the item is a part, designer, a product specification of the item, a description of the item, images or renderings of the item, an owner of the design of the item (if not the designer), a patent number and/or copyright registration covering the item, license terms under which the item may be made, reproduced, used, sold, etc. In some examples, the item model 310 may additionally or alternatively include, or have appended to it, meta data such as a version number of software used to generate the item model 310, an owner or licensee of the software used to generate the item model 310, a timestamp (e.g., date of creation) of the item model 310, a location or identifier of a computing device from which the item model 310 was generated, or any other information related to the item model 310 and/or the designer 302(1).

At operation (B) the platform may process the item model 310 and store it in the data store 306. In some examples, processing the item model 310 may include compressing the item model 310, converting the item model 310 to one or more different file formats (e.g., file formats compatible with one or more 3D printers or other manufacturing equipment), encrypting the item model 310, applying digital rights management (DRM) protection to the item model 310, tagging the item model 310 with one or more keywords or other information (e.g., date of creation, the additional information provided by the designer 302(1), the meta data accompanying the item model 310, etc.), indexing the item model 310 in an item index, adding the item model 310 to an item catalog of items available via the distributed manufacturing platform 304 or another entity (e.g., a merchant or marketplace of merchants), and/or creating an item detail page for the item including a description, images, and/or details of the item.

At operation (C), the customer 302(2) logs on or otherwise accesses the platform 304 and places an order for a quantity of an item corresponding to the item model 310. In some examples, the customer 302(2) accesses the platform 304 via an interface 316. The interface 316 may include controls by which the designer 302(1) may be prompted (or given the option) to specify conditions or criteria associated with the order. By way of example and not limitation, the conditions or criteria about the order may include a quantity of the item desired, whether the customer is willing to accept less than all of the specified quantity, whether the quantity of the item must be supplied by a same manufacturer, a price the customer is willing to pay for each item or for the quantity of items, a delivery location of the items, a desired delivery date for the items, whether the customer is flexible on the delivery date of the items (e.g., in exchange for more favorable pricing), a preferred shipping mode for the items, whether the items must all be shipped together or can be shipped as they are made or otherwise become available, a relative priority of delivery speed vs. cost, and numerous other conditions and criteria.

In some examples, a common interface or set of interfaces may be used for all entities accessing or interacting with the platform 304. In that case, interface 316 may be the same as interface 314 and may include substantially the same set of controls and capabilities. However, in other examples, each entity may be provided with its own interface determined based upon the identity, role, or other characteristic of the entity and the interface may present only those controls and capabilities applicable to the particular entity or type of entity. For instance, the interface 316 provided to the customer 302(2) may be a customer interface and may be different than the interface 314 provided to the designer 302(1) which may be a designer interface, and may be different than the interfaces provided to other types of entities. Unless otherwise specified, the interfaces described herein may be common interfaces or may be determined based upon the identity, role, or other characteristic of the entity. While not shown, interfaces may also be provided the printer owner 302(3), the shipper 302(4), and the other entity(s) 302(N) to access, interact with, and transfer data to/from the platform 304.

At operation (D), the platform 304 selects (or recommends) the printer owner 302(3), from among multiple available printer owners (not shown in this figure), to print the item using a matching algorithm or machine learning model that matches product requirements and/or customer criteria with the capabilities of multiple possible printer owners. In some examples, the matching of entities may be performed autonomously by the platform 304. In some examples, the matching may be performed by one or more of the entities (e.g., the customer, designer, printer owners, shipper, a combination of these, or the like) with or without suggestions by the platform 304. In some examples, the matching may be performed interactively by allowing multiple entities to negotiate and/or bid on a job or transaction (e.g., multiple suitable printer owners may be identified and then allowed bid on which will print the quantity of items for the lowest price, or the customer may be allowed to select from among the multiple printer owners based on price, print capacity, location, delivery date, and/or other capabilities of the respective printer owners). Matching an order request to a production machine (e.g., 3D printer) may occur based on any number of factors or criteria, individually or in combination, including price, type of product or printer, availability, quality requirements, capabilities, reputation, shipping cost, security, etc. Location nearest the final destination may be weighed in making the printer selection decision so as to minimize costs, delay, environmental impact, etc. Additional matching criteria could be based on shipping cost, number of items ordered, activity level of required printers (i.e., how busy is the needed machine, how long before the printer is available, etc.), print materials, print resolution, or final quality. In a further example, a reverse-auction style selection system would allow printer owners, designers and/or shippers to bid on jobs. Other example criteria include a maximum distance from the final location, a minimum rating (e.g., job quality reputation) for the printer owner, a minimum quality level for the individual printer, etc. These and/or numerous other criteria may be used individually or in combination to match parties on the distributed manufacturing platform.

As mentioned, in some examples a matching algorithm may be used to match orders with printer owners or other manufacturers. In that case, some criteria may be binary (that is, they are either met or not by a particular manufacturing machine) while other criteria may be variable (that is, they can take on multiple values within a range). For example, a criterion specifying that an item be printed in a particular material is binary (a printer can either print in that material or not), while a criterion specifying a preference for low cost would be variable (since print cost is a value that can be calculated for a printer and may vary from printer to printer). When using a matching algorithm, digital logic can be used as a first stage to identify a pool of machines (printers and/or other manufacturing equipment) that meet the binary criteria specified. The output of the first stage is a pool of machines that meet the binary criteria. Then, in a second stage, a polynomial function can be generated with variables corresponding to each of the variable criteria. The function may include coefficients or weight factors that express the user's relative preferences for different criteria. For example, if a customer prioritizes price over speed, the coefficient on the price variable may be higher than the coefficient on the speed factor. The function can then be solved for each printer or other machine in the pool of machines by substituting the corresponding capabilities of the printer or other machine for the variables in the function. The output of the second stage can be a ranked list of printers or other machines output from the first stage. In some examples, the algorithms may match regulatory requirements and industry standards (strength or type of materials, qualities of materials, conductivity or non-conductivity, impact, shatter characteristics, protective factors, and others). Some examples may include quality indicators, for instance reliability, durability, planned obsolescence, usage cycles, heat tolerances, stress tolerances, impact tolerances, and other measures. Algorithms in some examples may prioritize designers for products, packages, brands (e.g., the brand of a component part of the item, the package, the colors, the inks, the materials, or other components). In some examples the material or printer origin, including import and export license permissibility may be factors in algorithms determining selection of printer, printer type, location, material, allowable designs, and other factors in law, regulation, trade, or external factors. In some cases the personnel qualifications of equipment operators or designers may be factors (e.g., in some defense use-cases, parts may have classified specifications or designs which might only be accessible with a security clearance).

In addition to or instead of using matching algorithm, in some examples the platform 304 may use a machine learning model to categorize orders and/or match orders with printer owners or other manufacturers. By way of example and not limitation, deep learning techniques, neural language models, convolutional neural networks, or other machine learning models may be used alone or in combination with one or more traditional classification approaches. The machine learning model may be trained offline using existing classified corpuses of data such as product catalogs and/or item detail pages of e-commerce merchant websites, repositories of labeled product designs/models (e.g., Shapeways™, Turbosquid™, CG Trader™, Sculpteo™, 3D Warehouse™, SolidWorks™ CAD Library, etc.), or the like. Additional details of how machine learning models can be applied to match item orders with capabilities of printer owners and other entities can be found in Ristoski et al., "A Machine Learning Approach for Product Matching and Categorization," Data and Web Science Group, University of Mannheim, B6, 26, 68159 Mannheim, Oct. 11, 2016.

In some examples, custom matching algorithms may be used that apply machine learning models to semi-structured data. The matching algorithms may be performed by the platform 304, or the platform may employ a third-party matching service. In some examples, one or more of the other entities 302(N) may comprise a matching service. In that case, the platform 304 may invoke the matching functionality of the matching service by, for example, calling an API of the matching service. One example third-party matching service that can be used is Sajari™, of Sydney Australia.

After selecting one or more printer owners or other manufacturers to produce the item, the process proceeds to operation (E) in which the platform 304 sends instructions to the selected manufacturer, in this case printer owner 302(3). In this example, printer owner 302(3) was selected during the matching process at least in part because it was able to perform multiple required operations at a single location. Specifically, in this example, the printer owner 302(3) is capable of not only printing the item, but also finishing the item (e.g., removing support structures, sanding, polishing, machining, etc.), post processing the item (e.g., priming, painting, plating, powder coating, heat treating, etc.), assembling the item (e.g., assembling the item from multiple disparate 3D printed and/or traditionally manufactured parts), and packaging the item in a 3D printed packaging and/or traditional package. Details of 3D printed packaging techniques can be found in U.S. Pat. No. 9,248,611 (Divine et al.), which is incorporated herein by reference. Thus, in this example, the printer owner 302(3) can, at operation (F) print the item, at operation (G) finish the item, at operation (H) post process the item, at operation (I) assembly the item from multiple parts, and at operation (J) package the item. In some examples, packaging the item may include printing a 3D printed package customized based on the item, the designer, the customer, the shipper, and/or other factors. The 3D printed package may be printed at least partially around the item, or the 3D printed package may be printed and the item may be may be inserted in the 3D printed package. Or in some examples, individual parts of the item may be packaged in unassembled form for transport to the designer, customer, or another entity (e.g., an assembler, a warehouse, etc.). In other examples, operations (G), (H), (I), and/or (J) can be performed by one or more other entities or may be omitted entirely.

At operation (K) the packaged item may be transferred to the shipper 302(4). In some examples, the shipper 302(4) may pick up packaged item from the printer owner 304(3), while in some examples the printer owner 302(3) may deliver the packaged item to the shipper 302(4), and in still other examples another delivery service (e.g., a local delivery service) may transfer the packaged item from the printer owner 302(3) to the shipper 302(4). The shipper 302(4) may load the packaged item onto a land vehicle 316 (e.g., car, truck, bus, train, etc.), aircraft 318 (airplane, helicopter, drone, etc.), watercraft 320 (e.g., ship, boat, barge, ferry, etc.), or couriers 322 (e.g., on foot or bicycle) for delivery to the customer 302(2). In some examples, the packaged item may be transferred from one vehicle/aircraft/watercraft/courier to another directly or via one or more transfer stations. Each time the packaged item is transferred, the location and/or custody of the package may be tracked and recorded to the ledger 314 (e.g., by sensors in the package and/or sensors at the transfer site). At operation (L) the shipper 302(4) delivers the packaged item to customer 302(2).

At operation (M), the one or more other entities 302(N) cause payment for the order to be transferred from the customer 302(2) to the designer 302(1), the printer owner 302(3), and/or the shipper 302(4). Operation (M) may cause transfer of payment as soon as the order is placed, upon delivery of the item to the customer, and/or at one or more intermediate times. For instance, in one example, a portion of the payment may be transferred to the designer 302(1) when the order is placed, a portion of the payment may be transferred to the printer owner 302(3) at the time the print instructions are sent to the printer owner or upon proof that the items have been printed, a portion of the payment may be transferred to the shipper 302(4) upon the item being placed in the shipper's custody, and additional portions of the payment may be transferred to the shipper 302(4) and the designer 302(1) upon successful delivery of the item to the customer 302(2) within the terms of the smart contract governing the transaction. In some examples, a portion of the payment may be transferred to the platform 304 at the time the order was placed, when the item is delivered to the customer, or at any other time in between the order and delivery. In some examples, one entity may choose to pay with one currency and another entity may choose to receive funds in another currency. In that case, the one or more other entities 302(N) may also provide currency conversion or brokerage services to trade one form of currency (e.g., fiat currency, crypto currency, tokens, credits, etc.) for another form of currency. These funds transfers, currency conversions, or other transactions may be accomplished automatically based on the smart contracts written to the ledger 314 at the time the order was placed.

In a variation of the previous example, the platform 304 may assist the customer 302(2) to locate one or more appropriate designers 302(1), to assist in the design of a new product for the customer 302(2). The customer 302(2) may submit a product specification 308 to the platform 304, which may be processed and uploaded to the data store 306. In this example, the platform 304 may match the product specification 308 with one or more designers by taking into consideration the job difficulty, designer skill level, designer pay level, designer specialty, designer reputation or rating, and/or other factors, and applying matching algorithms, machine learning models, or invoking a third-party matching service as described in the preceding example. The designer(s) 302(1) may create data file(s) appropriate for input to 3D printer(s) and/or other manufacturing equipment and may upload them to the data store 306 for review and approval by the customer 302(2). In other examples, the platform 304 may convert files uploaded by the designers 302(1) to data file(s) appropriate for input to 3D printer(s) and/or other manufacturing equipment. The platform 304 may also assist the customer 302(2) to locate one or more appropriate 3D printer owners 302(3) having one or more 3D printers or other machines to create an appropriate quantity of the product(s). The platform 304 may help the customer 302(2) to locate the 3D printer owners 302(3) based upon geographic location, print job cost, quality of output, printer or media characteristics, or other criteria. The platform 304 may help the customer 302(2) to print low volume from a small set of printers (e.g., one or more printers of a single printer owner), or higher volume in shorter time from a larger set of printers (e.g., multiple printers owned by multiple printer owners). The platform 304 may also arrange for one or more shippers 302(4) to move the product from the printer owners 302(3) to an end customer, which may or may not be the customer 302(2) that worked with the designers 302(1) and printer owner 302(3). The platform 304 in this example may handle aspects of bids provided by various designers, printer owners and/or shippers for the consideration of the customer. The platform 304 may handle aspects of quality assurance and testing of the printers associated with the platform. The platform 304 may handle aspects of the credentials and/or competency of the designers for various types of work. The platform may maintain customer feedback related to designer, printer and/or shipper skill, quality and/or timeliness. The platform 304 may handle, regulate, translate and/or manage the file types or data types that are used by various designers and/or printers. Thus, the platform 304 may assist designers and printer owners to increase their mutual compatibility, and to thereby help the customer to obtain more value from designers and broader choice of printers, while helping printer owners to maximize the utilization rates of their printers and thereby increase the return on investment on their printers.

Any or all of the operations (A)-(M) and other operations described with reference to FIG. 3 may be recorded in the distributed ledger 314 maintained at any one or more of the entities 302, platform 304, the data store 306, and/or other computing devices. Moreover, once manufactured, the location and/or custody of the item may be tracked by one or more sensors included in the package and/or one or more external scanners (e.g., scanners located at one or more checkpoints), and the location and/or custody may be transmitted to one or more of the entities 302, the platform 304, and/or the data store 306 where it can be written to the ledger 314.

Example Computing Device of Distributed Manufacturing Platform

Figure 4:
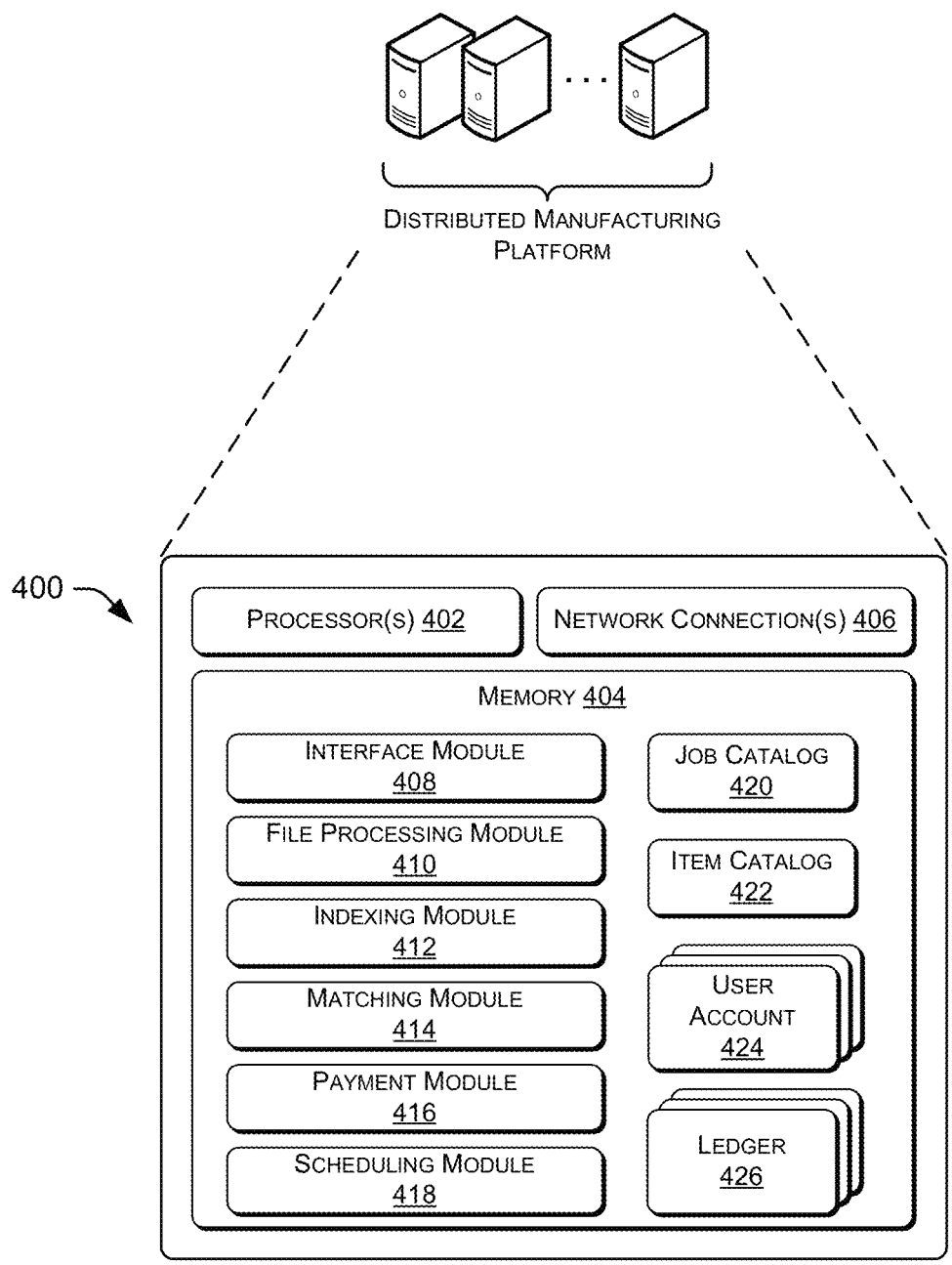
FIG. 4 is a schematic diagram illustrating an example computing device of a centralized distributed manufacturing platform.

FIG. 4 is a schematic diagram illustrating an example computing device 400 for use a distributed manufacturing platform. The distributed manufacturing platform may be composed of one or more of computing devices 400. The computing device 400 is a nonlimiting example of a computing device, one or more of which can, in some examples, be used to implement the distributed manufacturing platform 104 or the distributed manufacturing platform 304.

The computing device 400 comprises one or more processors 402 and memory 404. The processor(s) 402 may comprise one or more microprocessors (e.g., central processing units, graphics processing units, etc.), each having one or more processing cores, one or more microcontrollers, or other hardware capable of processing information and/or executing program instructions. The memory 404 may be configured to store one or more software and/or firmware modules, which are executable by the processor(s) 402 to implement various functions. While the modules are described herein as being software and/or firmware executable by one or more processors, in other embodiments, any or all of the modules or functional blocks may be implemented in whole or in part by hardware (e.g., as an application specific integrated circuit or "ASIC," a specialized processing unit, a field programmable gate array or "FPGA," etc.) to execute the described functions. The computing device 400 also includes one or more network connections 406 to connect the computing device 400 to one or more other computing devices via one or more networks. By way of example and not limitation, the network connections 406 may enable the computing device 400 to communicate with other computing devices of the distributed manufacturing platform, other computing devices within a system (e.g., entities 102, 202, 302 and/or data stores 106, 206, 306), as well as to one or more other local and/or wide area networks. In some examples, the network connections 406 may be configured to receive and relay communications between and among other entities via the one or more networks. Distributed manufacturing platforms according to this application may be implemented using one or more local computing resources (e.g., computers, servers, etc.) and/or remote (e.g., cloud-based resources). In some examples, distributed manufacturing platforms may be distributed across multiple local and/or remote computing resources.

As shown in FIG. 4, the memory 406 stores one or more applications or modules. In the illustrated example, the memory 406 includes an interface module 408, a file processing module 410, an indexing module 412, a matching module 414, a payment module 416, and a scheduling module 418. In other examples, fewer, additional, or alternative modules may be included. For instance, as will be described further below, the distributed manufacturing platform in this example includes modules that provide functionality (e.g., merchant services, payment services, etc.) that could be performed by one or more other entities, in which case corresponding modules could be omitted from the distributed manufacturing platform. Furthermore, additional modules corresponding to additional functionalities (e.g., manufacturing services, brokerage services, etc.) could be included in the event that the distributed manufacturing platform itself provides 3D printing or other manufacturing services.

The interface module 408 provides one or more interfaces (e.g., interfaces 314, 316, etc.) by which other entities can communicate with the distributed manufacturing platform. The interface module 408 may include one or more graphical user interfaces (GUIs), application programming interfaces (APIs), web interfaces, or other human-to-machine and/or machine-to-machine interface by which other entities can interact and/or communicate with the distributed manufacturing platform. In some examples, the interface module 408 may include a website or web portal through which entities can interact and/or communicate with the distributed manufacturing platform. For instance, the interface module 408 may serve web interfaces that enable the interactions described throughout the application.

The file processing module 410 receives files (e.g., item models, product specifications, photographs, drawings, renderings, marketing materials, etc.) from one or more entities and processes them for storage in a data store (e.g., data store 106, 206, 306, etc.) and/or transfer to one or more other entities. By way of example and not limitation, the file processing module 410 may include compression software to compress the files, file conversion software for converting the files to one or more different file formats (e.g., converting item models to file formats compatible with one or more 3D printers or other manufacturing equipment), encryption software to encrypt the files, and/or digital rights management (DRM) software to protect the files and/or limit their reproduction or distribution. In some examples, the file processing module 410 may additionally or alternatively include tagging software to analyze files and extract keywords, semantic meaning, meta data, or other information with which to tag the files or other files (e.g., a product specification for an item may be analyzed to extract keywords, description, and meta data with which to tag an associated item model). The file processing module 410 may also include package generation software configured to generate a package model for an item based on an item model for the respective item, a scan of the item, or other information. Then, when designer uploads an item model for a new item, the file processing module may generate a package model that can be used to manufacture (e.g., 3D print) a package for the respective item. The package model can then be tagged with an identifier of the item and/or stored in association with the item model. Additional details of generating a packaging model can be found in U.S. Pat. No. 9,248,611 (Divine et al.), which is incorporated herein by reference.

The indexing module 412 includes indexing software to index received files for ease of searching, matching, and presentation. For example, the indexing module 412 may index product specifications, manufacturing requirements, and other information provided by customers and add them to a job catalog 420 listing open jobs for which customers seek designers to design new products. As another example, the indexing module 412 may index item models and add them to an item catalog 422 of items available via the distributed manufacturing platform or another entity (e.g., a merchant or marketplace of merchants). As yet another example, the indexing module 412 may index item detail pages for an item including a description, images, and/or details of the item and store them in the item catalog 422 along with a corresponding item model for the item. The indexing module 412 may, in some examples, index the files based at least in part on the tagging and other processing performed by the file processing module 410.

Subsequently, when a designer searches or browses for a job, the matching module 414 matches the designer with one or more jobs in the job catalog 420. As mentioned above, this matching may take into consideration the job difficulty, designer skill level, designer pay level, designer specialty, designer reputation or rating, and/or other factors. Similarly, when a customer searches for an item, the matching module 414 identifies one or more items that match the search criteria. Once an order is placed, the matching module 414 also matches an order request to a production machine (e.g., 3D printer or other manufacturing equipment) based on factors or criteria, individually or in combination, including price, quantity of items ordered, type of product or printer, availability or activity level of required printers (i.e. how busy is the needed machine), print materials, quality requirements, capabilities, reputation, shipping cost, security, location, etc.

The payment module 416 transfers payment between the various parties each transaction according to the terms of the respective transaction. In some examples, entities or individual users of the distributed manufacturing platform may have user accounts 424. The user accounts 424 may include data regarding users that have registered with the distributed manufacturing platform, such as customers, designers, manufacturers, merchants, shippers, payment services, reviewers, or other entities. The user accounts 424 may include names, login credentials (e.g., user name, password, security questions, tokens, or other credentials), contact information (e.g., email addresses, phone numbers, mailing addresses, etc.), demographic information (e.g., age, gender, etc.), financial credentials (e.g., credit cards, bank accounts, etc.), birth dates, preferences, purchase history, return history, browsing history, user recommendations, medical history, drug allergies, prescriptions, or any other information reasonably related to the operations of the distributed manufacturing platform. When a customer places an order (or some time thereafter), the payment module 416 may transfer payment from a financial account of the customer to financial accounts of the distributed manufacturing platform and one or more designers, manufacturers, shippers, and/or other entities, based upon the services used to fulfill the order and the terms of the purchase transaction.

Once an order is placed, the scheduling module 418 may transmit instructions and/or files to one or more manufacturers, shippers, and/or other entities that are to perform operations associated with fulfilling the order (e.g., designing the item, manufacturing a specified quantity of items, finishing the items, post processing the items, assembling the items, shipping the items, etc.).

The computing device 400 may record details of any or all of the operations it performs, transactions that are performed using the distributed manufacturing platform, and/or instructions that it sends to other entities in one or more ledgers 426. The distributed manufacturing platform may maintain a single common ledger or multiple separate ledgers for different entities, industries, industry groups, organizations, permissions, or other groups as described in greater detail in other locations.

In an example operation, a customer may browse or search the distributed manufacturing platform via the interface module 408 for a product, the matching module 414 may identify one or more items from the item catalog 420 that match the search query or browsing category, and the interface module 408 may serve one or more item detail pages corresponding to the items from the item catalog 420. The customer may then select an item to order, and the scheduling module 418 may send instructions and files to a manufacturer to have the item manufactured and to a shipper to pick up the item from the manufacturer at a future date and time and deliver it to the customer. The payment module 416 may transfer funds from the customer to the distributed manufacturing platform, the manufacturer, and the shipper at times and in amounts according to terms of the purchase. In some examples, these terms may be predefined by the distributed manufacturing platform, while in other examples the terms may be negotiated by the parties to the transaction and may be recorded in a smart contract at the time the order is placed.

Example Computing Device of an Entity

Figure 5:
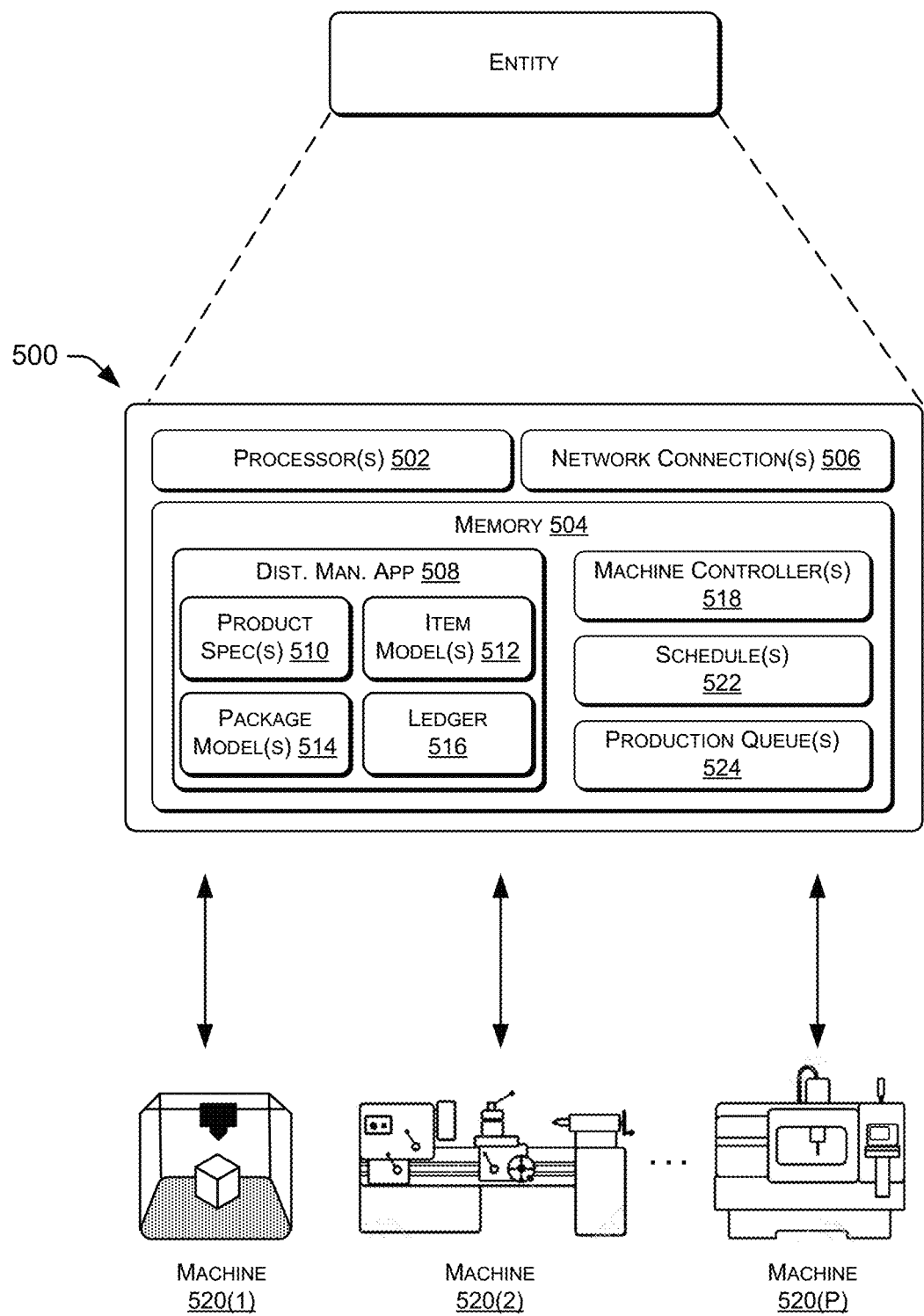
FIG. 5 is a schematic diagram illustrating an example computing device of an entity usable to implement distributed manufacturing techniques.

FIG. 5 is a schematic diagram illustrating an example computing device 500 of an entity, such as a designer, manufacturer, customer, shipper, or other entity. In this example, the computing device 500 is illustrated as a computing device of an entity in a decentralized distributed manufacturing system such as that shown in FIG. 2.

The computing device 500 comprises one or more processors 502, memory 504, and network connections 506, which may function the same as or similar to the corresponding components described with reference to the computing device 400 of FIG. 4.

As shown in FIG. 5, the memory 506 stores one or more applications or modules. In the illustrated example, the memory 506 includes a distributed manufacturing application 508, which may be the same as or similar to the distributed manufacturing application 204 described with reference to FIG. 2. Thus, the distributed manufacturing application 508 may include one or more communication protocols for peer-to-peer file sharing ("P2P") and logic and interfaces usable to distribute data and electronic files over the network to one or more other entities. The distributed manufacturing application 508 in this example also implements a distributed data store and includes or is associated with memory for storage of product specifications 510, item models 512, package models 514, and/or other data associated with distributed manufacturing. The distributed manufacturing application 508 may be configured to write to a distributed ledger 516, which may be built into the distributed manufacturing application 508 (as illustrated), or may be separate from the distributed manufacturing application 508 (e.g., as in the case where an existing ledger such as the bitcoin or Ethereum ledger is used).

The foregoing elements of computing device 500 are representative of any entity in a decentralized distributed manufacturing system such as that shown in FIG. 2. In the case of a system including a centralized distributed manufacturing platform such as that shown in FIG. 1, the distributed manufacturing application 508 may be omitted. However, computing devices of certain types of entities may have additional or alternative hardware and/or software components.

The computing device 500 shown in this example includes additional hardware and software components corresponding to a manufacturing entity, such as printer owner 302(3) in FIG. 3. Specifically, memory 504 of the computing device 500 includes one or more machine controllers 518 configured to control one or more machines 520(1), 520(2), . . . 520(P) (collectively "machines 520"), where P is any integer greater than or equal to 1. In the illustrated example, machine 520(1) corresponds to a 3D printer, machine 520(2) corresponds to a computer controlled lathe, and machine 520(P) corresponds to a CNC mill. However, in other examples, the machines 520 may include any type of additive or traditional manufacturing machines including, without limitation, machines for molding (e.g., injection molding, blow molding, blow fill seal, etc.), casting (e.g., sand casting, investment casting, etc.), machining (e.g., milling, turning, drilling, etc.), forming (e.g., shearing, stamping, punching, etc.), joining (e.g., welding, brazing, soldering, etc.), finishing operations (e.g., deburring, sanding, polishing, knurling, sand blasting, etc.), post processing (e.g., annealing, quenching, cryogenically freezing, painting, powder coating, plating, etc.), and the like. Further, the machines 520 may include a single machine, multiple instances of the same type of machine, multiple instances of multiple different types of machines. The machine controllers 518 may be communicatively coupled to the machines 520 via the network connections 506. While the machine controller(s) 518 are illustrated a single software or firmware module stored in the memory 504, in other examples, multiple separate machine controllers 518 may be used (e.g., one machine controller for each machine, or one machine controller for each type of machine) and/or the machine controllers 518 may be implemented as hardware controllers (e.g., micro controllers) that are part of the computing device 500 and/or the respective machines 520.

Memory 504 of the computing device 500 also includes one or more schedules 522, production queues 524, and other modules 526. The schedule(s) 522 define the amount of machine availability that the manufacturer is willing to make available for use by the distributed manufacturing techniques. For instance, if on average the manufacturer currently uses a particular machine 60% of the time and the machine remains unused the remaining 40% of the time, the manufacturer may update the schedule 522 to show that the machine is available 67.2 hours per week (i.e., 40% of the 168 hours in the week). The schedule 522 may define the machine availability in numerous different ways. In some examples, the schedule 522 may be in calendar form indicating the hours in which a particular machine is available. In other examples, the schedule 522 may set an absolute amount of machine time that the machine is available (e.g., 40 hours, 10 days, etc.), a rate of machine time availability (e.g., 4 hours per day, 3 days per week, etc.), a percentage of availability (e.g., 20% of the machine time is available), etc. Separate schedules 522 may be used for each machine, or a single schedule may be used for all machines that the manufacturer operates or designates for use with the distributed manufacturing techniques.

The production queue(s) 524 include jobs that are currently in progress. The production queue(s) 524 may define the time required to manufacture a quantity of an item. The time required may be a function of, for example, the quantity of the item, an item model 512 of the item, a package model 514 for a package for the item, or the like. Separate queues 524 may be used for each machine, or a single queue may be used for all machines that the manufacturer operates or designates for use with the distributed manufacturing techniques.

The schedule(s) 522 and/or the queues 524 may be published, transmitted, or otherwise provided to a distributed manufacturing platform (in the case of a centralized distributed manufacturing system) and/or one or more other participating entities (in the case of a decentralized distributed manufacturing system) for use in matching the manufacturer's machines to new manufacturing jobs.

Computer-Readable Media

The data stores 106, 206, and 306, and memory 404, 504, and any other memory discussed herein are examples of computer-readable media and may take the form of volatile memory, such as random access memory (RAM) and/or non-volatile memory, such as read only memory (ROM) or flash RAM. Computer-readable media includes volatile and non-volatile, removable and non-removable media implemented in any method or technology for storage of information such as computer-readable instructions, data structures, program modules, or other data for execution by one or more processors or circuits of a computing device. Examples of computer-readable media include, but are not limited to, phase change memory (PRAM), static random-access memory (SRAM), dynamic random-access memory (DRAM), other types of random access memory (RAM), read-only memory (ROM), electrically erasable programmable read-only memory (EEPROM), flash memory or other memory technology, compact disk read-only memory (CD-ROM), digital versatile disks (DVD) or other optical storage, magnetic cassettes, magnetic tape, magnetic disk storage or other magnetic storage devices, or any other non-transitory medium that can be used to store information for access by a computing device. As defined herein, computer-readable media does not include transitory media such as modulated data signals or carrier waves.

Example Blockchain-Enabled Packaging—Pharmaceutical Use Cases

Figure 6:
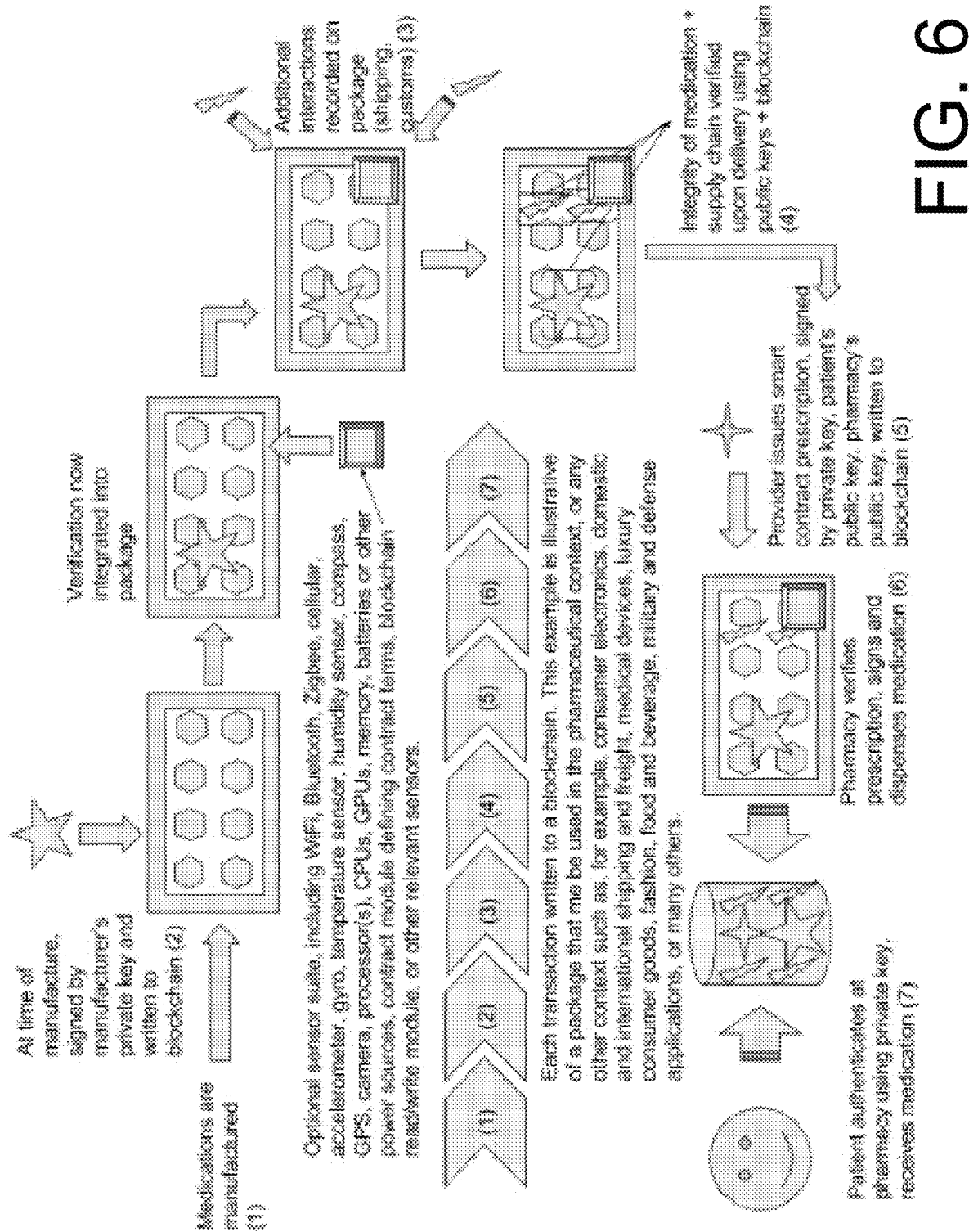
FIG. 6 is a schematic diagram illustrating an example of blockchain enabled packaging in the context of a pharmaceutical product.

FIG. 6 illustrates an example of blockchain enabled packaging in the context of a pharmaceutical product. However, the techniques described with reference to FIG. 6 are also applicable to other products. As shown in FIG. 6 one or more products or items, pharmaceuticals in this example, are packaged utilizing blockchain-enabled 3D printed packaging. In some cases, these may be traditionally manufactured pharmaceuticals that simply utilize blockchain-enabled 3D printed packaging. In other cases, the pharmaceuticals themselves may additionally or alternatively be customized to the consumer and created through an additive manufacturing process.

Individuals for whom the medication is prescribed can then use their own secret-key or other blockchain-based authentication mechanism to pick up the prescription. The nature of blockchain's structure and the underlying public-key encryption model means that an entry on the on the blockchain can be made for any individual using their public key, but authenticated only by the individual in possession of the corresponding private key. Conversely, the private keys of the prescribing physician and the issuing pharmacy can be incorporated to ensure that app components of the transaction are authorized. This authorization can come in several forms. In one instance, a visual code such as a bar code, Quick Response (QR) code, watermark, or other identifier can be displayed on the prescription packaging which can be verified by a scan performed by a mobile device (phone, tablet, point of sale terminal, etc.) containing the private key of the patient, pharmacy, etc. In another example, the public/private key pairs can be exchanged using Near Field Communication (NFC) or a Radio Frequency Identification (RFID) chip. This can be incorporated directly into the packaging, as well as a device (phone, tablet, point of sale terminal, token, etc.) possessed or used by the patient. Other sensors, chips, or data repositories can be integrated within the packaging to provide blockchain transaction and integration capability, including WiFi, Bluetooth, cellular radio, ZigBee, or other communications sensors. An additional suite of sensors, chips, and/or modules can provide relevant data repositories about the package by writing their data to the same blockchain—including, but not limited to, accelerometer, gyro, temperature sensor, humidity sensor, compass, GPS, camera, processor(s), CPUs, GPUs, memory, batteries or other power sources, contract module defining contract terms, blockchain read/write module, etc. These transactions can be written to a verifiable blockchain—public, private, secure, or some hybrid therein—where patients, providers, pharmacies, regulators, insurance companies, regulatory bodies, and other stakeholders can communally verify transactions and ensure that all parties in each transaction are interacting appropriately. Relevant data can be either embedded directly into the relevant blockchain, or linked to transactions and individual parties and verified through related sidechains or other blockchain-derived structures that provide a pre-computed hash value of the data, otherwise known as providing "proof of existence." These interactions can be mediated by predetermined contractual negotiations which can also be represented on the relevant blockchain (described with reference in FIG. 7, which illustrates movement of the smart package from manufacture, through transit, to delivery to a customer or patient).

In some examples, smart-contract technology can automatically enable payment at the time of purchase, or some compliance-based payment mechanisms can be pre-written into the contract (i.e. the consumer pays the full price of the prescription if they do not comply with the prescribed dosing regimen, or receives incentive payments based on short- or long-term compliance). This smart-contract capability can further be expanded by creating a compliance-based cost model for prescription drug coverages, whereby the blockchain-enabled packaging creates verifiable logs detailing which individual consumed which medication at which time. By writing this data to an accessible blockchain, providers will be able to track progress, caregivers who are not co-located with the patient (such as parents, adult children, or other guardians) can be notified in the case of a missed dose, and insurance companies can create incentives for compliance that can be easily, automatically, digitally, and irrefutably verified.

One application of this technology serves older Americans who utilize Medicare and Medicaid as their primary insurance. Blockchain-enabled packaging will allow Medicare and Medicaid—the largest user groups of prescription drugs in this country—to reduce costs and improve outcomes. A private Medicare and Medicaid blockchain may be created where transactions between patients, providers, and pharmacies are recorded. This data may include which patients receive which medication at which pharmacy from which provider, as well as which patients are compliant with their prescribed medication regimen, as well additional data such as cost, insurance-related information, and other data. This verifiable record—enabled only by the fact that the medication itself is delivered in a blockchain-enabled package—create clear, verifiable, and auditable data visibility into the entire supply chain for this particular customer pool. Each medication-related transaction will be recorded on this blockchain, including when the medication is prescribed, when and where the prescription is filled, who picked up the prescription, how much the prescription cost, and/or when each individual dose of medication is dispensed—all based on interactions with the packaging containing the medication. When this data is made readily available for their entire subscriber pool, Medicare and Medicaid can negotiate even more favorable prices from drug manufacturers, increase the efficacy of existing prescriptions, and improve outcomes through better compliance monitoring, earlier intervention, and prevention of negative drug interactions. In other examples, the same approach—a shared, centralized, blockchain-based, solution where transactions between patients, providers, and facilities are recorded—can apply to any segment or group of payers, providers, hospital systems, state agencies, etc. including private insurance companies, a group of private insurance companies, or other third-party entity, to which one or more government agencies, insurance companies, medical providers (e.g., hospitals, clinics, pharmacies, doctors, etc.), pharmaceutical companies, or medical device manufacturers may be subscribers or users.

Another example of blockchain-enabled packaging technology in a pharmaceutical application lies in preventing fraud, waste, and abuse. In one case, blockchain-enabled packaging can be used to verify the authenticity of the medication, including date and location of manufacture, each step in the supply chain from production to end-use, and incorporate anti-tampering, and anti-theft mechanisms. In one example, each dose of medication can be signed by the manufacturer's "private key" when it is produced, and this information is written to an accessible blockchain. This signature can then be verified utilizing the corresponding public key to verify that the medication is authentic and the transaction is valid. This verification can happen at any point in the lifecycle of the medication, including the manufacturing process, shipping or storage, delivery to a pharmacy, or delivery to a final customer. Verification can take place by scanning a Quick Response code embedded in the packaging utilizing a mobile device (phone, tablet, etc.), or by verifying the data through an embedded chip, sensor, or processor. Verification can be achieved utilizing embedded Near Field Communications (NFC) or Radio Frequency Identification (RFID), as well as other networked sensors and data storage capabilities.

Figure 8:
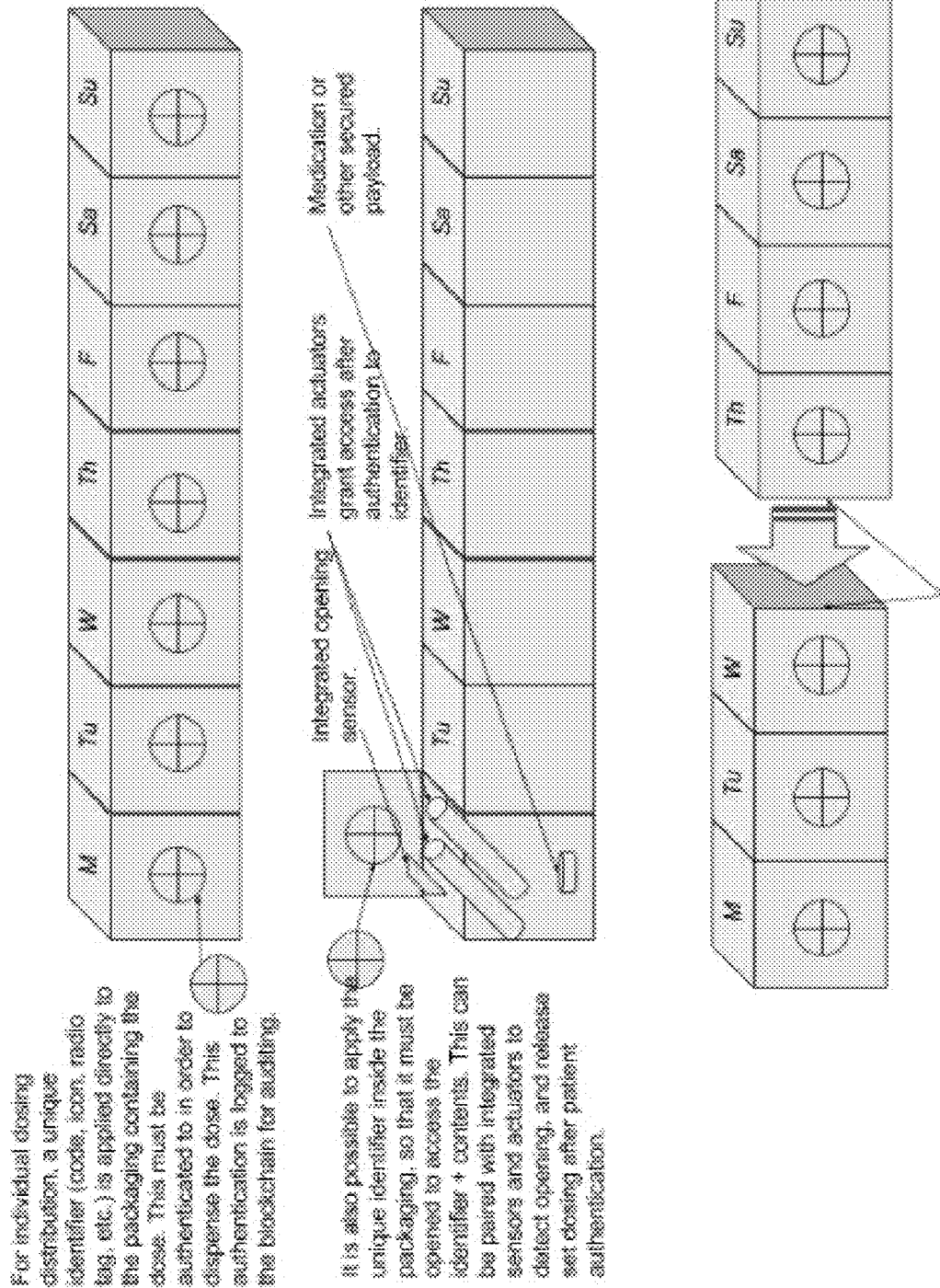
FIG. 8 is a schematic diagram illustrating an example 3D printed package with blockchain capability usable to control access to a product such as medication.

In another example, shown in FIG. 8, 3D printed packaging with blockchain capability offers access control to prescribed medication. The medication is packaged in predosed increments (similar to existing "day of the week" pill containers), but access is granted to each dose in accordance with the prescription parameters (which are pre-written into the packaging utilizing smart-contract technology). In one example, the package contains individually dosed medications that can only be accessed after the appropriate amount of time has elapsed since the previous dose was dispensed (i.e., every for medication to be taken every 4-6 hours) or at a scheduled dispensing time (e.g., 8 µm each day). This may achieved by a combination of blockchain capability to verify the previous transactions (i.e., what the prescribed dosing information is) as well as the timestamp of the previous dose. As each dose is packaged individually, additional doses are released on this verified time schedule, allowing the patient to access the individual container. This release can be accomplished utilizing an actuator, lock, tabbed hinge, or other self-enforcing security mechanism. In another example, all doses are stored in a single compartment (similar to existing pill bottles) with a dispensing mechanism located at the top or bottom of the compartment. This mechanism requires user input to activate (i.e., by pushing a button or lever, turning a knob, adjusting the orientation of the lid or other component of the mechanism, etc.) but the dispenser will only permit additional dosing in accordance in combination with such input and the blockchain-verified time-based information. In yet another example, applicable for particularly powerful or potentially addictive medications, the dispensing mechanism has a time-based verification as listed above, either in an aggregate compartment or individualized compartments, but must also verify the presence of the individual to whom the medication is prescribed. Blockchain-enabled packaging facilitates this by requiring the private key of the individual to be authenticated against before issuing the medication, provided the above conditions are already met (time, prescribed dosages, etc.). This authentication can take place utilizing a cryptographic token stored in a smartphone or tablet, individual token on a keychain, or utilizing biometric capabilities such as a fingerprint scan, retina scan, or similar. Because of the flexibility of the public/private key pairing underlying the blockchain technology, the key can be represented in many forms, and authenticated against many mechanisms, provided the underlying cryptographic validations can be performed.

For medication likely to be abused, such as opioids, blockchain-enabled packaging can notify providers if the same individual is attempting to fill prescriptions at multiple pharmacies, or if the individual is accessing medication at a rate that exceeds the prescription (which may indicate abuse by the individual, that the individual is selling the medication on the black market, or that an unauthorized individual is accessing the medication). It may also indicate that the dosage or even the medication itself is not an appropriate choice for the patient's needs, and the provider can revisit their decision with or without the patient. Blockchain-enabled 3D printed packaging can also allow regulatory bodies to identify providers who may be over-prescribing certain medications, or facilitating abuse, by tracking usage of both the provider and their patients with regards to abuse-prone medication.

This blockchain-based monitoring capability can also extend to the disposal of unused medication (such as painkillers prescribed after a surgery that can be taken "if needed" by the patient). If unused, the medication can be logged back into a pharmacy or other public locale where they can be destroyed, thereby tracking the entire lifecycle of the medication from production to destruction. Particularly in the case of opioids, this ability to ensure unused medications are properly disposed of—and not simply flushed down the toilet, forgotten about, or worse—stolen and abused—represents a significant improvement in a public health crisis that continues to grow. Furthermore, if the individual doses of the medication are packaged in 3D printed packaging that creates a reusable environment, these medications—which can be expensive to produce and procure—can be re-used without any concern for their quality, contents, or potency. For instance, if a patient does not need to use all of a medication, the patient may return the unused medication (e.g., by hand delivering or shipping the package) to a pharmacy, medical provider in exchange for a refund. If the unused medication was not accessed by the patient, was maintained within acceptable environmental conditions (e.g., temperature, humidity, inertial forces, etc.), is within its usable life (i.e., not expired), has not been tampered with, and is otherwise in usable condition as indicated by the package sensors, then the unused medication may be dispensed to another patient (with or without being repackaged). In addition to the reduction in risk posed by unused medication, the potential for reduction in cost by being able to re-use certain medications cannot be underestimated. An example of this can be seen in the deployment of blockchain-enabled technology in a Veteran's Administration (VA) Hospital.

In this example, providers gain the ability to set dosing regimes that will assure distribution of the right meds at the right time without intervention of a nurse to dispense individual dosage cups with the potential for errors or missed doses. The dosages, as well as the medications, intended patient name and location, frequency, etc. are all written to the blockchain utilizing a smart-contract capability. Each interaction (i.e. medication is dispensed, medication is delivered, medication is taken) can be written to the blockchain for verification, audit capability, and to trigger additional smart-contract terms (i.e. no additional medication for a set amount of hours, an additional dose must be taken with a set amount of hours, etc.).

In a similar military example, medical personnel in the field can utilize the same smart-contract and blockchain-enabled packaging to distribute non-medication items (i.e., performance enhancers, recovery drinks, electrolyte tabs, etc.) with the ability to re-prescribe or re-allocate unused items within a unit or a hospital or field hospital. Because each item is packaged in a blockchain-enabled package, it allows for tracking, verification of status and effectiveness, and logging of reissue. The ability to reallocate items between peers (i.e. between soldiers in the same unit) can also be enabled by allowing them to authenticate to the packaging of the exchanged items, capturing the interaction on the blockchain. This data can then be used to drive re-supply orders, inform medical decisions (i.e. this soldier took this substance at this time in the field), etc.

In another example, individuals maintain their own health information on a verified blockchain that allows medical providers, including doctors and pharmacists, to consult the relevant portions of the patient's electronic medical records prior to issuing a prescription. This information might include the patient's current medication (doses, frequency, duration, etc.), allergies (to food, medications, etc.), insurance coverage (provider, cost, status, co-pay, policy on generic pharmaceuticals, etc.), prior diagnoses (including both physical and mental health), etc. This will allow physicians and pharmacists to prevent potentially adverse drug interactions, particularly when an individual patient has multiple providers or health systems whose electronic medical records may not be fully compatible in real-time.

The ability to share verified data based on blockchain-enabled packaging can also significantly improve outcomes through remote telemedicine, increased family/guardian notification, and richer data to determine fatal errors. Deploying blockchain-capable packaging allows the pharmaceutical industry to access a massive amount of data about effectiveness at a scale never before possible. Furthermore, because the data can be both verified and anonymized, the ability to do large-scale, longitudinal studies increases exponentially. This could have a massive impact on public health with regards to potential superbugs and antibiotic behaviors, long-term diseases that require ongoing medication regimens, or other data that can unlock knowledge that's simply not possible today. Blockchain-enabled packaging can allow individuals to opt-in to being a "data donor," similar to the way many choose to be "organ donors" today when they renew their driver's license.

Figure 7:
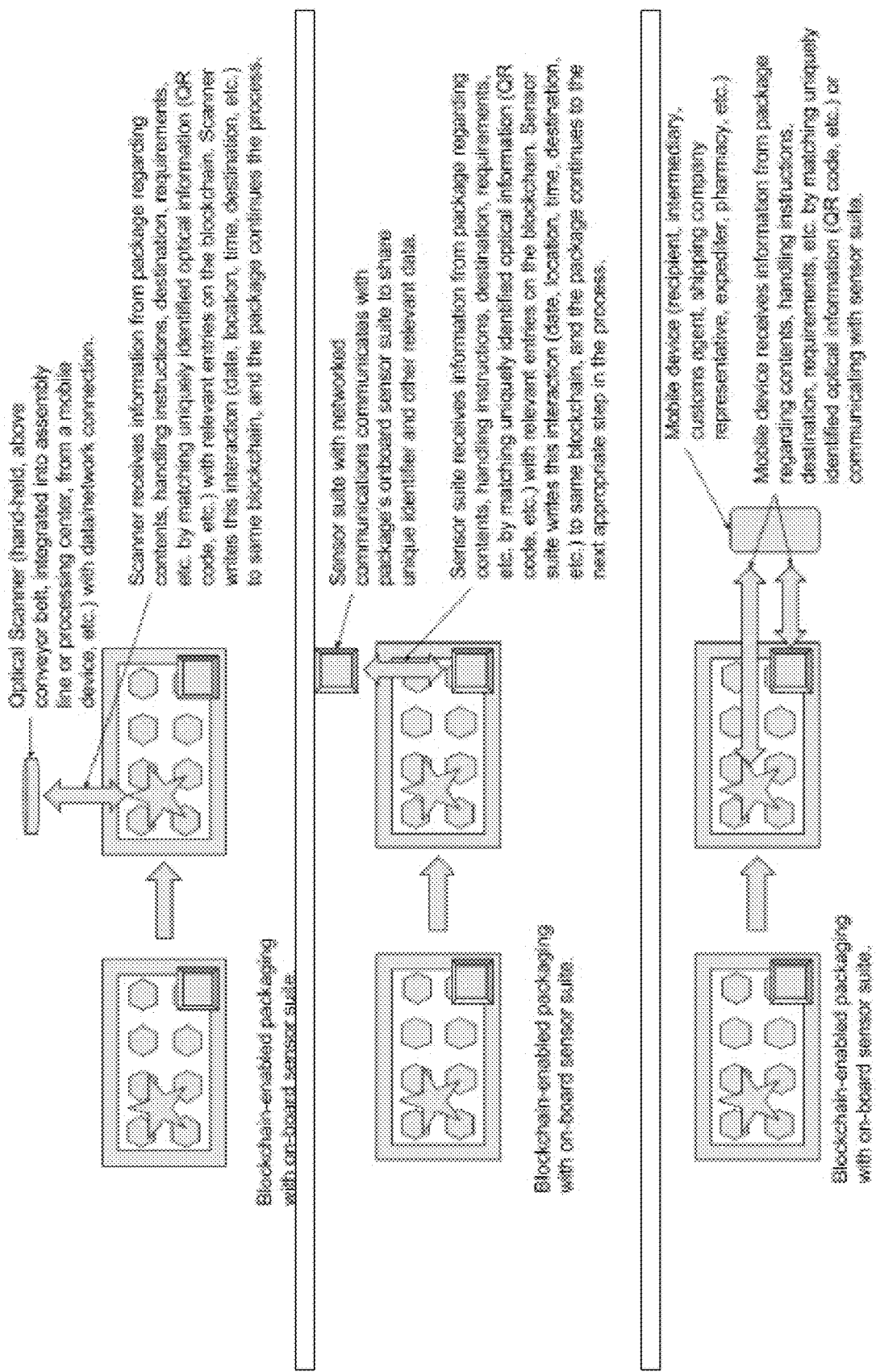
FIG. 7 is a schematic diagram illustrating movement of the blockchain enabled package of FIG. 6 through the supply chain.

In another example, as shown at the top of FIG. 7, the contents of a package are verified at the point of production and moment of packaging. Verification of package contents include a range of options—including both number and type of items, but also verification within the items contained. For example, pharmaceutical packages can be verified in terms of authenticity, quantity, and dosage, to prevent fraud, misrepresentation, or substitution for counterfeits during shipment, transport, or storage. Verification of package contents can be accomplished in multiple ways. In one example, contents are verified by a one-way mathematical hashing function, which results in a unique and verifiable output that is written to the blockchain. In another example, verification can be done with integrated sensors that indicate changes or tampering to the package. These indications can be visual indications that recipients can inspect upon delivery, or they can be digitally recorded to the blockchain and verified in that manner, or both. The package can also utilize smart-contract technology (i.e. Ethereum, Hyperledger, or other smart-contract capability) to trigger actions based on these verification functions. In one example, the smart-contract will trigger notifications to both the sender and the recipient if tampering becomes evident at any point in transit. In another example, the smart-contract capabilities can rescind payment in the event of tampering or failure to verify package contents (i.e. payment in full is only delivered when the final package passes contents verification). This is achieved utilizing the aforementioned blockchain entries or sensors to verify that the contents are as intended, since the original contents are written to the blockchain at the moment of packaging and point of production using the manufacturer's private key to establish authenticity.

Package contents verification can include modular components, as well, such as utilizing the blockchain capability of the packaging to verify the source code contained on embedded electronics, chips, sensors, or processors within the package. In this example, both the mathematical one-way hashing functionality and the sensor-based verification are viable methods. This is especially useful in certain military, defense, intelligence, and corporate applications. Additional tamper-resistant capabilities can be delivered through this blockchain integration, ensuring that both the package and its contents are delivered exactly as they were intended. All of these verification capabilities can be achieved in multiple ways—including, but not limited to, one-way mathematical hashing functions, tamper-evident sensors, accelerometers, GPS, bluetooth, RFID tags, or other sensors, optical machine-readable codes or watermarks, physical tamper-evident and/or tamper resistant features. In some examples, these sensors and security features can be built into the package during the manufacturing and/or packaging processes.

Blockchain-enabled 3D printed packaging can also be utilized to enhance supply chain visibility, efficiency, and cross-border transport. As shown in the middle and bottom sections of FIG. 7, blockchain-enabled 3D printed packaging can be used to track each stop a package makes from point of origin to final destination. Handlers can be verified at each step, and any required cross-border information (customs declaration forms, etc.) can be embedded in an inalterable form at the point of origin and verified using the blockchain capability. Additionally, any shipping fees, tariffs, or other associated costs can be enabled and fees paid automatically upon performance of the one or more triggering actions (e.g., performance of a contact term, movement of the package from one location to another, change of custody of the package, etc.) through smart contract capability built into the blockchain-enabled packaging. In this example, when the shipper authenticates the package at the point of pickup (e.g., by scanning a bar code, QR code, or other machine-readable code, receiving a radio frequency signal from an RFID tag or radio module in the package, optically scanning or capturing an image of the package itself, etc.), their payment for the shipping can be received in accordance with the agreed upon and predefined carrier agreement, which is represented in the package's blockchain-based dataset. Similarly, when the package crosses an international border and must pay a tariff, import tax, VAT, or similar, this payment may be automatically enacted at the point of crossing (e.g., responsive to authenticating the package using any of the techniques described herein or other techniques to uniquely identify the package or its contents), again in accordance with the predefined contractual capability on the blockchain. This increases efficiency, reduces likelihood of fraud or corruption, and allows both shippers and producers to negotiate based on better data sets and real-world tracking and interactions.

Example Blockchain-Enabled Packaging—Manufacturing Examples

Manufacturers can utilize blockchain-enabled packaging to ensure the authenticity and validity of their final products. For example, manufacturers of luxury goods and accessories such as watches or purses could package their items using blockchain enabled 3D printed packaging, and sign each package with their private key—plus any relevant details such as date of manufacture, model number, original destination or dealer, any customization or relevant model information—which would then be written to an accessible blockchain. Customers can then use the manufacturer's public key to verify the authenticity of the item and its details. Furthermore, customers can record this purchase on the same blockchain, allowing them to verify item and purchase details that may be necessary for warranty or service claims, or to verify the authenticity of the item and purchase in a resale environment. In this example, each manufacturer could have their own blockchain, allowing them to continue to have visibility into the transactional lives of their product after the initial sale, and continue to verify authenticity in secondary market transactions.

Example Blockchain-Enabled Packaging—Logistics Examples

Figure 9:
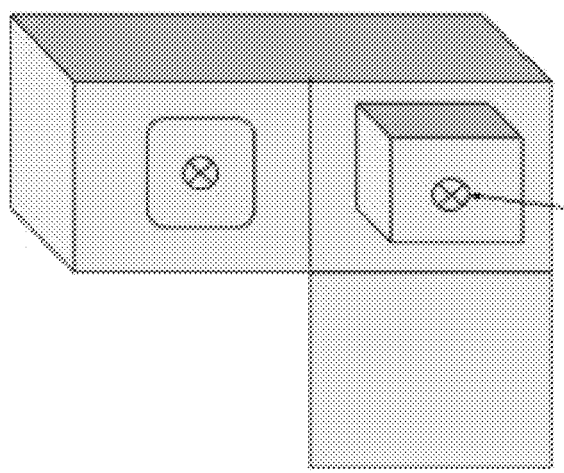
FIG. 9 is schematic diagram illustrating use of blockchain enabled packaging for delivery of a package to a pre-designated pickup location such as a locker or other storage unit.
Figure 9:
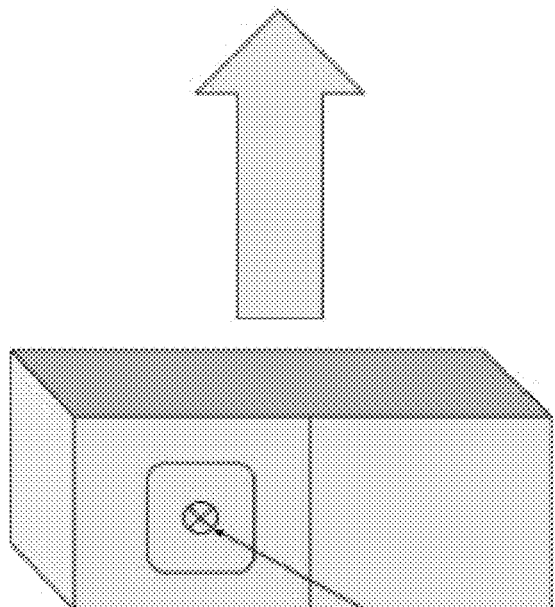
Figure 10:
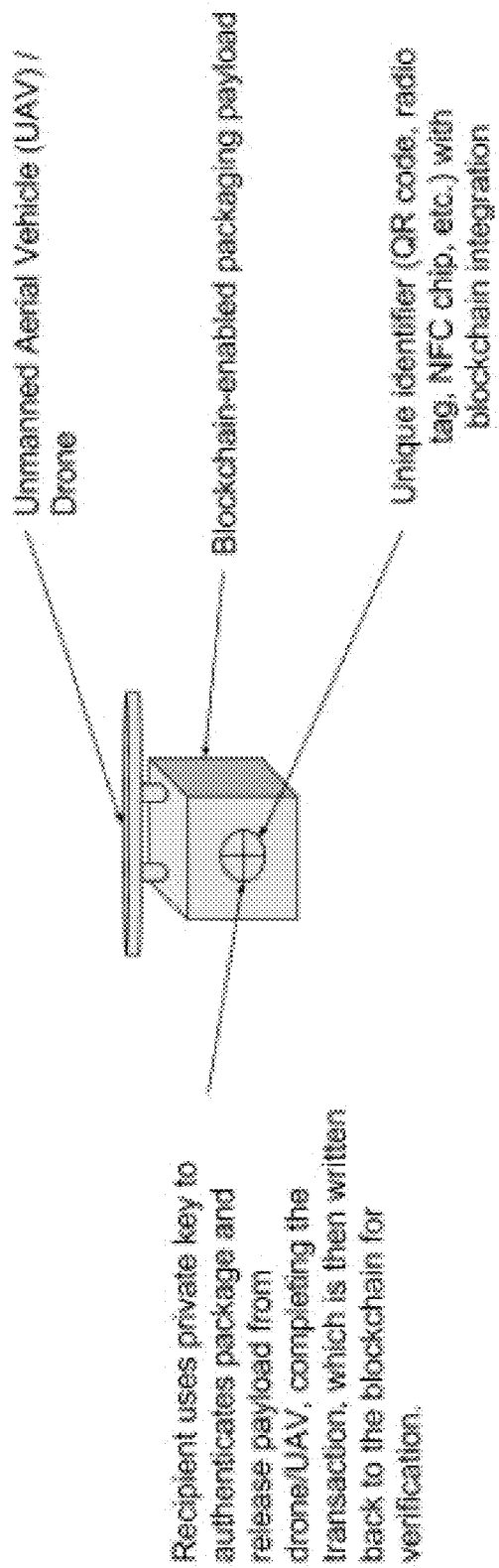
FIG. 10 is schematic diagram illustrating use of blockchain enabled packaging for delivery by self-driving vehicles or other unmanned autonomous vehicles (UAV) where there is no human involvement.

In another example, shipping and expediting companies can play the role of arbiter by providing verification of a package's authenticity. In this example, a shipping company would verify a package's contents as it is packed either individually or in conjunction with the retailer or manufacturer. It is possible that signatures utilizing the private key from each of these entities—manufacturer, retailer, and shipper—can be added to the blockchain's transactions. In this example, the recipient is able to verify not only the delivery of the item, but also the contents of the package upon delivery without even opening the package. Additionally or alternatively, the recipient may, prior to taking delivery, determine the conditions to which the package was subjected during transit (e.g., temperature, humidity, inertial forces, etc.) based on sensor readings from an internal sensor suite of the package that have been written to the blockchain, thereby ensuring that the contents were not damaged during transit. This application is particularly helpful in an environment where the delivery is done in an automated fashion—such as delivery by drone or unmanned aerial vehicle, delivery in a pre-designated pickup location such as a locker or other storage unit (described in FIG. 9), or through self-driving vehicles or other unmanned autonomous vehicle (UAV) where there is no human involvement (described in FIG. 10).

In these scenarios, the designated recipient can authenticate to the package and the blockchain to verify and complete the transaction. This information can then be read by the shipper, retailer, and manufacturer to ensure that the final destination was reached in accordance with the terms of the arrangement. These terms can also be written to the blockchain utilizing smart contract technology, including incentives or penalties, which can be automatically executed. In this example, the cost of the shipment can be reduced if the delivery is delayed, or an additional bonus amount can be paid by the recipient for expedited delivery. In another example, the cost of the shipment can be reduced or the shipment may be rejected if the contract terms are not met (e.g., the package was exposed to temperatures, humidities, and/or inertial forces outside those specified in the contract).

One example of this smart-contract deployment via enabled packaging can be found in pizza delivery. When the order is taken, the register creates a smart contract based on the interaction—including the type of pizza, order time, destination, cooking time, queue to get into the oven, etc. The process is then written to the blockchain as it progresses—including as the raw ingredients are assembled into a pizza, when the pizza goes into the oven, through to when the pizza comes out of the oven. When the pizza enters the sensor-enabled package, relevant information is written in real-time to the blockchain, which can include temperature, an accelerometer, GPS, or other sensors. The destination for the pizza can be retrieved from the smart contract, which will provide traffic and routing information to the delivery driver and the opportunity for the customer to track that information in real-time by viewing entries on the blockchain. Any guarantees, including delivery time, etc., can be enforced by the integrated smart-contract drawing data from the sensors, up to and including final delivery to the customer who authenticates and affirms the order upon delivery, closing the transaction and triggering appropriate payments per terms already established in the smart-contract.

In this example, smart-contracts and blockchain-enabled packaging are automating trust and verification with publicly or privately recorded and unalterable information by verifying what actually happened to the package and packaged goods, with payments, transfer of goods, exchanges of packaged goods for other value, final delivery to intended recipient, and so on. In this example, fraud, waste, and abuse through false reporting (my pizza was cold, my item was damaged, the delivery was late, etc.) is eliminated, and all elements of the transaction can be verified by any participant in the transaction, or an independent third party.

In another example, the power of this automated trust and verifiable transactions is deployed in the creation of crowd-sourced products (i.e. Kickstarter, etc.). In this example, smart-contracts are used to facilitate the irrevocable commitment to fund, but only at certain pre-determined stages, which are triggered through the integration of blockchain-enabled packaging. In this example, once initial commitments hit a certain amount, a pre-determined order of raw materials from a chosen vendor can be triggered. Once those materials are delivered—confirmed through blockchain-enabled packaging—another payment can be triggered to initiate the production process. When final goods are packaged for shipping, this entry is recorded into the blockchain, which triggers payment to a shipping company. When final products are received and authenticated by the intended recipient, additional smart-contract actions can be triggered, including adjusting payments based on tampering or damage, discounts in the event of delays, refunds based on damaged packaging, etc.

In another example of smart-contracts driving interactions through blockchain-enabled packaging, driverless cars become an on-demand delivery fleet when they are not being utilized by their owners. In this example, when items are packaged in blockchain-enabled packaging, it triggers a request for the closest available self-driving vehicle who can complete the delivery and return to its location in the allotted time, based on traffic, routing, weather, and other data from the point of pickup to the point of delivery. In this example, the self-driving car authenticates to the package, which is written to the blockchain. Sensors can update the blockchain during transit, triggering smart-contract interactions based on pre-negotiated penalties for damage, delay, over-temperature, shocks that would bruise vegetables and fruits, time of package in transit, etc. When the item reaches delivery, the recipient authenticates against both the package and the delivery mechanism (self-driving car, in this case) to complete the transaction. Trust and reviews can also be automated and aggregated utilizing these interactions, generating a verified dataset of trusted interactions sortable by vendor, by goods, by location, by time of day for the order, type of delivery method, transit time, delivery location, and more. These verified, reviewable interactions can share the trust of the supply chain in a similar way that current consumers might check Yelp! reviews or customer reviews on Amazon.com prior to placing an order.

Military and Defense Related Examples

In another example, smart-contracts and blockchain-enabled packaging automates access control in highly-regulated environments, such as military and defense contracts. In this example, the Department of Defense or other military/intelligence agency maintains their own private blockchain to facilitate these transactions based on the type of asset being secured, its classification level, and the "need to know" of the individual attempting to access the asset—all of which are written to the aforementioned blockchain and referenced to verify an interaction prior to executing it. In this model, because of the different levels of classification, the smart-contract terms enforce a one-way trust (i.e. Top Secret is automatically trusted by Secret, but not the other way around) as well as ecosystems that work at each level (UNCLASS, SECRET, T/S, TS-SCI, etc.). Additional transitive properties can be created in the smart-contract to authenticate against classification levels of cleared individuals from other agencies, providing the automated ability to share appropriate intelligence assets. In this example, physical and digital assets can all be classified and written to the same blockchain, thus providing a single point of access, verification, audit capability, etc. As artifacts are created, their existence and classification levels are written to the blockchain, and terms of their access are captured in a smart-contract methodology (i.e. Ethereum), which is also captured on said blockchain. This method also provides tamper-evident capabilities, i.e., a hash-value for the asset can be calculated and verified upon creation, and re-verified at each interaction to ensure that no changes (physical or digital) have been made to the artifact.

This leads to block-chain packaging for ammunition, refills, spares, etc., that can be re-issued or transferred by tender and acceptance between soldiers using private keys, through units using combo private and public keys, and so on. The inventory issue could be alleviated in units by transferring assigned items on a block chain rather than paper inventory. Could reduce losses. Could be used for custom packaging for cash that's distributed in theater, and reduce the loss of cash, because it was bundled with serials, packaged in track able packages, and so on.

Example Operations

FIGS. 11-18 are flow diagrams illustrating example processes 1100-1800 describing techniques for use in distributed manufacturing of products and packages, and blockchain enabled packaging. The processes 1100-1800, as well as other processes and techniques described herein, are illustrated as collections of blocks in logical flow diagrams, which represent sequences of operations, some or all of which can be implemented in hardware, software or a combination thereof. The order in which the blocks are described should not be construed as a limitation. Any number of the described blocks (i.e., operations, steps and/or techniques) can be combined in any order and/or in parallel to implement the process, or alternative processes, and not all the blocks and/or techniques described therein require execution. For discussion purposes, the processes are described with reference to the environments, architectures and systems described in the examples herein, although the processes may be implemented in a wide variety of other environments, architectures and systems.

Figure 11:
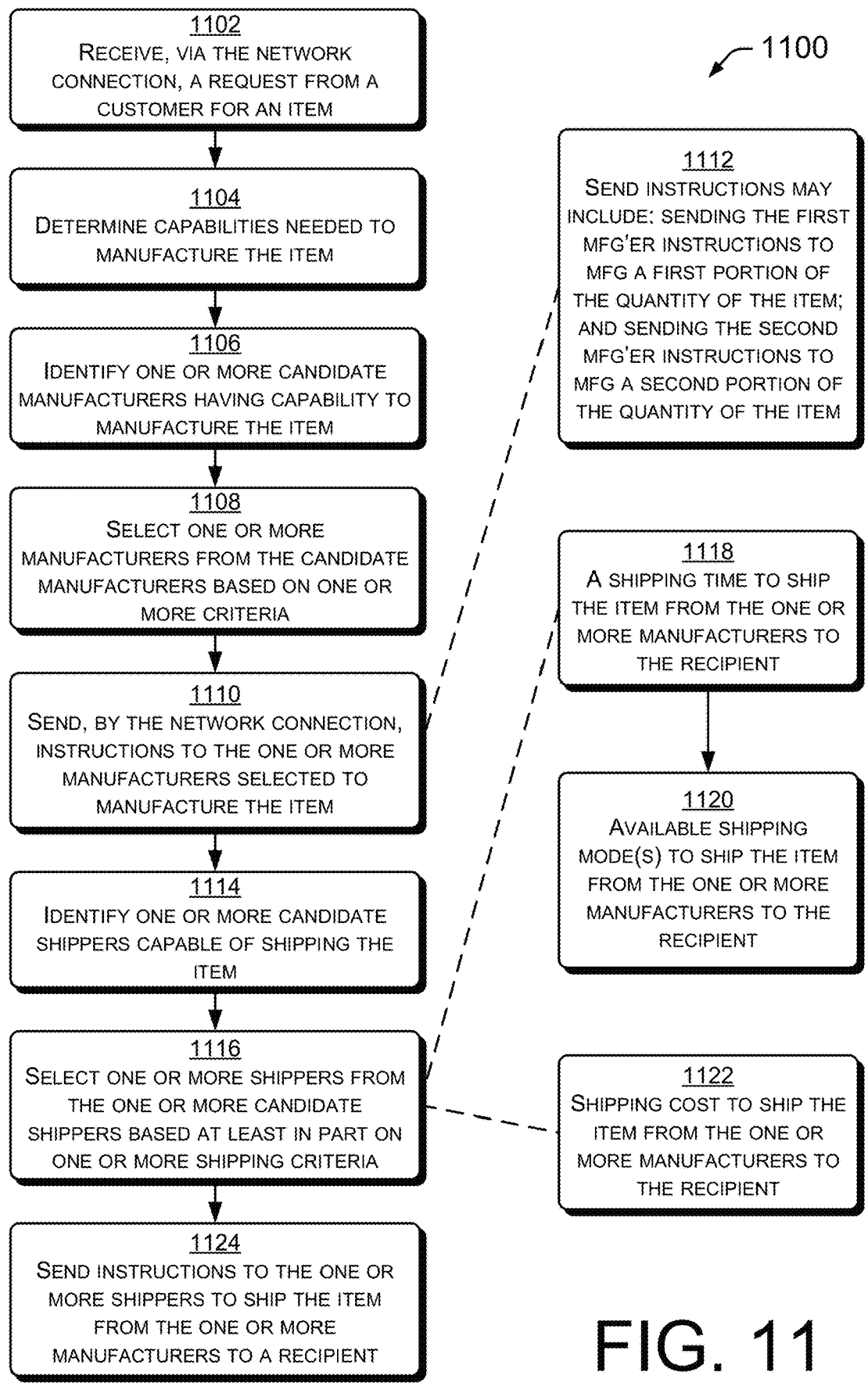
FIG. 11 is a flowchart illustrating an example process of distributed manufacturing.

FIG. 11 is a flowchart illustrating an example process 1100 and techniques for use in distributed manufacturing. At operation 1102, a request for an item may be received, such as over a network connection, from a customer. At block 1104, the capabilities needed to manufacture the item are determined. At block 1106, one or more candidate manufacturers having capability to manufacture the item are identified. At block 1108, one or more manufacturers are selected, from among candidate manufacturers. The selection may be based on one or more selection criteria. At block 1110, instructions may be sent, such as by network connection, to the one or more selected manufacturers. Block 1112 shows example techniques for sending instructions, such as by network connection, to the one or more manufacturers selected to manufacture the item of block 1110. At block 1112, the instructions that are sent may include: sending the first manufacturer instructions to manufacture a first portion of the quantity of the item, and sending a second manufacturer instructions to manufacture a second portion of the quantity of the item. At block 1114, one or more candidate shippers that are capable of shipping the item may be identified. At block 1116, one or more shippers may be selected from among the one or more candidate shippers based at least in part on one or more shipping criteria. Blocks 1118-1122 describe techniques that may be utilized to selected shippers. At block 1118, a shipping time (e.g., departure time, transit time, arrival time, etc.) from one or more of the manufacturers may be use in the selection process of block 1116. At block 1120, available shipping mode(s) to ship the item from the one or more manufacturers to the recipient may be considered. At block 1122, the cost to ship the item from the one or more manufacturers to the recipient may be determined, calculated and/or obtained. At block 1124, instructions may be sent to the one or more shippers to ship the item from the one or more manufacturers to a recipient.

Figure 12:
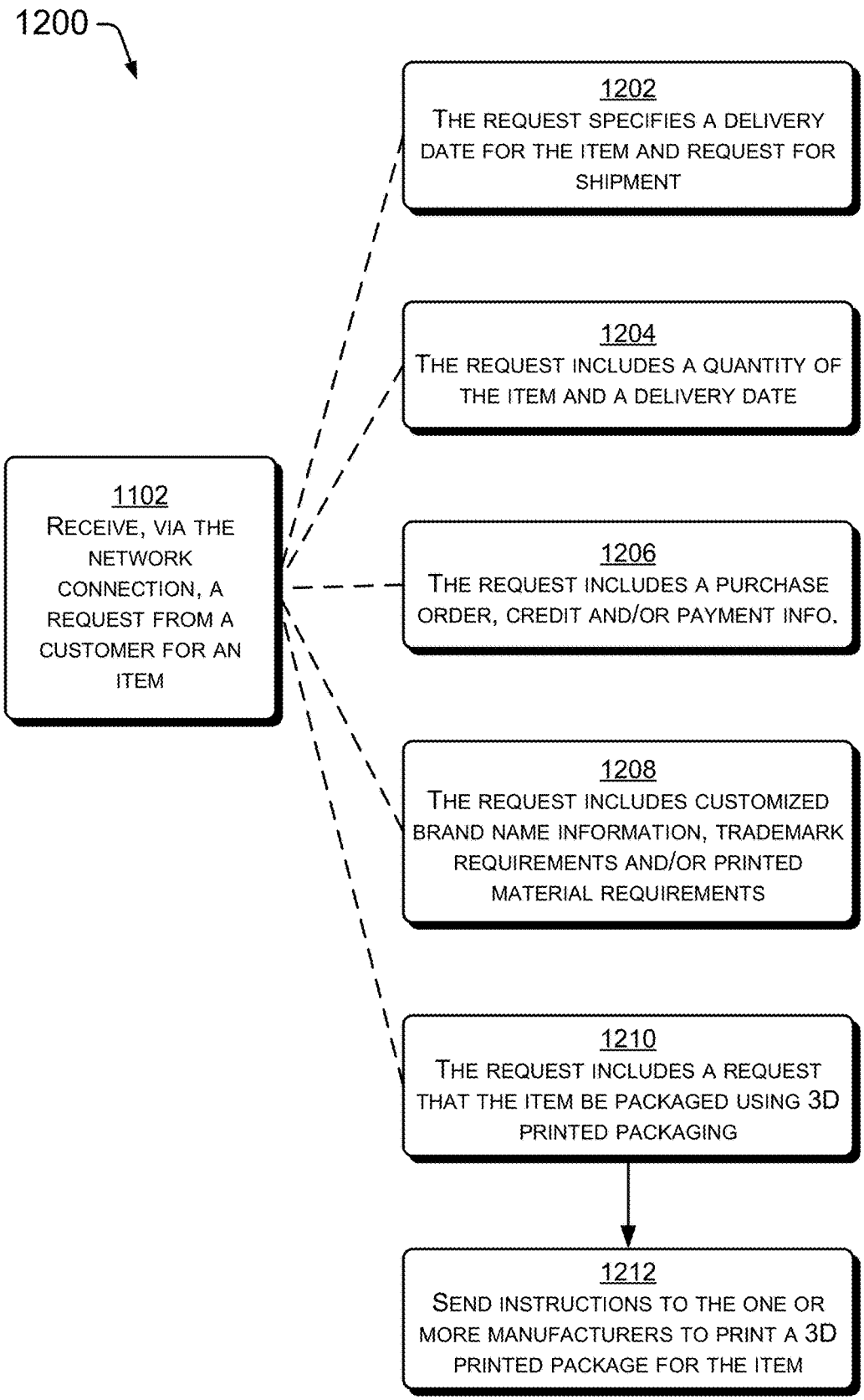
FIG. 12 is a flowchart illustrating an example techniques and aspects related to the request of block 1102 of FIG. 11.

FIG. 12 is a flowchart illustrating an example techniques and aspects 1200 related to the request of block 1102 of FIG. 11. Accordingly, FIG. 12 describes aspects of the request received from a customer and/or techniques for handling the request. At block 1202, the request may be configured to specify a delivery date for the item and/or request for shipment. At block 1204, the request may include a quantity of the item, information about the item, design requirements, product requirements, cost requirements, and/or other factors. At block 1206, the required may include a purchase order, account information, credit and/or payment information, etc. At block 1208, the request may include requirements for brand name and trademarks to be used in marking the item, and/or requirements for printed materials to be included with the item. At block 1210, the request may include a request that the item be packaged using 3D printed packing techniques and/or in a 3D printed package. At block 1212, instructions may be sent to the one or more manufacturers to print a 3D printed package for the item.

Figure 13:
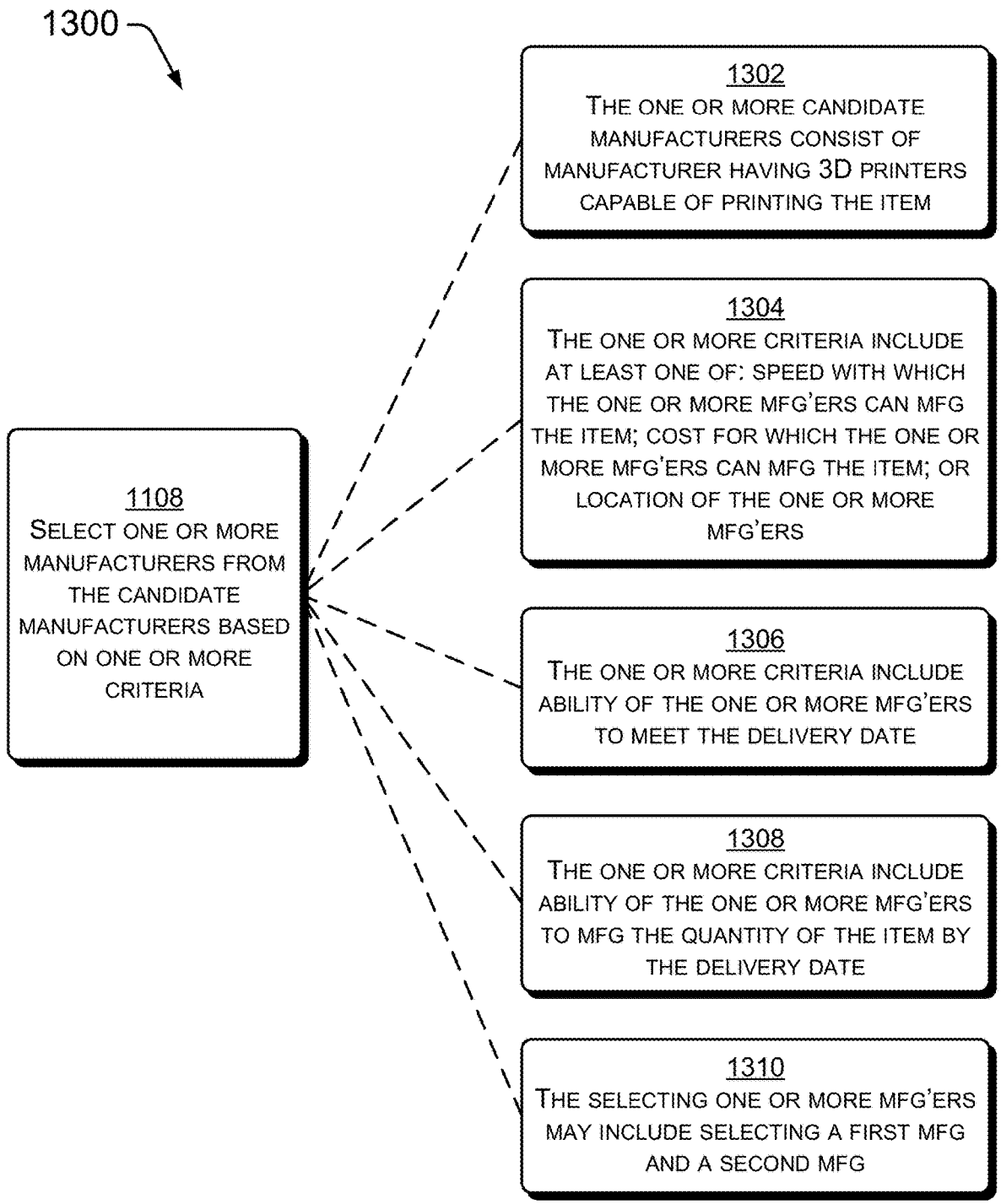
FIG. 13 is a flowchart illustrating an example techniques and aspects related to the selection of manufacturers of block 1108.

FIG. 13 is a flowchart illustrating an example techniques and aspects 1300 related to the selection of manufacturers of block 1108, and the sending of instructions of block 1110, of FIG. 11. Blocks 1302 through 1310 show example techniques for selecting one or more manufacturers from among the candidate manufacturers based on one or more criteria of block 1108 of FIG. 11. At block 1302, the one or more candidate manufacturers may consist of a manufacturer having 3D printers capable of printing the item. At block 1304, the one or more criteria may include at least one of: a speed with which the one or more manufacturers can manufacture the item; the cost for which the one or more manufacturers can manufacture the item; and/or the location(s) of the one or more manufacturers. At block 1306, the one or more criteria may include the ability of the one or more manufacturers to meet the delivery data. At block 1308, the one or more criteria may include the ability of the one or more manufactures to manufacture the quantity of the item by the delivery data. At block 1310, the process of selecting the one or more manufacturers may include selecting a first manufacturer and a second manufacturer, such as based on design requirements of the item, product requirements of the item, design and/or manufacturing ability of the manufacturer(s), costs of the design and/or the manufacture, delivery dates, scheduling and/or shipping costs and/or schedules.

Figure 14:
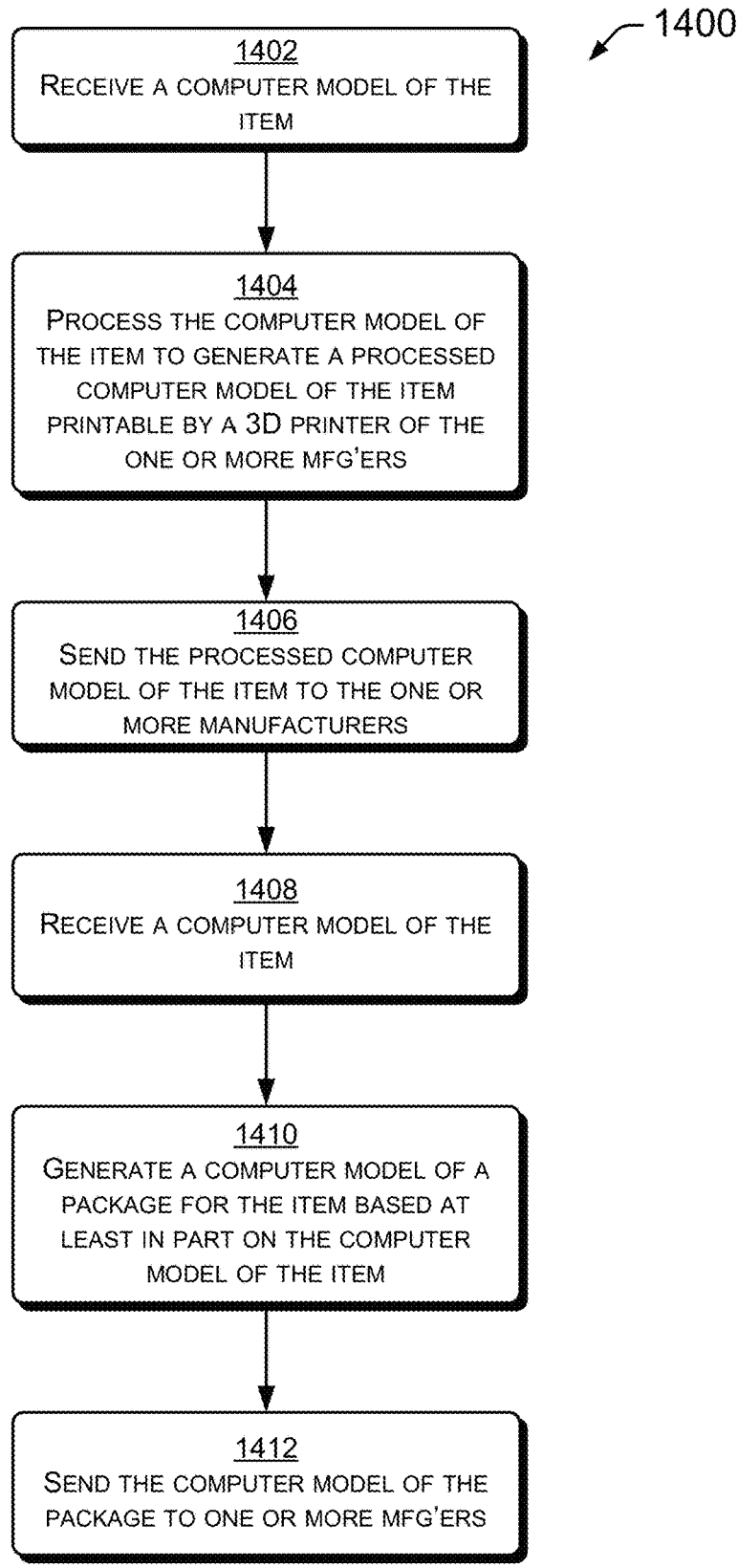
FIG. 14 is a flowchart illustrating an example for use in distributed product and packaging manufacturing.

FIG. 14 is a flowchart illustrating an example computer model related techniques 1400 for use in distributed product and packaging manufacturing. At block 1402, a computer model for an item is received. The computer model may be the instructions required by a 3D printer to print the item, and may be configured as a program, database and/or other object. At block 1404, the computer model of the item may be processed to generated a process computer model of the item printable by a 3D printer of the one or more manufacturers. In some instances, processing and/or translation of instructions, databases or objects may be required based on the required input of various 3D printers, which may have differing and/or proprietary input requirements. At block 1406, the processed computer model of the item may be sent to the one or more manufacturers. At block 1408, the computer model may be received, such as by one or more manufacturers, in an expected format appropriate to printers of the manufacturer(s). At block 1410, a computer model of a package is generated for the item. The package may be a 3D printed package, and may be of custom or standardized designed, and appropriate for the item. In an example, the computer model for the packaging may be based at least in part on, or derivative of, the computer model of the item. Thus, the design and/or computer model of the item may be used as input for creation of the design or computer model of the package for the item. In a further example, the computer model of the item and the packaging for the item may be unified into a single and comprehensive model. The model may be adapted to provide instructions to one or more 3D printers or other manufacturing machinery, each of which may perform portions of the item manufacturing and item packaging process. At block 1412, the computer model of the package (or unified item and package) may be sent to the one or more manufactures. The computer model(s) may be configured in, or translated to, a format appropriate to the 3D printers and/or manufacturing machinery of each manufacturer.

Figure 15:
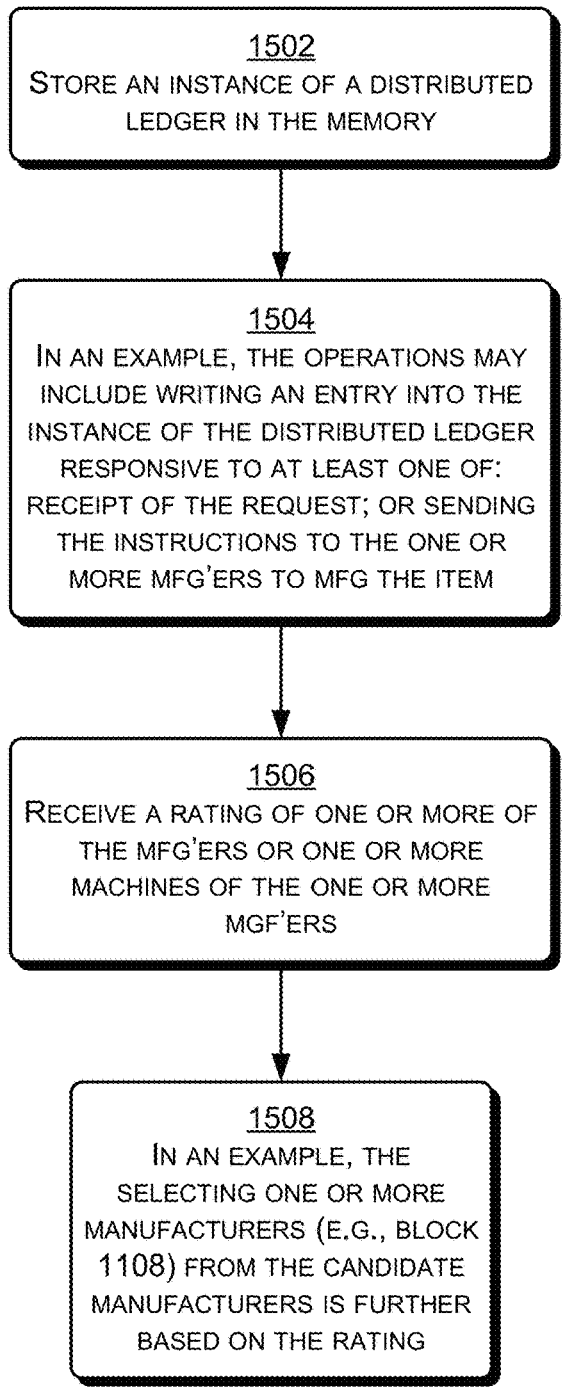
FIG. 15 is a flowchart illustrating an example process of distributed information management.

FIG. 15 is a flowchart illustrating an example process 1500 of distributed information management. At block 1502, an instance of a distributed ledger is stored in memory. At block 1504, in an example of the storing, the operations may include writing an entry into the instance of the distributed ledger responsive to at least one or more factors. An example factor is receipt of the request (e.g., request to design an item or packaging, request to manufacture the item, request to package the item, request to ship the item). A further example factor is sending instructions to a designer to design, a manufacturer to manufacture or package, or a shipper to ship, the item. At block 1506, a rating may be received that rates one or more of the manufacturers and/or one or more of the machines or printers of the manufacturers. At block 1508, in an example, the selecting of the one or more manufacturers (e.g. at block 1108 of FIG. 11) from the candidate manufacturers is based at least in part on the rating.

Figure 16:
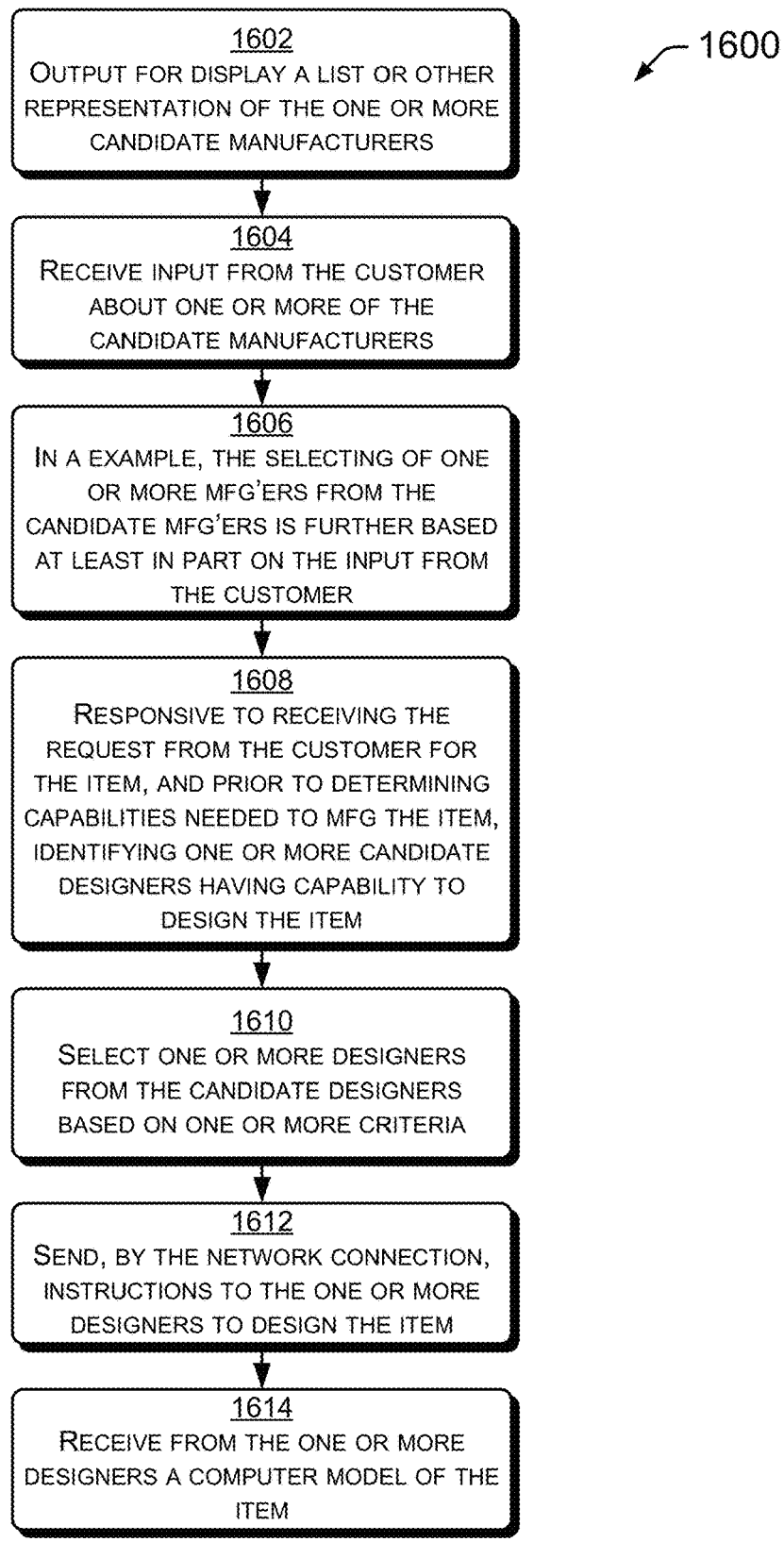
FIG. 16 is a flowchart illustrating an example process for information gathering and management to support distributed manufacturing.

FIG. 16 is a flowchart illustrating an example process 1600 for information gathering and management to support distributed manufacturing. At block 1602, a list or other representation of the one or more candidate manufacturers may be output for display. The output may be displayed to a customer, and may be configured to conveniently allow the customer to consider the candidates. Credentials of the candidates, their experience, ratings, available machinery and printers, etc., may all be provided to the customer. At block 1604, input may be received from the customer, regarding one or more of the candidate manufacturers. In the example of block 1606, the selecting of one or more manufacturers from the candidate manufacturers may additionally be based at least in part on the input from the customer. In the example, the customer interacts with a user interface, and is able to select an appropriate designer, manufacturer and/or shipper, for the customer's desired product. At block 1608, responsive to receiving the request from the customer for the item, and (in some instances) prior to determining capabilities needed to manufacture the item, one or more candidates designers having the ability and capability to design the item may be identified. The identification process may consider the designers skill, and also experience with printers available at different manufacturers that are compatible with the manufacture of the item. At block 1610, one or more designers are selected from the candidate designers based on the one or more criteria. Criteria may include design skill level, design approval by past customers, designer experience with 3D printers capable of manufacturing the item, design fees, designer location and other criteria. At block 1612, instructions may be sent to the one or more designers, instructing the designer(s) to design the item and/or its packaging. At block 1614, responsive to the request to design, the customer and/or manufacturer(s) may receive a computer model of the item and/or packaging for the item from the designer(s).

Figure 17:
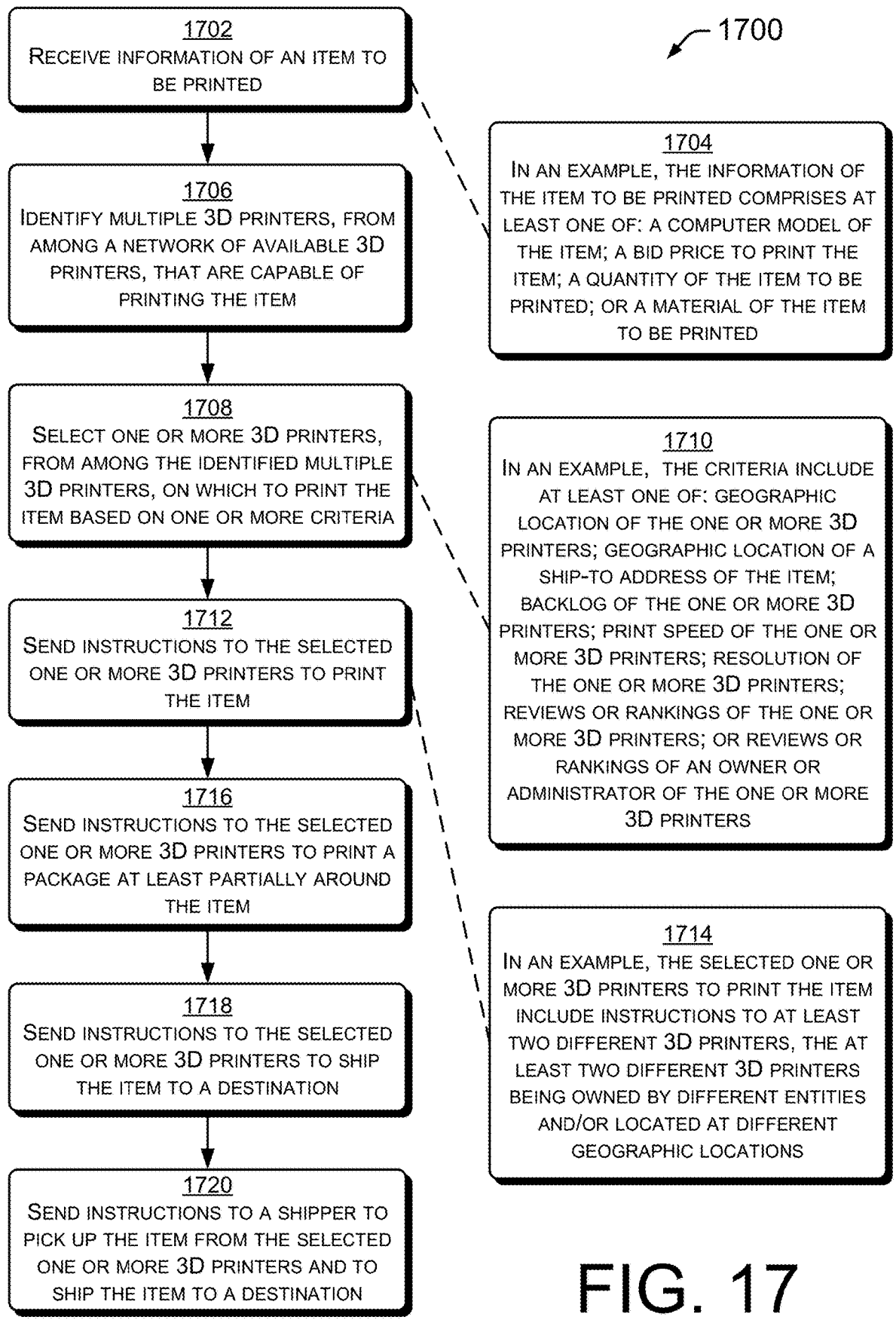
FIG. 17 is a flowchart illustrating an example process for information gathering and management to support distributed manufacturing.

FIG. 17 is a flowchart illustrating an example process 1700 for information gathering and management to support distributed manufacturing. At block 1702, information regarding and/or describing an item to be printed is received. The information may be configured as an application, database or other data structure, or a software object appropriate to serve as input to a 3D printer or other machinery. In the example of block 1704, the information of the item to be printed may include at least one of: a computer model of the item, a bit price to print the item; a quantity of the item to be printed; and/or a material of the item to be printed. At block 1706, one or multiple 3D printers, from among a network or group of available 3D printers, are identified. The identified printers are among those capable of printing the item. At block 1708, one or more 3D printers are selected from among the identified 3D printers. The identified and selected printers are consistent with the criteria of the item to be printed. In the example of block 1710, the criteria may include at least one of: geographic location of the one or more 3D printers; geographic location of a ship-to address of the item; backlog of the one or more 3D printers; print speed of the one or more 3D printers; resolution of the one or more 3D printers; reviews or rankings of the one or more 3D printers; or reviews or rankings of an owner or administrator of the one or more 3D printers. At block 1712, instructions are sent to the selected one or more 3D printers (or the companies associated with the printers) to print the item of the customer. In the example of block 1714, the instructions sent to the selected one or more 3D printers to print the item may include instructions to at least two different 3D printers, the at least two different 3D printers being owned by different entities and/or located at different geographic locations. At block 1716, instructions may be sent to the selected one or more 3D printers to print a package at least partially around the item. At block 1718, instructions are sent to the selected one or more 3D printers (or associated companies) to ship the item to a destination. At block 1720, instructions may be sent to a shipper to pick up the item from the selected one or more 3D printers and to ship the item to a designation.

Figure 18:
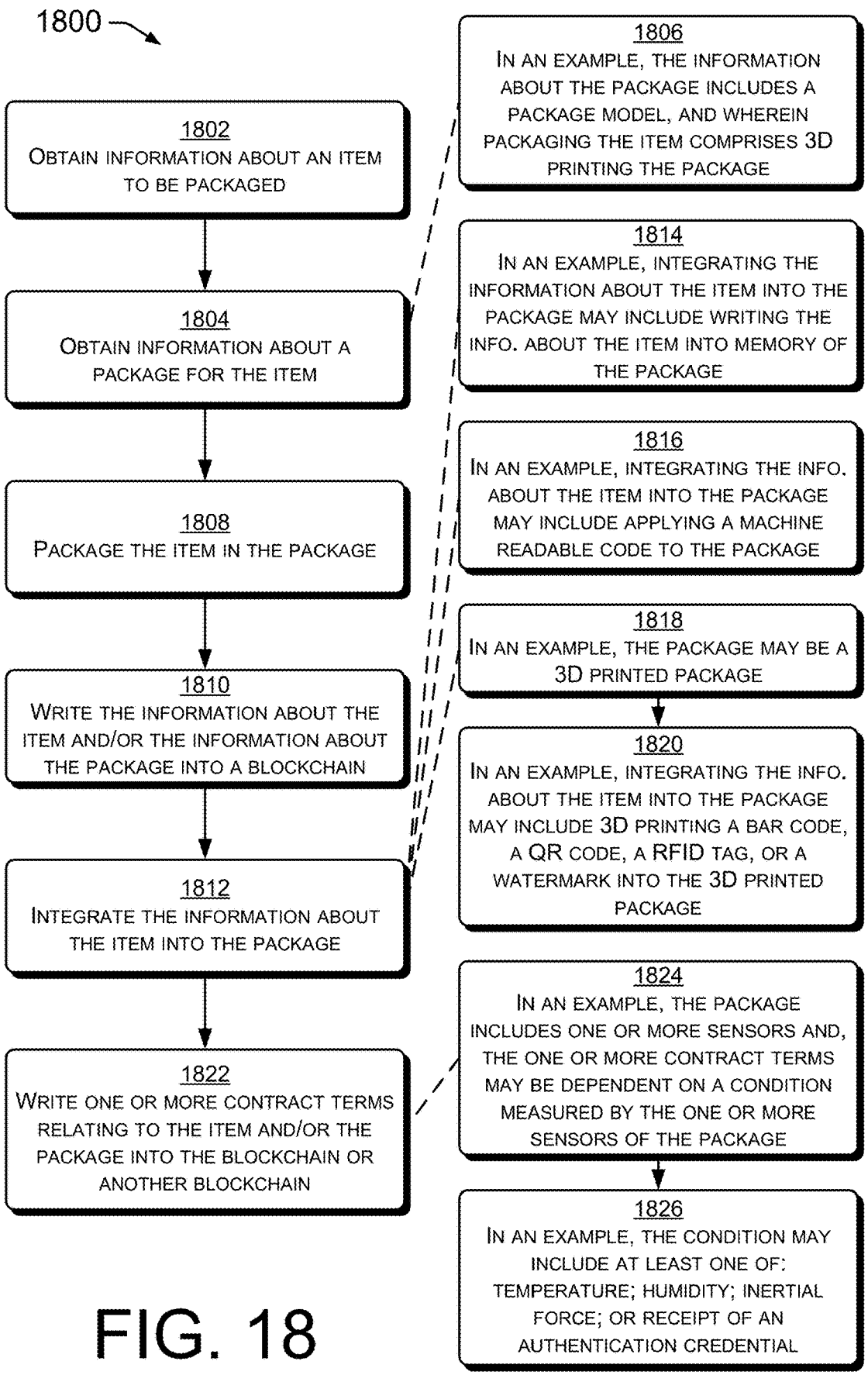
FIG. 18 is a flowchart illustrating an example process of blockchain enabled packaging.

FIG. 18 is a flowchart illustrating an example process 1800 of blockchain enabled packaging. At block 1802, information about an item to be packaged is obtained. At block 1804, information about a package for the item is obtained. In the example of block 1806, the information about the package to includes a package model or a defining description, and the packaging for the item includes 3D printed packaging. At block 1808, the item is packaged into the package. In an example, the package is printed around the item. In another example, the item is printed and the package is printed around it. At block 1810, information about the item and/or information about the package is written into a blockchain. At block 1812, the information about the item is integrated into the package. In the example of block 1814, the information about the item is integrated into the package, and may include writing the information about the item into memory defined in, or part of, the package. In the example of block 1816, the information about the item may be integrated into the package, such as by applying a machine-readable code to the package. In the example of block 1818, the package may be a 3D printed package, and the information about the item may be integrated into the package as part of the 3D printing process by which the package is constructed and/or printed around the item. In the example of block 1820, integrating the information about the item into the package may include 3D printing a par code, a QR code, an RFID tag and/or a watermark into the 3D printed package. The integrated information may be readable by humans and/or readable by machines, or may contain dual imprints or similar and/or the same information, one configured for human observation and one configured for machine reading. At block 1822, one or more contract terms may be written into the blockchain or another blockchain. The contract terms may relate to the item and/or the package, and may be related to the designer, the manufacturer, the shipper and/or the customer. In the example of block 1824, the package includes one or more sensors. In further examples, the contract terms may be dependent on, or judged by, a condition measured by the one or more sensors of the package. In the example of block 1826, the conditions associated with the sensors may include at least one of: temperature; humidity; inertial force; and/or receipt of an authentication credential.

Examples of Improving 3D Printer or Other Machine Utilization and ROI

New manufacturing methods for pharmaceutical products (including medicine, supplements, and similar items) are changing the way these products reach end users. In particular, additive manufacturing is creating unique opportunities to tailor products to the individual consumer in an on-demand way. This may include customized dosing based on a particular set of dynamically generated inputs, combining multiple medicines and dosings into a single pill (or patch or other delivery mechanism), adding time-delay capability to a multi-medication pill, or adding non-medical supplements to a medical delivery mechanism (pill, patch, etc.). All of these offer great value to both the consumer and the producer, but injecting additive manufacturing into traditional supply chains is not without its own challenges.

Because additive manufacturing technology (3D printers, for example) typically contain networked computing devices or capabilities, a number of novel solutions to the challenges of deploying the technology at scale exist. In particular, several challenges lie in managing usage of the manufacturing platform itself (i.e., the 3D printer), including availability, cost, scheduling, managing need for human interaction versus autonomous operation, and more. This application describes solutions to these problems in several unique ways.

In some examples, a distributed network of additive manufacturing machines can report availability of the devices to accept a manufacturing sequence (e.g., "print job"), thereby capturing latent supply (i.e., underutilization of printers) and making it available to others with unmet demand. There are a number of factors that can be included with regards to availability or capacity of the additive manufacturing device (or other traditional manufacturing machines for that matter), including factors such as duration of print job, material from which to print, location of printer, location of purchaser, location of recipient, "time to human intervention" or "availability of human intervention," finish quality, precision/resolution, size, downstream post-processing requirements, shipping options, or any combination of these factors. The print job may include data describing or related to any or all of these factors. This data can be presented in a machine-readable format and/or a human-readable format, and can be accessed via traditional computers or mobile devices and via web browsers, printer drivers, or other applications (e.g., computer aided design applications, graphics applications, e-commerce marketplace applications, etc.). This platform allows manufacturers and individuals to initiate manufacturing sequences (e.g. "print jobs") that align with their other business goals or constraints.

In some examples, a version of this distributed network management capability for additive manufacturing capacity can be deployed internally within a single organization that maintains multiple manufacturing devices or 3D printers (e.g., within a single pharmaceutical company, manufacturer, device company, university, etc.). The distributed network management can interface with other systems and networks of the entity to capture data regarding capacity, supply and demand, in addition to other business elements from other information technology systems within the enterprise, such as customer orders, wholesale supply needs, coordinated logistics information, sales goals or forecasts, weather, employee schedules, or other sets of input. Any or all of these systems can be inputs to inform the distributed network management system, and the distributed management system may output information to these systems regarding external use of the enterprise's 3D printers or other machines.

In some examples, this distributed network can allow individual additive manufacturing devices or 3D printers to participate when not otherwise occupied by work generated by the device owner. In this scenario, device activity can be monitored remotely, and when not in use, accept manufacturing requests from the network that are compatible with its capabilities, as described above. In this example, a system of smart-contracts can enforce payment between the device owner and the requestor, such that an appropriate compensation rate is automatically determined based on relevant factors (e.g., supply, demand, peak vs. non-peak hours, or other market conditions), and reliably transferred between parties at the agreed-upon intervals (upon partial or total completion of the manufacturing session, upon successful delivery of the item, or any combination thereof).

In situations where multiple additive manufacturing devices are operating, this technology offers the capability to capture, calculate, and predict time-related activities such that additional efficiencies can be gained. For example, it is possible to use prior device activity to predict availability (i.e. the device is in use from 9 AM to 5 PM, but idle otherwise, or is typically idle on weekends, etc.). This allows the device owner to maintain uninterrupted operation at their existing pace and pattern, yet allow the device to maximize the value in the latent capacity during periods of typical non-use. Other time-related calculations can include coordination between devices such that manufacturing sequences with different time horizons complete concurrently and can be moved, manipulated, or finished in a batch fashion. In this example, one device may begin a 6 hour sequence (e.g., printing a first part of an item), and two hours later another adjacent device may begin a 4 hour sequence (e.g., printing a second, smaller part of the item), with a final device waiting an additional 2 hours before starting a 2 hour sequence (e.g., printing a package for the item). Each of these sequences end at the same time, allowing any intervention (by human and/or automated means such as robotics) to complete this transitional work, such as assembly of the parts and packaging the item, all at once. This can drastically reduce costs in terms of both time and man-hours. This scheduling can be accomplished via a scheduling module of a computing device of the enterprise (or of a remote distributed manufacturing platform) based on the machines used, the print/manufacturing rates of the machines used, the models of the parts/items/packages to be printed, the print or other manufacturing time required to print the respective parts/items/packages, the availability of human operators and/or automated material handing equipment, or the like.

In some examples, coordination between manufacturing devices can be based on other factors, including coordination of multiple parts of an assembly and timing completion such that the parts are ready for subsequent steps in the appropriate order. This coordination can also take into account external factors, such as multiple additive manufacturing devices at multiple locations. These external factors can include timing of shipment, shipping modality, and others. In this example, it may be the case that some parts are produced domestically and shipped via ground, or air, while others are produced internationally and shipped via cargo ship. In this scenario, the items with shorter manufacturing and shipping cycles can be initiated when the cargo ship reaches a certain destination or distance from final delivery, allowing "just in time" manufacturing capability to happen dynamically and reducing need to store or warehouse any component parts. In this example, all coordinated parts arrive in precisely the order and quantity in which they are required, as determined by the business drivers of the manufacturing effort.

Algorithms can be optimized or tailored for printing speed, shipping speed, or both. In another example, part of the manufacturing process can take place en-route. For example, items can be printed on the container ship as it transits the ocean, post-processing activities may be carried out on a cargo plane while it is in the air. This "mobile factory" can also be coordinated with the other components of the distributed supply chain, such that their deliveries are tightly coordinated to maximize efficiency and minimize waste.

Real-time supply-chain interactions are also possible. For example, if an item is ordered for one customer, but another order for the same item is received while the item is still being made or is in transit, it is possible for the two customers to negotiate such that both parties are happy with the exchange. For example, one customer is willing to pay more to get an item faster, and the second customer is willing to accept a portion of this payment in exchange for delayed delivery of a substitute item as their original order is used to fulfill the first customer's higher-priced offer. This sort of exchange can be accomplished by the manufacturer and/or distributed manufacturing platform identifying the two orders for the same part, and sending notifications to one or both customers. By way of example, the notification may offer a first customer a discount in exchange for a delayed delivery of the item, may offer the second customer an option to obtain the product sooner for a higher price, may connect the first and second customers to negotiate the exchange, may initiate a bidding process to determine which customer will receive the item first, or any number of other techniques. Upon receiving a response to such notification from one or both customers, the manufacturer or distributed manufacturing platform may adjust the manufacturing process, shipping mode, shipping addresses, payments, and any other portions of the transaction in order to accomplish the exchange.

In some examples, the distributed network or a distributed manufacturing platform may provide a dashboard, management panel, or other application to a computing device of the manufacturer. In some examples, via this application, the manufacturer may indicate how much extra capacity they're willing to share (percentage, or hours, time windows, etc.). In other examples, the printer owner might set a dollar amount they're seeking to recover from their printer each day/week/month/quarter/year. An algorithm at the manufacturer's computing device, distributed manufacturing platform, or other entity can determine how many jobs and of what kind to take to meet that number (or, to hit the number faster, slower, maximize profit, etc.). In this example, the people with the printers control when and under what terms they take work through the distributed network.

Examples of Improving Access to 3D Printing and Other Machine Resources

A significant barrier to access exists regarding manufacturing equipment in general, and advanced additive manufacturing technology in particular. In many cases, the acquisition of these machines is prohibitively expensive for small and mid-sized firms, they lack the expertise or personnel to effectively use these machines, and/or their need for the technology simply doesn't justify the capital expenditure. It is also common that major urban areas have shared access to these technologies (i.e., a "maker space") but firms located outside of these areas are often out of luck. Even if a firm can afford to acquire the physical additive manufacturing technology, an additional challenge exists in accessing required packaging expertise to maximize the value of packaging for products may by these additive manufacturing technologies. This application describes techniques that lower the cost to additive manufacturing capabilities and increase access to these resources in a number of different ways.

In one example, manufacturers are able to access multiple packaging designs in a template format, and make additional customizations. In this example, manufacturers are not required to design the packaging themselves, but may add pre-designed components to achieve custom functionality and appearance. These customizable components may include, but are not limited to, packaging type (box, bottle, blister pack, individual foil-type tear packets, tamper resistant, child-proof, etc.). Additional components include models based on inputs such as product size, shape, dosage, standard prescription size (e.g. one week, 30 days, etc.). Packaging may be further customized by selecting integration of additional sensors (e.g. humidity, temperature, shock, torsion, opening/tampering, etc.) or external visual customization.

In the pharmaceutical context, external visual customization of packaging may include some or all of the following: regulatory compliance markings (individual numbering, lot numbering, manufacture date, manufacture location, etc.), as well as patient or provider information, medication instructions or handling details, dosing information, overdose information, side effects, source verification information, anti-counterfeiting markings or other technologies, marketing or branding such as a logo or similar mark, or any other desired external visual customization.

Furthermore, these customizations can be created on an individual, on-demand basis. In this example, one customer of a particular medicine or other product could receive it in on set of packaging, while another customer receives identical medication or product in an entirely different packaging, customized based on the needs or desires of the end-user, branding or advertising efforts of the manufacturer, regulatory requirements based on consumer location, or any combination therein.

In addition to selecting these customizable components from a pre-designed template-style gallery of options, this application describes crowd-sourced design functionality or multi-party collaboration. In this example, one party may be responsible for designing the product, while another party may be responsible for designing the physical elements of the packaging, and yet another party responsible for designing the visual representations on the outside of the packaging, etc. Additional collaboration, crowd-sourcing, or multi-party engagements are possible by engaging additional service-providers in the supply chain, including printers or print bureaus, firms providing finishing work, shipping and logistics companies, last-mile solution providers, customs officials or other regulatory bodies, etc.

In this example, the physical design elements can be altered dynamically based on the downstream delivery logistics. For instance, if a particular product is going to be shipped in a modality that does not offer climate control, temperature and humidity sensors may be required to ensure that the potency or efficacy of the medication is not degraded during transit. Additional physical safeguards may need to be built into the packaging to help prevent any temperature or humidity issues. In another example, if a particular medication is normally shipped via air cargo, but will be shipped via overland freight, additional protective packaging may be required. If a particular shipment is being delivered to a geography with additional regulatory requirements, those can be built into the packaging based on the final destination, and/or any regulatory or customs waypoints. Additionally, in this pharmaceutical context, medications regulated as Controlled Substances can have additional packaging and handling demands, all of which can be accounted for in the packaging design on this platform. In some examples, the wholesale or retail requirements may be dynamically altered, providing for unique configurations, quantities, display locations (e.g., likely display on endcaps, top shelves, eye-level shelves, or ground-level shelves, with important package and label characteristics dynamically determined by who will see the packages and where), by needs for automated package handling equipment machine readability requirements (e.g., codes on top, side, front, back, or bottom of packages), or other related cues. Some examples might include physical design elements based on types of automated equipment handling (e.g., space for forklift tines, handles for robotic arms, indentations for robotic graspers, locking components for pallets, etc.).

While this application describes techniques to increase access to additive manufacturing capabilities and talent for manufacturers, it also increases capabilities for designers, where those capabilities were previously unavailable at their size or scale. This ability to share resources and access scale on-demand can allow for additional innovations benefitting designers and manufacturers, as well as end-users.

Example Techniques to Improve Shipping Efficiency

In some examples, this application describes techniques for the coordination and integration of shipments from disparate locations to a single location or in a linear fashion to facilitate for finishing, post processing, assembly, assembly, and/or packaging. To use another pharmaceutical example, the effects of individual drugs are enhanced when taken in conjunction with each other. In settings where the combinatory drugs are produced by different manufacturers, the techniques described herein can facilitate packaging that enhances this ability to combine medications. In this example, the initial dosage may be created in such a way that it is partially packaged (e.g., suspended, presented, or otherwise accessible) and an additional medication or dosage can then be added to the core dosage and the packaging completed around it, resulting in a single package featuring multiple medications from multiple manufacturers. In some examples, the partial packaging may include a temporary cover or seal that can be easily removed in order to add the additional medication before printing the remainder of the package.

In some examples, multi-modal packaging can be created that adds value to the manufacturer, consumer, or logistics company. In one example, individual dosages may be produced in bulk at one location, and shipped with minimal packaging to a different location, where they are packaged and distributed in accordance with other demands (i.e., HIV treatments and tailored cancer treatments that require a "cocktail" of drugs can be packaged as a customized set of daily dosages from these bulk manufacturers). The packaging can be customized as mentioned above, despite coming from multiple manufacturing sources.

Combining medications successfully can require other inputs such as location or geography, time required to ship from one location to another, volatility of particular compounds over time or in particular environmental contexts, and more. All of these can be taken into account and addressed through packaging modifications, supply chain enhancements, or business processes enabled through the platform. In some examples, multiple medication sources can be integrated into a single additive manufacturing device and co-located with a physical brick and mortar store (i.e., a machine that prints pills but is located in a pharmacy, where the pharmacists provides their existing set of services to the patient, but the medication is created on-site, on-demand, and/or in combination customized to the patient when needed).

Example Auditing, Authentication, and Digital Rights Management (DRM)

Because the techniques described herein allow the supply chain to become distributed and disintermediated, it can be beneficial to authenticate users and provide traceability and auditable records to ensure the integrity, effectiveness, and validity of anything created or packaged using the platform. This can be accomplished in multiple ways.

In one example, any party involved in the transaction (e.g. a human such as a designer, an entity such as a manufacturing corporation or transportation provider, or a machine such as a printer) is assigned a unique identifier on a shared distributed ledger (e.g. a unique address on a blockchain). The nature of the interactions between the parties and the transaction can be included explicitly or intentionally obfuscated. In some examples, it is beneficial to include the details of the transaction, such as to provide authenticity and provenance of a particular item or medication, and verify that it was created by the original and intended manufacturer. In other examples, it may be beneficial to intentionally obfuscate information. In this example, it may be beneficial for regulators to be able to see which providers are prescribing how much of a particular medication, but they need not (and, indeed, should not) be able to personally identify information about which patients are recipients of that provider's prescriptions.

The ability to link the manufactured item, the packaging, and the parties in an interaction can provide additional benefits to participants in the network. For example, this "life story" can significantly reduce medication adulteration, theft, counterfeiting, or diversion. The shared distributed ledger can be queried by potential acquirers (e.g., patients, pharmacy, retailers, shippers, etc.) to verify that the shipment is legitimate, valid, undamaged, and unencumbered by any nefarious background circumstances. The ability to query these datasets can also facilitate more efficient product or drug recalls, track impact through the supply chain to end-users, identify potential sources of counterfeit or infringing goods, and increase regulatory efficiencies.

This shared distributed ledger also enables low-friction licensing transactions between parties. In this example, smart-contracts can be used to license intellectual property including, but not limited to, packaging designs, patents, copyrights, production time on a printer, raw source materials, visual designs, or other valuable materials. These smart contracts can be predefined, or negotiated for each transaction, and can be written to the blockchain and may be in addition to, may incorporate, or may be used instead of traditional shrink wrap or click through licenses. In these transactions, because they are written to the ledger, use of any intellectual property on the network can be verified and compensated automatically according to pre-negotiated royalty rates. The network facilitates a dynamic pricing capability, and can accommodate multiple input variables—for example, whether or not a generic medication is acceptable will impact packaging and branding decisions, number of units the license allows to be generated, whether the item can be preproduced or resold, etc.

Example Techniques for Improving Trust and/or Reducing Risk

The ability to capture transactions on a shared, distributed ledger can also address a significant problem in the distributed manufacturing space: lack of trust between prospective participants. In traditional business relationships, trust can be built over time and through conversations, meetings, and other professional interactions—both in-person and virtual. In the context of a distributed manufacturing platform, trust must be supplied via structural mechanisms to ensure that an acceptable level of trust is present for first-time participants, and for existing participants engaging new partners for the first time. This application describes multiple ways to generate, capture, provide, and ensure this minimum level of trust between participants, while at the same time increasing transparency and auditability, thereby reducing the risk of fraud or bad acts.

In one example, the shared, distributed ledger allows participants to leave a review, offer feedback, or make a comment about the interaction that is linked to their relevant entries in the ledger. By both validating the participant as a verified party in that transaction, and linking to that transaction in conjunction with their response, the techniques described herein incentivize honest and forthright interactions, and quickly surfaces participants who are not meeting expectations.

In some examples, the system may hold payment to new participants in escrow until a positive review is received by the customer, thus preventing fraudulent manufacturing from impacting unsuspecting customers. This may be done for a certain time period (e.g., 3 months, 6 months, 12 months, etc.) or a certain number of transactions (e.g., first ten orders) or when a certain threshold is reached (e.g., until 80% of reviews are positive). It may also be reinstated at any time given similar triggering functions (i.e., positive reviews fall below a set threshold, negative feedback is received, fraud is reported, data analytics of transactions involving the entity indicate likelihood of fraud, a number of flagged transactions in a certain period, etc.).

In some cases, each individual actor may be assigned an identification based on immutable information, including personally identifiable information such as retina scans, fingerprints, or other factors, which may be used to affirmatively allow (white list) actors, or prospectively disallow (blacklist) actors. Similar characteristics could include physical addresses, IP addresses, system hardware identifications as with CPU embedded identifications, internet providers, or other characteristics. Heuristically generated factors could also play a role as with malware and virus scanning, but focused on factors in the stream of commerce, including flooding systems with entries, and other functions that indicate malintent, or lack of ability to provide the ordered products in the quantities desired.

Conversely, the system may also use these capabilities to prevent fraudulent customers from impacting the network by ordering items but claiming to have never received them, leaving negative feedback or ratings, etc. In some examples, this can be done via a third party verification of the transaction, which can be done remotely through digital techniques, physically through an in-person transfer of items, or in a hybrid mode where some third party verification is proffered (e.g., by the delivery driver verifying the delivery of the package and its contents, by video created by the delivery drone, etc.). In some examples, the system may limit the number of orders or price of orders for new customers until a reputation is established, or may require customers to put a good faith deposit, or percentage of the total purchase amount, in escrow prior to ordering.

In either case, the amount of energy required to participate in the system fraudulently is increased, and the benefit of doing so is decreased, thus minimizing negative participants on the network through economic incentives. Because the system is decentralized, additional controls can be implemented or altered at any time to adjust for unforeseen threats or fraudulent practices. Auditability through the shared ledger can allow for reparations to impacted parties after the fact, and also facilitates forensic capabilities that may allow the system to detect and prevent fraudulent activity in near real-time.

This review functionality is particularly important in building a peer-reviewed network of collaborators, considering the multitude of roles potentially required to complete more a more complex transaction (i.e., item designer, packaging designer, printer, shipper, buyer, etc.). The ability to create a feedback loop of community interactions will ensure that active, visible, capable participants are rewarded for their contributions by recognition from others they have worked with. Likewise, less-scrupulous or less-capable participants will also have their participation levels made available for review by a potential partner prior to engagement.

In another example, many of these feedback mechanisms can be automatically generated and enforced via smart contract capability contained within the platform, as well as with sensors or other data-gathering capabilities built into the packaging. In this example, particular metrics regarding a transaction can be captured and shared automatically (i.e., if the production started on time, was completed on time, shipped as agreed, whether the package was dropped or overheated in transit, etc.).

Because the feedback is generated automatically, situations may arise where human review and feedback becomes necessary as an arbitration function. In this example, it is possible for a distributed manufacturing platform to offer token-based incentives for participants not party to the transaction in question to play the role of arbitrator. This human intervention allows the distributed manufacturing platform to be flexible and adapt to situations by leveraging the great value in automated, sensor-based feedback loops, while also accounting for the possibility of data errors, sensor malfunction, fraud/tampering, or other related issues.

These combined capabilities—automated, sensor-based feedback loops and human-powered intervention with network incentives—can be combined to allow contractual allocations of risk, such as insurance or similar financial mechanisms. These verifiable data sources can allow for the application of financial tools and methodologies that can help insure, finance, or otherwise support production efforts, while also allowing for automated enforcement of contract terms. This capability also allows participants to avoid certain existing frictions in dealing with multi-party collaborations, including currency fluctuations or exchange issues, and can enable collaborations that were previously impractical or impossible.

Additional verification and validation mechanisms can be included on the distributed, shared, immutable ledger. In this example, additional evidence or documentation of a product or service can be captured (such as video or photographic content of the item being produced, sensor data regarding production, or other elements). A cryptographic hash function of this evidence can be generated and written to the ledger (i.e. blockchain) such that the authenticity of the evidence can be verified, but the artifact itself can be stored off-chain (such as a cloud-based image or video hosting service, a vendor's own off-site storage, or with the customer). The authenticity of the evidentiary artifact can be verified at any time by re-generating the cryptographic hash and comparing the outcome with the record on the ledger.

This capability can be useful in situations where opening a package to verify the contents would fundamentally alter the contents themselves (e.g., break the sterile field of packaged medical devices or trigger the enforcement of smart-contract conditions that are triggered by the opening of a package or item). It is also useful in situations where someone other than the end-user seeks to verify package contents without altering them (e.g., customs officers, regulators, etc.). In these situations, the contents of the package can be externally verified through a combination of the hash values of the digital documentation and the documentation itself. In the cases of customs inspectors who may be authorized to break seals to inspect package contents, hashing the video of the inspection and resealing of the packages could also be hashed and written the blockchain, including for instance, a law enforcement or customs blockchain to audit and verify actions and behaviors of those who access packages in commerce.

The ability to verify authenticity through this methodology can also be very useful for collectible or luxury goods that are being sold on a secondary market. In one example, a luxury watch maker can embed data on the packaging, the watch, or both that would allow a secondary purchaser to verify not only the authenticity of the watch, but also that the seller is the rightful owner, that the seller is an authorized dealer (e.g., not "grey market", that is legal but not within the system of authorized dealers on which a purchaser may rely for return, replacement, warranty, or even repair at their own expense). Digital documentation may also be augmented to include purchase receipts, warranty cards or claims, or other identifying information that can be linked to the original item and customer, hashed and written to the blockchain or shared ledger, then stored off-chain for retrieval and utilization in a future transaction such as a re-selling. This capability also allows manufacturers to gain insight into the life of their products following the initial sale. For high-end products, luxury goods, and industrial machinery, this represents a significant advantage, potentially generating resale, repair, or new customer acquisition opportunities during goods and equipment lifecycles.

This can generate enough trust to facilitate a great number of complicated interactions. For example, each party in the supply chain for a particular product can add a cryptographic hash documenting their value-addition as the item moves through the lifecycle. This can be used to resolve disputes, identify where problems occurred within the supply chain, or enforce contractual obligations like the example above. The nature of the technology is such at that each additional participant can build on the hash function of the previous participants, providing irrefutable cryptographic validation of the transaction:

Hash Function{[Item Originator]×[Item Generation]}=$H1$

Hash Function{[$H1$]×[Step 2 in Supply Chain]}=$H2$

Hash Function{[$H2$]×[Step 3 in Supply Chain]}=$H3$

Etc.

The hash function can be a known hashing algorithm, or an Exclusive OR (XOR) operation.

In this example, the supply chain life cycle can be "gated" and check points established with regards to quality, validity, or any other metric relevant to the item. At the point of each hash function, the item and the input are both validated, and become irrefutable. For instance, if the item was in acceptable condition at H2, but was not acceptable at H3, then the issue must be with Step 3 in the Supply Chain.

Additionally, public key/private key cryptographic functionalities can be added to create additional layers of validation or verification. Cryptographic hashes representing partner contributions can be generated using the partner's private key, which can be verified using the corresponding public key. This provides integrity and non-repudiation to the transaction. It is also possible to provide confidentiality to the transaction, whereby the hash elements of the transaction can be encrypted using the public key of a trusted third party. Then, in the instance of a dispute, only the trusted third party can use their private key to decrypt the hash values and examine the transactions. This could be particularly useful in situations where information regarding the participants or the transaction is sensitive (i.e. proprietary data, trade secrets, classified information, etc.). In these settings, the trusted third party can hold additional validation credentials (i.e. a security clearance) to add additional layers of trust to the transaction.

In some cases, a designer or copyright owner may designate that certain designs may only be printed in trusted environments, by trusted vendors, or otherwise limit printing to ensure that only authorized, paid for, properly licensed, or other restrictions are honored. This is similar to photo printer kiosks being present in photo departments of stores so that an attendant may verify that a photo is not being mass-copied, or photocopiers in libraries being located by the librarian desk to prevent someone from copying full books. The venue, attendant, or other components of the location act as deterrents to printing unauthorized items. Some cases might include artistic copyrights, patented parts, or those covered by other intellectual property rights such that rights will not be violated due to the nature of trust, human monitoring, or certification/licensure. For instance, a limited edition 3D printed sculpture might be limited to printing only in one location (e.g., popular vacation locations), or by one manufacturer's printer, or otherwise limited, and trust factors would be elements of decisions on where printed products could be authorized, with buyers assured of receiving what they have purchased.

In some cases, a high value item could be marked (similar to a watermark, embedded barcode, or other identifying factor) to assure its authenticity. This could be used in collectables which garner their value from limited editions, regional editions, or other similar supply constraints. Marking through additive manufacturing and/or packaging would assure that only that number authorized units would be printed, with the mark verifying for instance against a distributed ledger how many were printed and where, assuring authenticity and actual limited editions. Distributed ledger permissions and limits could be applied in such a way that it is similar to "breaking a mold" of a limited edition casting, so that no more may ever be produced. Watermarks can also be encoded into printed items such that scanners could be told not to allow replication similar to features in copiers that limit photocopying U.S. and other currencies despite technological capabilities. Printers and systems could be programmed to search permission white list and black list databases to determine if items may be printed based on watermark technologies, including such items as sensors, barcodes, QR codes, markings invisible to the human eye, patterns that appear to be part of the item but have marking functions, and other types of markings or indicators.

In some cases, a printer may receive only one part of a digital file at a time, may be restricted from copying or transmitting that portion to any other devices, and may be required to "prove" the design is deleted before receiving the next part of the design. The ability to prove that the first portion of the design may be implemented and enforced by software, firmware, or hardware of the 3D printer. For example, in order to be able to print parts requiring such proof, printer owners may be required to install a hardware DRM module in the printer which enables this proof and enforces the deletion of files after printing. In instances of required continuous printing, instructions could be received, buffered, executed, and deleted, while new instructions are being received and buffered so as not to interrupt printing. The printer and communications system can be secured for purposes of unauthorized printing, counterfeiting, design theft, or other conditions. An example of non-continuous 3D printing might be a drone with a body, wings, motors, and propellers. Purchasing one drone print might allow receiving the body design, printing the body, deleting that design, then receiving the wing design, printing the wings, deleting that design, and continuing in sequence with the motor(s), propellers, and so on. Each item which requires continuous printing could receive that design, but not the next part until it proves completion and deletion. Each operation may be written to a distributed ledger demonstrating compliance with the manufacturing process, the packaging process, and so on.

Example Techniques for Reducing Manufacturing and/or Shipping Costs

By utilizing a shared, distributed, immutable ledger to capture and verify each transaction on the network, and thus in a given supply chain or product life cycle, this data can be leveraged to help identify costs and inefficiencies in the manufacturing and shipping/logistics of anything produced utilizing the network and its resources. This can allow for changes in how items are manufactured, resulting in great savings for both producers and consumers.

In one example, the data available through a distributed manufacturing platform or the distributed ledger may be used to transform warehouses and fulfillment centers into production centers. In this example, additive manufacturing capabilities (i.e., 3D printers) could be installed in some or all of a particular warehouse or fulfillment center, changing the focus of the space from receiving, storing, and staging items to creating them. These spaces are naturally suited for this transition, as they are typically located in areas that are easily accessible to modes of transportation, have plenty of space, and have the ability to both bring resources in and send them out. These are all advantages that allow companies with warehouses that currently only serve as a middleman between producer and consumer to become the producer themselves.

In addition to increasing their own opportunity, this transition would significantly reduce the cost in all stages of the manufacturing process—including, but not limited to, lowering cost to produce the item by producing them closer to the point of use, lowering cost to ship the item by producing it closer to the point of use, reducing the cost to store or stage the item by producing it only when ordered and closer to the point of use, and being able to make iterative changes to the item without committing to a bulk production run.

Examples Solutions to the "Last Mile" Problem

By allowing manufacturers to produce items closer to their point of use, the technology described herein enables a host of other capabilities that can add value to the manufacturing and shipping process. Because our technology allows for on-demand production, a number of inputs or variables can be utilized to help solve the "last mile" problem that exists for so many with regards to logistics.

In one example, current conditions can be leveraged to determine packaging requirements at the time of production. For instance, current weather at the delivery location or forecast weather at the delivery time can dictate if the packaging needs to be water-resistant, water-proof, temperature controlled, etc. Other data points can include whether or not a customer will be physically present at the time and place of delivery (i.e., whether additional security or authentication capabilities need to be incorporated into the packaging), whether there are pets or children present at the location (particularly in the case of packaging food or medicine), whether the time in transit has the potential to impact the item, etc.

The on-demand manufacturing and packaging capabilities can also incorporate interactions from the end user to dictate some of these needs. In one example, the delivery mode or time can be based on customer availability, location, or other preference. In this example, the user may request that the delivery to be made to their office as soon as possible, and packaging for drone delivery can be created.

Other end-user input can be incorporated to create customized packaging in both shape and functionality. For example, it may be beneficial to print two layers of packaging for security, obfuscation, discretion, protection, or other reasons. External packaging can be customized to reflect the contents or minimize the attention the package might receive in transit. Branding for the interior packaging can be retained (i.e. consumer electronics with strong branding requirements). In another example, delayed access capabilities can be incorporated (i.e. a gift from a loved one that cannot be opened until your birthday, Christmas Day, etc.).

Examples Facilitating Interoperability

Significant challenges exist with regards to interoperability of design files and file types, as well as translation between two-dimensional designs or design components and three-dimensional designs and design components. The techniques described herein provide several direct solutions to these problems.

In some examples, an extensible platform can be enabled through an Application Programming Interface (API) of a distributed manufacturing platform that provides a level of commonality. The API may allow for the exchange or manipulation of multiple file types (e.g. CAD files, .PSD files, PDF files, standard 3D printer files such as .STL, .OBJ, .VRML, .DAE, .3MF, etc.). Translation capabilities also exist for measurements (i.e. between inches, centimeters, millimeters, etc.). The distributed manufacturing platform may additionally or alternatively be extensible through plugins or modules that can be developed by third-parties to work with their own proprietary or preferred formats. These and any of the other file processing operations described herein may be performed via the API or other interface of the distributed manufacturing platform.

Additional translation, mapping, or merge capabilities exist to merge a three-dimensional model with a two-dimensional design (e.g., to map a 2D image onto a 3D item, or two wrap a 3D item with a 2D wrap so that the image applied to the 3D object is not distorted). In this example, the API or other file translation software translates two-dimensional elements in a three-dimensional representation (e.g., applying a two-dimensional element to the surface of a three-dimensional object that has been produced via additive manufacturing). In some examples, existing drawing or rendering software may be adapted to translate two-dimensional images for application to three-dimensional parts. By way of example and not limitation, software products that can be adapted or interfaced with include templates for Adobe Illustrator, SignLab, CorelDraw, Photoshop, Gerber Advantage, and FlexiSign. The platform is also able to use multiple criteria to select the most appropriate printer for each element (i.e., which device should create the two-dimensional elements given which devices is creating the three-dimensional elements, etc.). In some examples, printers can be selected based on resolution, material, color, speed, cost, addressable print size, continuous print capacity (e.g., moving bed, moving print head, continuous sheet stock), maintenance, wear characteristics, such as fading "ink", worn print heads, alignment, leveling, and/or related characteristics. Some components or materials may employ floating print beds not subjected to vibration or movement. Selection may include proximity to additional "assembly line" printers for the other components that are 3D.

This translation, mapping, transposition, interpretation, and extrapolation capabilities allow the distributed manufacturing platform to provide color consistency (i.e. Pantone colors, ICC (International Colour Consortium) color map, etc.), standardized specifications regarding particular printing media, and a reverse-engineering capability whereby visual scans of physical items or original CAD files can be interpreted to facilitate digital creation and modification or the item or components of the item.

Example Distributed Finishing and Post Processing

The flexible nature of the distributed manufacturing techniques described herein with regards to file types and dimensions provides significant value to the finishing and post-processing phase of manufacturing. In this example, products can be created that merge three-dimensional objects and two-dimensional objects in a number of unique ways that were previously not feasible.

For example, a distributed manufacturing platform allows for a two-dimensional "shrink wrap," applique, or other covering to be printed in two dimensions and subsequently applied to a three-dimensional object. This can be done for protection, aesthetics, to provide customized branding or advertising, to create photo-realistic representations of an object, to apply a different surface finish, etc. These appliques may take the form of traditional shrink-wrapping, manifest as a simple iron-on applique, or become a full wrap where the "skin" is indistinguishable from the underlying three-dimensional frame. In some examples, after the wrap or cover is applied, the item may be heat treated to bond or fuse the skin to the item.

The distributed manufacturing platform allows customers to preview both how the two-dimensional wrapping will look on the completed package, but also how the two-dimensional item must be created to achieve that look, as well as illustrating the process to achieve the desired outcome (order of application for the wrapping components, modularity of the two-dimensional to achieve desired outcomes (i.e. two-part wraps, three-part wraps, etc.)).

Customized size, shape, configuration of wrapping, and other options such as customized sealing adhesives (e.g., tape) can be included in this portion of the process to achieve the desired outcome. Additionally, the platform can utilize "negative space" to provide visibility to the underlying object, creating additional opportunities to customize the final output, save costs on printing (e.g., no need to print black design elements if item itself is printed from black material, but instead leave that portion of the print clear or empty to allow the underlying material to show through).

The application of this type of post-processing can take place either at the same geographic location as the printing, or the platform allows for disparate geographic locations to be combined to achieve the desired outcome (e.g., the three-dimensional item is created in one location and the two-dimensional elements are created in another, and it is possible that they might be applied at a third location, or by the end consumer, etc.). Because the post-processing component can be disintermediated, these processes can take place in-transit (e.g., a team of people, processes, or machines can apply post-processing items en-route, and then can be packaged after post processing either en-route to the final destination or packaged at an intermediary destination after post-processing).

In that example, it is possible that the items can be delivered ready for post-processing, or delivered with temporary packaging, packaging that allows for final post-processing, packaging that includes supplies to perform post-processing, or packaging that can be used itself to perform post-processing (e.g., built-in tooling, stickers that can be applied to the item, etc.). Items can also be designed to be delivered with minimal packaging that does require some final assembly (similarly to how some popular Scandanavian furniture requires final assembly by the customer).

Example Reduction in Environmental Impact

In addition to offering increased functionality, reducing logistics overhead and other sources of friction, the techniques described herein greatly reduce the environmental impact of a given supply chain, something that is both difficult to do and in high-demand. In some examples, this is due to the ability to reduce associated fuel costs with transporting manufactured items. For example, by allowing manufacturers to produce items closer to the point of use, they can reduce the actual distance that a manufactured item must be shipped to reach the end user. Furthermore, by 3D printing a custom package for each item, the amount of packaging can be reduced to the minimum necessary amount for the given functionality requirements, and additionally the weight of any given amount of packaging is reduced to a minimum. By reducing both size and weight of packaging, without adversely impacting functionality (and potentially improving functionality and durability of the package), the weight of the cargo is reduced—thereby increasing fuel efficiency during transport—or the size of the cargo is reduced—thereby allowing more cargo to be shipped on a given modality (i.e. cargo ship, tractor trailer, box delivery truck, etc.)—or both.

By optimizing packaging materials based on functionality requirements and other dynamic inputs previously mentioned (package contents, weather, mode of transport, variable regarding the end-user, etc.) the 3D printed packaging and distributed manufacturing techniques allow manufacturers, shippers, and end-users to collaborate dynamically to create a balance of these competing factors. A goal of the platform is to optimize—not necessarily to minimize—packaging. This allows the platform to create packaging that can reduce breakage or insurance claims resulting from mishandling, incorporate biodegradable or reusable packaging, produce packaging that is both environmentally friendly and environmentally attuned, and incur additional costs (weight, size, materials, etc.) only when the involved parties agree that it is "worth it."

This agreement can be achieved dynamically in multiple ways. In some examples, the end user can select their packaging preferences, along with the associated impacts (e.g., some choices may increase or decrease cost, increase or decrease delivery time, etc.). In other examples, the end user and the manufacturer are interacting through the platform based on smart-contract capabilities (e.g., the end user orders an item and is willing to accept delivery within a given date or cost window, and the manufacturer can work to meet those requirements most efficiently). In other examples, this interaction can take place directly during the production and shipping lifecycle. In some examples, the end user may receive a notification by SMS message on a mobile device or push-notification within an application on a tablet or other computing device indicating that there is a possibility to change their order with proper incentives (e.g., another user is willing to purchase the same item at a higher price if they can get it more quickly, and the manufacturer might offer to share the balance of the increased sale price with the end user in exchange for re-routing their item to the higher bidder and accepting a later delivery in exchange for a cut of the margin or credit towards future purchase; or a truck is over capacity and a shipper might offer a discounted shipping charge if the item is put on a later truck, etc.). The system can utilize many factors in calculating opportunities for dynamic re-routing, including but not limited to possibility of increased sale price, item location, weather, shipping delays or impacts, past purchase behavior, time to replace the original item to the original customer, and more. When the system determines that an opportunity for an increase in revenue is possible, it sends notice to the potentially impacted customer, who has now become a partner in realizing this additional value. The recipient of notice can then immediately and finally accept or reject the proposal, or, in some cases, propose an alternative arrangement (i.e. an increase or decrease in the amount of compensation, amount of time they are willing to bear in order to receive their item, etc.). The system can then re-calculate the opportunity and accept or reject the counter-proposal. In instances where the counter-proposal does not impact the secondary customer's purchase offer (i.e. it aligns with their purchase terms on both price and time), the system can accept the counter-offer and make the appropriate changes in the shipping, routing, or other supply chain components. In instances where the counter-proposal does impact the secondary customer's purchase offer (i.e. an increased price or timeline than originally tendered), the system can then notify the secondary customer of the new offer. The secondary customer can continue to negotiate, or choose to accept or reject the offer outright. The negotiation process can continue until a final acceptance or rejection is achieved. If an acceptance of new terms is reached by all parties, the outcome of this newly altered transaction are then automatically written to the blockchain or shared ledger to indicate the change was made, and the system may or may not choose to include the terms of the negotiation. If the new offer is rejected by any party, the system can then seek a new potential opportunity and begin the negotiation process again. In these examples, multiple parties are able to interact and achieve outcomes that are beneficial for all—the manufacturer, the original purchaser, the shipper, and the new customer willing to pay more—where all feel satisfied with the arrangement.

The techniques described herein can further reduce the environmental impact of a given supply chain by utilizing the packaging in fundamentally new ways. In addition to offering both recyclable packaging options and biodegradable packaging options, it is possible to design both interactions and functionality into the packaging to achieve this reduced impact. In some examples, this involves opening the package immediately upon receipt and inspecting the final item. In this example, the delivery mechanism (postal worker, drone, ride-share driver, messenger, etc.) can serve as an external validator of both successful delivery to the identified recipient and the undamaged and fully functional status of the product. In addition to this third-party validation of a successful transaction, the packaging itself is designed to be recovered by the delivery mechanism on-the-spot for recycling or reuse and the end user may receive some financial compensation for returning or reusing their packaging.

In some examples, the packaging may be design to collapse, fold in, fold flat, disassemble, or otherwise be reduced in size and bulk for return transport. In other examples, the packaging may be collected by a third party (municipality, private company, neighborhood association, apartment building, etc.) in bulk and then repurposed in batches.

In other examples, the packaging itself can be designed to be "reversible" and enable additional engagements. For instance, returning an item may be as simple as "reversing" the packaging in whole or in part to re-secure the item and update the shipping location back to the manufacturer or retailer. In some examples, this may take the form of two-piece packaging where the top portion can be reversed to reveal a pre-labeled return address while the bottom portion can remain suited to provide safe passage to the item. In other examples, the shipping destination may be represented by a machine-readable code (e.g., Barcode, Quick Response Code, RFID tag, Bluetooth/Zigbee beacon, etc.) and the end user can simply alter the representation of that destination code back to the manufacturer or return center through a web portal, mobile phone app, or interaction with the delivery mechanism. By simply changing the address in the backend database and not the physical representation on the packaging, this permanent or semi-permanent addressing mechanism can allow for more durable packaging to be re-used many times, either by being returned to the manufacturer to ship another item, or forwarded on to the nearest manufacturing location in need of that type of packaging.

In some examples, new items being delivered may be replacing items that can be refurbished or remanufactured (e.g., phones, electronic toothbrush heads, glasses, printer cartridges, ammunition casings, auto parts, etc.). In these cases, the packaging can be utilized to not only deliver the new item, but also package one or multiple of the items being replaced. These items can be returned to the manufacturer directly, forwarded to a different location for re-manufacture, or shipped on to a third party for recycling, repurposing, or some other use. In combination with the permanent machine-readable addressing, the destination of the items being replaced can be done dynamically (e.g., through an online auction where the highest bidder receives the item) or through direct integration with other supply chain components. This capability will reduce unnecessarily shipping items to a depot, warehouse, or other staging area and will instead send them directly to their next point of use.

In some examples, this remanufacturing can be accomplished through additional additive manufacturing (e.g., printing additional material on a worn part to restore functionality, printing new threads onto a pipe or screw, adding layers of enamel to dental implants, resoling shoes, etc.). The techniques described herein allow for these items to reach their refurbisher quickly, efficiently, and with minimal waste by using some or a combination of the above technologies to get remanufacturable parts into the hands of those who can capture, restore, and add value to the items. The same packaging can then be used to send the remanufactured item onto a new user, and restart the virtuous cycle, adding to or repairing the packaging as needed in a similar manner.

There are also examples where remanufacturing offers an opportunity to increase functionality beyond what was originally possible (e.g., upgrading from stainless steel to titanium, adding carbide or diamond components to a saw, etc.). This capability can be incorporated into not only the capture and return of the item, but also in the sales and distribution of enhanced items, all utilizing a consistent packaging platform.

Examples of Source Identification and Verification

Significant challenges surround capturing and validating inputs of a particular supply chain (source of raw materials, proving provenance, preventing tampering or fraud, etc.). The distributed manufacturing and blockchain enabled packaging techniques described herein allow for several novel solutions to this problem.

In some examples, the packaging of an item can contain geolocation data (e.g., automatically recorded by a sensor suite in/on the package, input by a manufacturer or certification authority manually or automatically) to authenticate point of manufacture (e.g., if a diamond is sourced from Canada, it can't be a "blood diamond"; champagne is sourced from the proper region in France, etc.). This geolocation data can be written into or onto the packaging in an unalterable way (e.g., through an embedded sensor such as GPS that both generates and retains the data, an embedded sensor that only retains the data such as a RFID or NFC tag, Bluetooth/Zigbee, etc.). Additionally or alternatively physical code (either machine readable such as a Barcode, Quick Response Code, watermark, or human readable such as serial number or other unique identifier) can be printed as part of the packaging, any of which can then be verified utilizing a distributed, shared, immutable ledger to retrieve and verify relevant details.

In addition to geolocation, other data can be added to the packaging, as well, which can also be verified at later points in the supply chain or at the point of use. This might include, but is not limited to, type and source of raw materials, batch of material, material data sheet, any relevant verifications, approvals, or certifications (e.g., FDA-approved, certified organic, non-GMO verified, licensed, etc.). In addition to the packaging, it is possible to move the verification upstream to the point of manufacture and certify the make, model, identifier, and/or owner of the printer and/or contents of the printer (e.g., print media, printer cartridge, etc.). In this instance, the data would represent the source of manufacture, which could then be verified for a given time and date utilizing the shared, distributed ledger to ensure authenticity.

These solutions can be combined, where in the printer itself writes the contents of the package to the packaging itself. This can be done discretely on the internals of the packaging so that only the end user can verify the contents (e.g., via a machine readable code or watermark), or externally allowing a potential customer or participant in the supply chain to verify the contents without opening the packaging.

Because of the underlying nature of the ability to store, share, and retrieve this data, our platform allows for sophisticated analytics capability based on the movement of raw materials, printers, and packages.

Example Military/Defense Use Cases

Additional use-cases for deriving packaging requirements from the domain of use can be found in military situations. In this example, the mode of delivery (underwater, drone, glider, etc.), time of delivery (day vs. night), contents (food vs. weapons vs. intelligence), environment (colors, camouflage), authorization (classified contents), etc. can all be incorporated dynamically into the packaging requirements when the item is produced.

Example Aviation/Aerospace Use Cases

Private aviation uses a system of Fixed Base Operators who are located at airports and airstrips around the nation and around the world. The Fixed Base Operators provide repairs, provisions, fuel, regular preventive maintenance and related services. In some examples, printers can be deployed to these locations which can print consumable parts, replacement parts (damaged or broken), and packaging to store the parts for marketing, storage, and use, may eliminate the need to order and transport specific parts, or store spare parts. Consumables may be printed, packaged, stored, sold, and used. Using a distributed manufacturing and package system may allow branding for specific airlines, operators, lessors, and owners (e.g, Delta, NetJets, Sentient Jets, XOJet), or a specific Fixed Base Operator. The function of packaging may include branding, consumer confidence, instructions, protection, or other uses. Distributed manufacturing provides each aircraft owner or operator, Fixed Base Operator, and others the ability to manufacture on demand, in situ, without waiting for parts shipment or even fabrication, wherever located in the world. Similarly, private boating and yachting uses a system or private marinas, ship builders, and other facilities. Ships may also tend to be in use for long periods of time, with manufacturers being sold, acquired, shut down, or transitioning to other manufacturing lines and technologies. Parts for boats, ships, yachts, and other marine equipment, including consumables are also potential users of these technologies.

Distributed manufacturing is a better alternative for airports and FBOs than airlines owning their own printers, which may be used only infrequently, and would have unused capacity. In the alternative, an airline that owned printers could lease capacity to others. Using a certified, maintained, printer may be used to comply with Federal Aviation Association (FAA) certification of parts, and usage of the printers by certified mechanics might also be required and specified in a product specification or work order. Using distributed ledger or blockchain to track use, maintenance, materials, and tolerances, as well as manufacturing conditions may be used to provide assurances to the FAA that satisfies regulatory and safety concerns.

In some cases, engine parts, landing gear parts, exit door parts, and other items which impact the safety of the aircraft, crew, or passengers, may be printed of specialty materials, certified processes, certified designs, licensed IP for newer planes, and the distributed manufacturing platform coupled with packaging that tracks manufacture, shelf life, storage or transportation conditions, and other alternatives, may allow on-site production that satisfies both the IP owner (Boeing, Airbus, Embraer, or any subcontracted parts supplier) and the FAA, as well as the airline, airplane operator, or lessor/lessee, or owner. The combination of trackable manufacture, certification of materials, design, printer maintenance, specifications, and other components of the process add value, and ability to put the part in the end user's hands as quickly as possible, adding economic value, reducing passenger inconvenience, preventing crew time outs, and other added benefits. Doing all of this while seamlessly licensing any applicable intellectual property via smart contracts reduces cost and streamlines the transaction.

In some examples, mobile response teams, FBOs, trucks, trains, etc. may include printers printing on location or en route. For private aviation and yachting, many designers, manufacturers, and operators provide mobile response teams. Similar operations exist in long-haul trucking, trains, and other transportation systems that are high value and disruptive when out of services. Mobile response teams may respond to fixed locations or the location of a breakdown, and may have typical parts available for use, however, on arrival on location may discover needs for additional or different parts. Mobile printers could be used at that point.

In some cases, the print time for an item may be similar to the travel time for a mobile response team. If the part required is known, the printer could begin printing on dispatch with the part completed and available on arrival. This could include printers located on trains, planes, ships, semi-trucks, panel vans, or other service vehicles.

Additional locations and needs could include commercial ports, free trade zones at airports, ports, inland ports, and other locations, in warehouses or other centralized transportation logistics centers, and might include printers, materials, access to networks, scanners, robotics, and other technologies. Mobile printers, print bureaus, and other opportunities (to include financing, franchising print bureaus that are generic, industry, or location specific are also potential uses of these distributed manufacturing opportunities and technologies as applied.

CONCLUSION

Although the subject matter has been described in language specific to structural features and/or methodological acts, it is to be understood that the subject matter defined in the appended claims is not necessarily limited to the specific features or acts described. Rather, the specific features and acts are disclosed as exemplary forms of implementing the claims.

A module may provide one or more functions, and may be configured in software executed by one or more processors (e.g., central processing units, graphics processing units, etc.), configured in hardware, such as an application specific integrated circuit (ASIC) or field programmable gate array (FPGA), or may be configured in a combination of software and hardware. A module defined in software may be a subroutine or a stand-alone application. In a data center or cloud environment, a module may be configured using an arbitrary number of servers or other computing devices. A module may be an arbitrary grouping of techniques and/or functionality, based on particular design goals or resource availability.

While various modules, services, devices, managers, platforms, etc., have been discussed, it should be realized that these examples are representative of more general techniques. Accordingly, the techniques and concepts discussed herein could be performed by other functional blocks in a manner that group functions and techniques differently. Accordingly, the structures, techniques and methods described herein are intended to be representative of a set of functions and may be performed using more, less or different modules, managers, platforms, systems, methods, etc.

Additionally, this application describes a number of related topics and techniques. These topics and techniques may be performed individually, or in any combination with each other or other topics or techniques, as desired to achieve particular design goals. For instance, while various aspects of distributed manufacturing techniques are described separately from various aspects of blockchain enabled packaging, these aspects can be used separately or in combination with one another.

In some examples, a method of manufacturing, packaging and providing verification of authenticity of medicine, comprises: manufacturing a medicine; signing a certificate identifying the medicine using a private key of a manufacturer; writing the signed certificate to a blockchain; and printing a package using a 3D printer to enclose the medicine and to include the signed certificate in a machine-readable form. In some examples, the machine-readable form is an optical code defined on the package. In some examples, printing the packaging comprises: including within the printed package at least one sensor configured to detect at least one of: motion; temperature; or GPS-based location. In some examples, printing the packaging further comprises including a memory device within the package, and wherein the method further comprises: signing a prescription to a patient with a private key of a prescriber of the medicine and a public key of the patient; and writing the signed prescription to the memory device included within the package. In some examples, the method further comprises: signing a prescription to a patient with a private key of a prescriber of the medicine to the patient and with a public key of the patient; and writing a result of the signing to the blockchain. In some examples, the method further comprises at a pharmacy: scanning the signed certificate of the package to obtain a first data; reading the blockchain to obtain a second data; verifying the prescription of a patient using: the first data and a public key of the manufacturer; and the second data, a public key of the prescriber of the medicine, and a private key of the patient. In some examples, the method further comprises at a pharmacy: verifying if the medicine was manufactured by the manufacturer, based at least in part on operation of a public key of the manufacturer; and verifying if the blockchain contains a record of manufacture of the medicine; and dispensing the medicine based on success of both verification steps. In some examples, the method further comprises at a pharmacy: verifying a prescription of a patient by an operation including a private key of the patient and a public key of a prescriber, wherein the verifying comprises: reading from a device of the package; and reading from a blockchain.

What is claimed is:

1. A method of manufacturing, packaging and providing verification of authenticity of a medication, comprising:

manufacturing, by operation of an additive manufacturing process, the medication including two or more medicines according to two or more respective doses;

signing a certificate identifying the two or more medicines using a private key of a manufacturer, wherein the certificate comprises at least one of a make of a first three-dimensional (3D) printer that printed the medication, a model of the first 3D printer that printed the medication, an identifier of the first 3D printer that printed the medication, or an owner of the first 3D printer that printed the medication;

writing the signed certificate to a blockchain;

using a multiparty collaboration process to design multiple different sets of packaging for the medication;

selecting a selected set of packaging from among the multiple different sets of packaging, wherein the multiple different sets of packaging are available for the medication;

printing a package according to the selected set of packaging using the first 3D printer or a second 3D printer to enclose the medication and to include the signed certificate in a machine-readable form, wherein the printing the package comprises:

printing the package partially to enclose a first medicine of the two or more medicines;

suspending the printing of the package;

adding a second medicine of the two or more medicines to the first medicine; and completing the package to include both the first medicine and the second medicine.

2. The method of claim 1, wherein the machine-readable form is an optical code defined on the package.

3. The method of claim 1, wherein printing the packaging comprises:

including within the package at least one sensor configured to detect at least one of:

motion;

temperature; or global positioning system-based location.

4. The method of claim 1, wherein printing the packaging further comprises including a memory device within the package, and wherein the method further comprises:

signing a prescription to a patient with a private key of a prescriber of the medication and a public key of the patient; and writing the signed prescription to the memory device included within the package.

5. The method of claim 1, further comprising:

signing a prescription to a patient with a private key of a prescriber of the medication to the patient and with a public key of the patient; and writing a result of the signing to the blockchain.

6. The method of claim 5, further comprising at a pharmacy: scanning the signed certificate of the package to obtain a first data; reading the blockchain to obtain a second data; verifying the prescription of the patient using: the first data and a public key of the manufacturer; and the second data, a public key of the prescriber of the medication, and a private key of the patient.

7. The method of claim 1, further comprising at a pharmacy:

verifying if the medication was manufactured by the manufacturer, based at least in part on operation of a public key of the manufacturer; and verifying if the blockchain contains a record of manufacture of the medication; and dispensing the medication based on success of both verification steps.

8. The method of claim 1, further comprising at a pharmacy:
verifying a prescription of a patient by an operation including a private key of the patient and a public key of a prescriber, wherein the verifying comprises:
reading from a device of the package; and
reading from the blockchain.

9. The method of claim 1, wherein the medication comprises the first medicine and the second medicine combined into a single delivery mechanism, wherein the delivery mechanism comprises a pill.

10. The method of claim 1, wherein the medication comprises the first medicine and the second medicine combined into a single delivery mechanism, wherein the delivery mechanism comprises a patch.

11. The method of claim 1, wherein the printing the package is performed by the second 3D printer, and wherein the certificate further comprises at least one of a make of the second 3D printer that printed the package, a model of the second 3D printer that printed the package, an identifier of the second 3D printer that printed the package, or an owner of the second 3D printer that printed the package.

12. The method of claim 1, wherein the printing the package is performed at a pharmacy.

13. The method of claim 11, wherein: the printing the package is performed by the second 3D printer, the owner of the first 3D printer is the manufacturer of the medication, the owner of the second 3D printer is a pharmacy at which the package is printed, and the certificate includes identifiers of both the manufacturer of the medication and the pharmacy at which the package is printed.

14. The method of manufacturing of claim 1, wherein:
the additive manufacturing process results in a multi-medication pill comprising the first medicine and the second medicine; and
the printing the package results in a single package including multiple medications.

15. A method of manufacturing, packaging and providing verification of authenticity of medicine, comprising:
manufacturing a medicine by printing the medicine using a first three-dimensional (3D) printer;
signing a certificate identifying the medicine using a private key of a manufacturer, wherein the certificate comprises a make of the 3D printer that printed the medicine, a model of the first 3D printer that printed the medicine, an identifier of the first 3D printer that printed the medicine, and an owner of the first 3D printer that printed the medicine;
writing the signed certificate to a blockchain; and
printing a package using a second 3D printer to enclose the medicine and to include the signed certificate in a machine-readable form;
wherein the certificate further comprises at least one of a make of the second 3D printer that printed the package, a model of the second 3D printer that printed the package, an identifier of the second 3D printer that printed the package, or an owner of the second 3D printer that printed the package, and
wherein the owner of the first 3D printer is a manufacturer of the medicine, and wherein the owner of the second 3D printer is a pharmacy at which the package is printed, and wherein the certificate includes identifiers of both the manufacturer of the medicine and the pharmacy at which the package is printed.

16. The method of claim 15, wherein:
the medicine comprises multiple medicines each having a respective dose, the multiple medicines being combined into a single delivery mechanism,
the multiple medicines and the respective dose of each medicine is customized for an individual customer.

17. The method of claim 16, wherein the delivery mechanism comprises a pill.

18. The method of claim 16, wherein the delivery mechanism comprises a patch.

19. The method of claim 15, further comprising at the pharmacy:
verifying if the medicine was manufactured by the manufacturer, based at least in part on operation of a public key of the manufacturer; and
verifying if the blockchain contains a record of manufacture of the medicine;
and dispensing the medicine based on success of both verification steps.

20. The method of claim 15, further comprising at the pharmacy:
verifying a prescription of a patient by an operation including a private key of the patient and a public key of a prescriber, wherein the verifying comprises:
reading from a device of the package; and
reading from the blockchain.

* * * * *